(12) United States Patent
Dovzhenko et al.

(10) Patent No.: US 10,301,635 B2
(45) Date of Patent: May 28, 2019

(54) METHOD FOR INTRODUCING A POLYNUCLEOTIDE INTO NON-ADHESIVELY GROWING PLANT CELLS

(75) Inventors: Oleksandr Dovzhenko, Freiburg (DE); Claude Becker, Tuebingen (DE); Karsten Voigt, Freiburg (DE); Klaus Palme, Pulheim (DE)

(73) Assignee: SCREENSYS GMBH, Freiburg (DE)

( * ) Notice: Subject to any disclaimer, the term of this patent is extended or adjusted under 35 U.S.C. 154(b) by 1531 days.

(21) Appl. No.: 13/988,276

(22) PCT Filed: Nov. 21, 2011

(86) PCT No.: PCT/EP2011/070602
§ 371 (c)(1),
(2), (4) Date: Aug. 26, 2013

(87) PCT Pub. No.: WO2012/066147
PCT Pub. Date: May 24, 2012

(65) Prior Publication Data
US 2013/0330717 A1    Dec. 12, 2013

(30) Foreign Application Priority Data
Nov. 19, 2010 (EP) .................... 10191985

(51) Int. Cl.
*C12N 15/82* (2006.01)
*C12N 5/14* (2006.01)

(52) U.S. Cl.
CPC ........... *C12N 15/8206* (2013.01); *C12N 5/14* (2013.01); *C12N 15/8218* (2013.01)

(58) Field of Classification Search
CPC .............................................. C12N 15/8201
See application file for complete search history.

(56) References Cited

U.S. PATENT DOCUMENTS

2002/0173037 A1   11/2002   Pati et al.

FOREIGN PATENT DOCUMENTS

EP    0 465 875 A1    1/1992

OTHER PUBLICATIONS

Becker (Inaugural-Dissertation zur Erlangung der Doktorwürde an der Fakultät für Biologie der Albert-Ludwigs-Universität Freiburg, pp. 1-104, 2009).*
Kansagara et al. (cited in IDS, Nature Methods, pp. 1-2, (2008)).*
Fukui et al. (Journal of Bioscience and Bioengineering, vol. 94, No. 1, pp. 97-91, (2002)).*
Pati et al. (cited in IDS, Protoplasma, (2005), 226: pp. 217-221).*
Bart et al. (cited in IDS, Plant Methods, (2006)).*
Dovzhenko et al 1998, 204: 114-118.*
Ossowski et al 2008 The Plant Journal 53: 674-69.*
Bart, Rebecca, et al., Plant Methods (Jun. 29, 2006), vol. 2(1):13, pp. 1-9.
Becker, Claude, "RNAi-mediated gene silencing by small non-coding RNAs in protoplasts of *Arabidopsis thaliana*", Alberts-Ludwigs-Universitaet Freiburg, Dec. 2009, pp. cover-104.
Craig, W. et al., Plant Cell Reports (Dec. 1, 2005), vol. 24(10), pp. 603-611.
Dovzhenko, A. et al., Protoplasma (1998), vol. 204 (1-2), pp. 114-118.
Kansagara, AG et al., Nature Methods (Sep. 2008), vol. 5(9), pp. 1-2.
Pati, PK et al., Protoplasma (Dec. 1, 2005), vol. 226 (3-4), pp. 217-221.
Schnabl, H et al., International Journal of Biochemistry (Jan. 1, 1988), vol. 20(6), pp. X.
Winkelmann, Traud et al., Plant Cell, Tissue and Organ Culture (Jul. 20, 2006), vol. 86(3), pp. 337-347.
Yamada, Yasuyuki et al., Methods in Molecular Biology (2010), vol. 643, pp. 33-45.
Yoo, Sang-Dong et al., Nature Protocols (2007), vol. 2(7), pp. 1565-1572.

* cited by examiner

*Primary Examiner* — David H Kruse
(74) *Attorney, Agent, or Firm* — Chalin A. Smith; Smith Patent, LLC

(57) ABSTRACT

The present invention relates to a method for introducing a polynucleotide into non-adhesively growing plant cells, comprising the following steps: providing a solid support having immobilized thereto the polynucleotide in dry state; contacting the plant cells with the polynucleotide on the solid support so as to obtain transformed plant cells; and optionally washing the plant cells.

19 Claims, 23 Drawing Sheets
Specification includes a Sequence Listing.

SEQUENCE LISTING

```
<160> NUMBER OF SEQ ID NOS: 145

<210> SEQ ID NO 1
<211> LENGTH: 11618
<212> TYPE: DNA
<213> ORGANISM: Artificial Sequence
<220> FEATURE:
<223> OTHER INFORMATION: amiRNA screening vector designated
      pMIR-AT1G73590-mGFP5-4

<400> SEQUENCE: 1
```

```
ttgtacaaag tggtgatcct ccgttccatg ggctagaagc tctagttcta gagtccgcaa      60
aaatcaccag tctctctcta caaatctatc tctctctatt tttctccaga ataatgtgtg     120
agtagttccc agataaggga attagggttc ttatagggtt tcgctcatgt gttgagcata     180
taagaaaccc ttagtatgta tttgtatttg taaaatactt ctatcaataa aatttctaat     240
tcctaaaacc aaaatccagt gaccgggcgg ccgccaccgc ggtggagggg atcagattg      300 tcgtttcccg ccttcagttt agcttgcatg cctgcaggtt agcttgcatg ctgcaggtcg     360
actctctagg aatttgttcg tgaactatta gttgcgggcc ttggcatccg actacctctg     420
cggcaatatt atattccctg gcccaccgt gaacccaatt tcgcctattt attcattacc      480
cccattaaca ttgaagtagt catgatgggc ctgcagcacg ttggtgaggc tggcacaact     540
catccatata ctttctgacc ggatcggcac attattgtag aaaacgcgga cccacagcgc     600
actttccaaa gcggtgccgc gtcagaatgc gctggcagaa aaaattaat ccaaaagtac      660 cctccaagca gcccatataa acgcgtttac aaatccgcta acctcaacaa tttgagcaga     720
gaaaattcgc tagaggatcc ccgggtaccg agctcgaatt ctcaacacaa catatacaaa     780
acaaacgaat ctcaagcaat caagcattct acttctattg cagcaattta aatcatttct     840
tttaaagcaa aagcaatttt ctgaaaattt tcaccattta cgaacgatag ccatggtgag     900
caagggcgag gaggataaca tggccatcat caaggagttc atgcgcttca aggtgcacat     960
ggagggctcc gtgaacggcc acgagttcga gatcgagggc gagggcgagg ccgcccta     1020 cgagggcacc cagaccgcca agctgaaggt gaccaagggt ggccccctgc ccttcgcctg     1080
ggacatcctg tcccctcagt tcatgtacgg ctccaaggcc tacgtgaagc accccgccga     1140
catccccgac tacttgaagc tgtccttccc cgagggcttc aagtgggagc gcgtgatgaa     1200
cttcgaggac ggcggcgtgg tgaccgtgac ccaggactcc tccctgcagg acggcgagtt     1260
catctacaag gtgaagctgc gcggcaccaa cttcccctcc gacggccccg taatgcagaa     1320
gaagaccatg ggctgggagg cctcctccga gcggatgtac cccgaggacg gcgccctgaa     1380
gggcgagatc aagcagaggc tgaagctgaa ggacggcggc cactacgacg ctgaggtcaa     1440
gaccacctac aaggccaaga gcccgtgca gctgcccggc gctacaacg tcaacatcaa      1500 gttggacatc acctcccaca acgaggacta caccatcgtg aacagtacg aacgcgccga      1560 gggccgccac tccaccggcg gcatggacga gctgtacaag taatctagag tccgcaaaaa     1620
tcaccagtct ctctctacaa atctatctct ctctattttt ctccagaata atgtgtgagt     1680
agttcccaca taagggaatt agggttctta tagggtttcg ctcatgtgtt gagcatataa     1740
gaaaccctta gtatgtattt gtatttgtaa aatacttcta tcataaaat ttctaattcc      1800 taaaaccaaa atccagtgac ctgcaggcat gcaagctaaa ctatcagtgt ttgacaggat     1860
atattggcgg gtaaacctaa gagaaaagag cgtttattag aataatcgga tatttaaaag     1920
ggcgtgaaaa ggtttatccg ttcgtccatt tgtatgtgta catcaccgac gagcaaggca     1980
agaccgagcg cctttccgac gctcaccggg ctggttgccc tcgccgctgg gctggcggcc     2040
gtctatggcc ctgcaaacgc gccagaaacg ccgtcgaagc cgtgtgcgag acaccggccg     2100
ccggcgttgt ggatacctcg cggaaaactt ggccctcact gacagatgag gggcggacgt     2160
tgacacttga ggggccgact caccccgcgc ggcgttgaca gatgaggggc aggctcgatt     2220
tcggccggcg acgtggagct ggccagcctc gcaaatcggc gaaaacgcct gattttacgc     2280
gagtttccca cagatgatgt ggacaagcct ggggataagt gccctgcggt attgacactt     2340
```

```
gaggggcgcg actactgaca gatgaggggc gcgatccttg acacttgagg ggcagagtgc    2400
tgacagatga ggggcgcacc tattgacatt tgagggctg tccacaggca gaaaatccag     2460
catttgcaag ggtttccgcc cgttttcgg ccaccgctaa cctgtctttt aacctgcttt     2520
taaaccaata tttataaacc ttgttttaa ccagggctgc ccctgtgcg cgtgaccgcg      2580 cacgccgaag gggggtgccc cccttctcg aaccctcccg gcccgctaac gcgggcctcc    2640
catcccccca gggctgcgc ccctcggccg cgaacggcct caccccaaaa atggcagcgc    2700
tggcagtcct tgccattgcc gggatcgggg cagtaacggg atgggcgatc agcccgacaa    2760
gctaccccta tttgtttatt tttctaaata cattcaaata tgtatccgct catgagacaa    2820
taaccctgat aaatgcttca ataatattga aaaggaaga gtatgagtat tcaacatttc     2880
cgtgtcgccc ttattccctt ttttgcggca ttttgcctc ctgttttgc tcacccagaa     2940 acgctggtga agtaaaaga tgctgaagat cagttgggtg cacgagtggg ttacatcgaa     3000
ctggatctca acagcggtaa gatccttgag agttttcgcc ccgaagaacg ttttccaatg   3060
atgagcactt ttaaagttct gctatgtggc gcggtattat cccgtattga cgccgggcaa   3120
gagcaactcg gtcgccgcat acactattct cagaatgact tggttgagta ctcaccagtc   3180
acagaaaagc atcttacgga tggcatgaca gtaagagaat tatgcagtgc tgccataacc   3240
atgagtgata acactgcggc caacttactt ctgacaacga tcggaggacc gaaggagcta   3300
accgcttttt tgcacaacat gggggatcat gtaactcgcc ttgatcgttg gaaccggag    3360 ctgaatgaag ccataccaaa cgacgagcgt gacaccacga tgcctgtagc aatggcaaca   3420
acgttgcgca aactattaac tggcgaacta cttactctag cttcccggca acaattaata   3480
gactggatgg aggcggataa agttgcagga ccacttctgc gctcggccct tccggctggc   3540
tggtttattg ctgataaatc tggagccggt gagcgtgggt ctcgcggtat cattgcagca   3600
ctggggccag atggtaagcc ctcccgtatc gtagttatct acacgacggg gagtcaggca   3660 actatgatg aacgaaatag acagatcgct gagataggtg cctcactgat taagcattgg   3720
taactgtcag accaagtta ctcatatata ctttagattg atttaaaact tcatttttaa    3780
tttaaaagga tctaggtgaa gatcctttt gataatctca tgaccaaaat cccttaacgt   3840
gagttttcgt tccactgagc gtcagacccc gtagaaaaga tcaaaggatc ttcttgagat   3900 ccttttttc tgcgcgtaat ctgctgcttg caaacaaaaa aaccaccgct accagcggtg   3960
gtttgtttgc cggatcaaga gctaccaact ctttttccga aggtaactgg cttcagcaga   4020
gcgcagatac caaatactgt ccttctagtg tagccgtagt taggccacca cttcaagaac   4080
tctgtagcac cgcctacata cctcgctctg ctaatcctgt taccagtggc tgctgccagt   4140
ggcgataagt cgtgtcttac cgggttggac tcaagacgat agttaccgga taaggcgcag   4200
cggtcgggct gaacggggg ttcgtgcaca gcccagct tggagcgaac gacctacacc     4260
gaactgagat acctacagcg tgagctatga gaaagcgcca cgcttcccga agggagaaag   4320
gcggacaggt atccggtaag cggcagggtc ggaacaggag agcgcacgag ggagcttcca   4380
gggggaaacg cctggtatct ttatagtcct gtcgggttc gccacctctg acttgagcgt    4440
cgatttttgt gatgctcgtc aggggggcgg agcctatgga aaaacgccag caacgcggcc   4500 ttttacggt tcctggcctt tgctggcct tttgctcaca tggactctag ctagaggatc     4560
acaggcagca acgctctgtc atcgttacaa tcaacatgct accctccgcg agatcatccg   4620
tgtttcaaac ccggcagctt agttgccgtt cttccgaata gcatcggtaa catgagcaaa   4680
gtctgccgcc ttacaacggc tctcccgctg acgccgtccc ggctggcacg acaggtttcc   4740
```

```
cgactggaaa gcgggcagtg agcgcaacgc aattaatgtg agttagctca ctcattaggc   4800
accccaggct ttacacttta tgcttccggc tcgtatgttg tgtggaattg tgagcggata   4860
acaatttcac acaggaaaca gctatgacca tgattacgcc aagcttgcat gcctgcaggt   4920
cactggattt tggttttagg aattagaaat tttattgata gaagtatttt acaaatacaa   4980
atacatacta agggtttctt atatgctcaa cacatgagcg aaaccctata agaaccctaa   5040
ttcccttatc tgggaactac tcacacatta ttctggagaa aaatagagag agatagattt   5100
gtagagagag actggtgatt tttgcggact ctagatgcat gctcgagcgg ccgccagtgt   5160
gatggatatc tgcagaattc gcccttttcta gatcatagac caagagaat gtagtagaga   5220 agagttatgg gcaacgcgat caacatccca aatatcaccg cagtgctaag aatgtcagga   5280
tgcacattat actctttggc aaacacaaac ggtactattc cttgcggcaa agctgcctgg   5340
ataatggcaa catggaggag gacgccacgg aggccaacgg cataagaagc aacgagcatg   5400
acggcaggtc caacgacaaa tctcatagcc gccgcaaaag ctgctcttct gtttccacaa   5460
gctattattc ttgggtttaa cgccatgaac aacccaagac tgaacatagc catgcctaga   5520
cctgcatctg agagtatgga gatagacttt gctataagag ctggcatttc aatgttccac   5580
ttgaaggaaa tgagggacca ggtgatgccg aataaactgg agtaagagtt gggattacga   5640
ataagtttcc tccaaaccat aatgagaatg agtcttgtca tcacacttgt tggtggcatc   5700
accttagcct gcgtcgtttt gttgcttatg ttgttcccac cgtccgttgc caatactttg   5760
ctatcatcgt ctttgttacc gaaactaaac tcttccctct ccacgtactg gttgtcgtta   5820
ctattcccct gaggtacaga gatcttaacg tccttttgat gatcgttcgt agcggtggag   5880
taatcggcgt ggtggtttcc tcctccaccg ccgaacacat ctgagaccgg cgaagcactt   5940
gagctccaca caaacatgtg aagatctctt ccgtttccgt cttgtctttt cccaccaacc   6000
accggagcgt ttcctttcgc cgccgtgcct ccaccaccgc cagtgttggg cgaaaacatc   6060
cctgggttcg gcgccggata atgcgctcct ccaccgccac cacttcctcc agattgataa   6120
tgaaacctcc cagctccagc agcagttcca gcagccgtcg gtttagcagg accaccgtct   6180
tcttcgtagt tggaaggtct cggagtagga cctttagaac caaacacagc ttctccagga   6240
ccaaagttag agttccgacc accaccagaa gccatcatcg agtaaaaatc agtatgatta   6300
aaactagagc cacgtggcgt tgggtttctt gaactctgaa gcgaatatat ctcagcgttg   6360
gttagattcg aaggtctagg tgtcgcagat aagccttgag accttctttt gtatagttca   6420
tccatgccat gtgtaatccc agcagctgtt acaaactcaa gaaggaccat gtggtctctc   6480
ttttcgttgg gatctttcga aagggcagat tgtgtggaca ggtaatggtt gtctggtaaa   6540
aggacagggc catcgccaat tggagtattt tgttgataat gatcagcgag ttgcacgccg   6600
ccgtcttcga tgttgtggcg ggtcttgaag ttggctttga tgccgttctt ttgcttgtcg   6660
gccatgatgt atacgttgtg ggagttgtag ttgtattcca acttgtggcc gaggatgttt   6720
ccgtcctcct tgaaatcgat tcccttaagc tcgatcctgt tgacgagggt gtctccctca   6780
aacttgactt cagcacgtgt cttgtagttc ccgtcgtcct tgaagaagat ggtcctctcc   6840
tgcacgtatc cctcaggcat ggcgctcttg aagaagtcgt gccgcttcat atgatctggg   6900
tatcttgaaa agcattgaac accataagag aaagtagtga caagtgttgg ccatggaaca   6960
ggtagttttc cagtagtgca aataaattta agggtaagtt ttccgtatgt tgcatcacct   7020
tcaccctctc cactgacaga aaatttgtgc ccattaacat caccatctaa ttcaacaaga   7080
```

-continued

```
attgggacaa ctccagtgaa aagttcttct cctttactca tcgagtaaat atcagacctt   7140
gaagcattag aacgacgaac agtaacatga agcttcccat cttctttaat ctcagcttca   7200
gtttccaaag gttgtcttcc atctaaagac ataatgtcgg aatcaacatg aatcgaaaca   7260
atagatcctg ctgtgtctgg aaactgctcg gagatcaaaa gcttagctcc acggtactca   7320
aagagaaaga gcatgagtgt gtaccaaatg atacactgaa gaacaacgat ttgaaccatg   7380
aggtcgccgg agaaattacc atacatgcct ttgagaagag gtatccccat gactagagtg   7440
ttggggagtg tcgagagaga gaagagagtt atggtccaat ctaaagaacc gttgcggctg   7500
agtttgcacc agaggaagag gagagagagg acaatgactt tctggagaga atctgcggcg   7560
aggaaacgga ggttcatggc gtaagggttg ttagcggcga tgaagtggaa agagaggaga   7620
ggaacggcga agagagcgac gaaacggttt atgccggagc attggtctgg tgtgaagatt   7680
ttccaccatt tgacagagcc gtaagcgagg atcatagcta cgtataacgg aaccatagcc   7740
gtcataacgt ggtagaagtc cgccgccgta atcatggcta tcgttcgtaa atggtgaaaa   7800
ttttcagaaa attgcttttg ctttaaaaga aatgatttaa attgctgcaa tagaagtaga   7860
atgcttgatt gcttgagatt cgtttgtttt gtatatgttg tgttgagaat tctcgagggg   7920
atcctctaga gtcgaggtcc tctccaaatg aaatgaactt ccttatatag aggaagggtc   7980
ttgcgaagga tagtgggatt gtgcgtcatc ccttacgtca gtggagatat cacatcaatc   8040
cacttgcttt gaagacgtgg ttggaacgtc ttctttttcc acgatgctcc tcgtgggtgg   8100
gggtccatct ttgggaccac tgtcggcaga ggcatcttca acgatggcct ttcctttatc   8160
gcaatgatgg catttgtagg agccaccttc cttttccact atcttcacaa taaagtgaca   8220
gatagctggg caatggaatc cgaggaggtt tccggatatt accctttgtt gaaaagtctc   8280
aattgccctt tggtcttctg agactgtatc tttgatattt ttggagtaga caagtgtgtc   8340
gtgctccacc atgttatcac atcaatccac ttgctttgaa gacgtggttg gaacgtcttc   8400
tttttccacg atgctcctcg tgggtggggg tccatctttg ggaccactgt cggcagaggc   8460
atcttcaacg atggcctttc ctttatcgca atgatggcat ttgtaggagc caccttcctt   8520
ttccactatc ttcacaataa agtgacagat agctgggcaa tggaatccga ggaggtttcc   8580
ggatattacc ctttgttgaa aagtctcaat tgccctttgg tcttctgaga ctgtatcttt   8640
gatatttttg gagtagacaa gtgtgtcgtg ctccaccatg ttgatccccg ggtaccgagc   8700
tcgaattcac tggccgtcgt tttacaacgt cgtgactggg aaaaccctgg cgttacccaa   8760
cttaatcgcc ttgcagcaca tccccctttc gccagcccgg actgatgggc tgcctgtatc   8820
gagtggtgat tttgtgccga gctgccggtc ggggagctgt tggctggctg gtggcaggat   8880
atattgtggt gtaaacaaat tgacgcttag acaacttaat aacacattgc ggacgttttt   8940
aatgatcgaa tactaacgtc tctaccagat atcagcttgc atgccggtcg atctagtaac   9000
atagatgaca ccgcgcgcga taatttatcc tagtttgcgc gctatatttt gttttctatc   9060
gcgtattaaa tgtataattg cgggactcta atcataaaaa cccatctcat aaataacgtc   9120
atgcattaca tgttaattat tacatgctta acgtaattca acagaaatta tatgataatc   9180
atcgcaagac cggcaacagg attcaatctt aagaaacttt attgccaaat gtttgaacga   9240
tctgcttgac tctaggggtc atcagatttc ggtgacgggc aggaccggac ggggcggcac   9300
cggcaggctg aagtccagct gccagaaacc cacgtcatgc cagttcccgt gcttgaagcc   9360
ggccgcccgc agcatgccgc ggggggcata tccgagcgcc tcgtgcatgc gcacgctcgg   9420
gtcgttgggc agcccgatga cagcgaccac gctcttgaag ccctgtgcct ccagggactt   9480
```

-continued

```
cagcaggtgg gtgtagagcg tggagcccag tcccgtccgc tggtggcggg gggagacgta    9540
cacggtcgac tcggccgtcc agtcgtaggc gttgcgtgcc ttccaggggc ccgcgtaggc    9600
gatgccggcg acctcgccgt ccacctcggc gacgagccag ggatagcgct cccgcagacg    9660
gacgaggtcg tccgtccact cctgcggttc ctgcggctcg gtacggaagt tgaccgtgct    9720
tgtctcgatg tagtggttga cgatggtgca gaccgccggc atgtccgcct cggtggcacg    9780
gcggatgtcg gccgggcgtc gttctgggct catggtagat cccctcgat cgagttgaga     9840 gtgaatatga gactctaatt ggataccgag gggaatttat ggaacgtcag tggagcattt    9900
ttgacaagaa atatttgcta gctgatagtg accttaggcg acttttgaac gcgcaataat    9960
ggtttctgac gtatgtgctt agctcattaa actccagaaa cccgcggctg agtggctcct   10020
tcaacgttgc ggttctgtca gttccaaacg taaaacggct tgtcccgcgt catcggcggg   10080
ggtcataacg tgactcccct aattctccgc tcatgatcag attgtcgttt cccgccttcg   10140
gtttgggcgc gcccggtctc agaagaccag agggctattg agacttttca acaaagggta   10200
atatcgggaa acctcctcgg attccattgc ccagctatct gtcacttcat cgaaaggaca   10260
gtagaaaagg aagatggctt ctacaaatgc catcattgcg ataaaggaaa ggctatcgtt   10320
caagaatgcc tctaccgaca gtggtcccaa agatggaccc ccacccacga ggaacatcgt   10380
ggaaaaagaa gacgttccaa ccacgtcttc aaagcaagtg gattgatgtg ataacatggt   10440
ggagcacgac actctcgtct actccaagaa tatcaaagat acagtctcag aagaccagag   10500
ggctattgag acttttcaac aaagggtaat atcgggaaac ctcctcggat tccattgccc   10560
agctatctgt cacttcatcg aaaggacagt agaaaaggaa gatggcttct acaaatgcca   10620
tcattgcgat aaaggaaagg ctatcgttca gaatgcctc taccgacagt ggtcccaaag   10680
atggaccccc acccacgagg aacatcgtgg aaaagaaga cgttccaacc acgtcttcaa    10740
agcaagtgga ttgatgtgat atctccactg acgtaaggga tgacgcacaa tcccactatc   10800
cttcgcaaga cccttcctct atataaggaa gttcatttca tttggagagg acctcgagaa   10860
agaggatcca cctgaggatc acaagtttgt acaaaaaagc aggctctgca aggcgattaa   10920
gttgggtaac gccagggttt tcccagtcac gacgttgtaa aacgacggcc agtgaattgt   10980
aatacgactc actatagggc gaattgggta ccgggccccc cctcgaggtc gacggtatcg   11040
ataagcttga tatcgaattc ctgcagccca caaacacacg ctcggacgca tattacacat   11100
gttcatacac ttaatactcg ctgttttgaa ttgatgtttt aggaatatat atgtagaaga   11160
gccatgcctg tgggatattc acaggtcgtg atatgattca attagcttcc gactcattca   11220
tccaaatacc gagtcgccaa aattcaaact agactcgtta aatgaatgaa tgatgcggta   11280
gacaaattgg atcattgatt ctctttgatt atccctcagg catggcgctt ctctcttttg   11340
tattccaatt ttcttgatta atctttcctg cacaaaaaca tgcttgatcc actaagtgac   11400
atatatgctg ccttcgtata tatagttctg gtaaaattaa cattttgggt ttatcttat    11460 ttaaggcatc gccatggggg gatccactag ttctagagcg gccgccaccg cggtggagct   11520
ccagcttttg ttccctttag tgagggttaa ttccgagctt ggcgtaatca tggtcatagc   11580
tgtttcctgt gtgaaattgt tatccgcacc cagctttc                           11618
```

<210> SEQ ID NO 2
<211> LENGTH: 6315
<212> TYPE: DNA
<213> ORGANISM: Artificial Sequence
<220> FEATURE:

<223> OTHER INFORMATION: Vector designated p2GW7,0-PIN8-Venus, for
      expression of the PIN8-Venus construct

<400> SEQUENCE: 2

```
atcaccactt tgtacaagaa agctgaacga gaaacgtaaa atgatataaa tatcaatata      60
ttaaattaga ttttgcataa aaaacagact acataatact gtaaaacaca acatatccag     120
tcactatgtc ataggtccaa tagaaaataa tatgccaaag ttgttggtaa ggcaattagc     180
attccaaata tcaccccagt actaatgatc tccgggtgaa gattatactc ttttgcaaaa     240
acaaatggca ctactccttg aggcaatgct gcctgtaata ttgctacttt gaagagagta     300
cttttaatc tgatgcaata cgcagaagca atcataagag caggtcctaa tacgaacttg      360
agcagcattg ttataatcgc cattttgta ccacatgcta tgatactact ttgtgatgcc      420
atgaacagac ctaagctgaa catggccatt cctaagcctc catcagataa taaatgtatt     480
gatttatcaa tcatctcagg caaattccat cccaatctga aatgtaaagt agcccaaatg     540
attccgatca atgttgcgta tgtatttgga ttgattataa gctttctcca agccttcaat     600
agaatcttca tagttccaac agatcttgtt ctcactattg ctacttcttc ttcgtcctct     660
tcttcttttg gctcgtcctc cttgtacagc tcgtccatgc cgagagtgat cccggcggcg     720
gtcacgaact ccagcaggac catgtgatcg cgcttctcgt tggggtcttt gctcagggcg     780
gactggtagc tcaggtagtg gttgtcgggc agcagcacgg ggccgtcgcc gatggggtg      840
ttctgctggt agtggtcggc gagctgcacg ccgccgtcct cgatgttgtg gcggatcttg     900
aagttggcct tgatgccgtt cttctgcttg tcggcggtga tatagacgtt gtggctgttg     960
tagttgtact ccagcttgtg ccccaggatg ttgccgtcct ccttgaagtc gatgcccttc    1020
agctcgatgc ggttcaccag ggtgtcgccc tcgaacttca cctcggcgcg gtcttgtag    1080
ttgccgtcgt ccttgaagaa gatggtgcgc tcctggacgt agccttcggg catggcggac    1140
ttgaagaagt cgtgctgctt catgtggtcg gggtagcggg cgaagcactg caggccgtag    1200
cccagggtgg tcacgagggt gggccagggc acgggcagct tgccggtggt gcagatcagc    1260
ttcagggtca gcttgccgta ggtggcatcg ccctcgccct cgccggacac gctgaacttg    1320
tggccgttta cgtcgccgtc cagctcgacc aggatgggca ccaccccggt gaacagctcc    1380
tcgcccttgc tcaccattat attagcctct tcctggtcat tgcctgtatg ttctagggaa    1440
gctccagaag atggtaacgc ccttgcggcg ttaagctcga acaaaaagag caagatggtg    1500
taccaaatca agctttgcaa gacaacaatc tgctccaaga tgctcgcagc ttcatctcca    1560
tagatggcac tcaagattgg cattccaaga atgagagtat ttggcaacac cgatatagat    1620
aatccggtta tgacccaacc caattttcct cctcttcctc ctgttggatg ccagaatctt    1680
aaaaccatgg ctaatacaac aacgactaag aatttctgga gaatatcaga gagaatgagt    1740
ttagggctca tcttgaaggg gttgttttca gagattattt gaaaagaaag caagggatg     1800
gagaatttgg ccacgaattt gttgatgcct gcgcattgtt cgggtgagaa gagctttaga    1860
tgtcttgcag agaggaaacc taatgtcatt gagacataga gaggaacagt tgctgaaaca    1920
acatggtaga tatcgagcca ggagatcatc atagtgactg gatatgttgt gttttacagt    1980
attatgtagt ctgttttta tgcaaaatct aatttaatat attgatattt atatcatttt     2040
acgtttctcg ttcagctttt ttgtacaaac ttgtgatatc actagtgcgg ccgcctgcag    2100
gtcgactaga atagtaaatt gtaatgttgt ttgttgtttg ttttgttgtg gtattgttgt    2160
aaaaataccg gagtcctctc caaatgaaat gaacttcctg atatagagga agggtcttgc    2220
```

-continued

```
gaaggatagt gggattgtgc gtcatccctt acgtcagtgg agatatcaca tcaatccact    2280
tgctttgaag acgtggttgg aacgtcttct ttttccacga tgctcctcgt gggtggggt     2340 ccatctttgg gaccactgtc ggcagaggca tcttgaacga tagcctttcc tttatcgcaa    2400
tgatggcatt tgtaggtgcc accttccttt tctactgtcc ttttgatgaa gtgacagata    2460
gctgggcaat ggaatccgag gaggtttccc gatattaccc tttgttgaaa agtctcaata    2520 gcccttggt cttctgagac tgtatctttg atattcttgg agtagacgag agtgtcgtgc     2580
tccaccatgt tgacgaagat tttcttcttg tcattgagtc gtaaaagact ctgtatgaac    2640
tgttcgccag tcttcacggc gagttctgtt agatcctcga tctgaatttt tgactccatg    2700
gcctttgatt cagtaggaac tactttctta gagactccaa tctctattac ttgccttggt    2760
ttatgaagca agccttgaat cgtccatact ggaatagtac ttctgatctt gagaaatata    2820
tctttctctg tgttcttgat gcagttagtc ctgaatcttt tgactgcatc tttaaccttc    2880
ttgggaaggt atttgatctc ctggagatta ttactcgggt agatcgtctt gatgagacct    2940
gccgcgtagg cctctctaac catctgtggg tcagcattct ttctgaaatt gaagaggcta    3000
atcttctcat tatcggtggt gaacatggta tcgtcacctt ctccgtcgaa ctttcttcct    3060
agatcgtaga gatagagaaa gtcgtccatg gtgatctccg gggcaaagga gatcagcttg    3120
gctctagtcg accatatggg agagctccca acgcgttgga tgcatagctt gagtattcta    3180
tagtgtcacc taaatagctt ggcgtaatca tggtcatagc tgtttcctgt gtgaaattgt    3240
tatccgctca caattccaca acatacga gccggaagca taaagtgtaa agcctggggt      3300
gcctaatgag tgagctaact cacattaatt gcgttgcgct cactgcccgc tttccagtcg    3360
ggaaacctgt cgtgccagct gcattaatga atcggccaac gcgcggggag aggcggtttg    3420
cgtattgggc gctcttccgc ttcctcgctc actgactcgc tgcgctcggt cgttcggctg    3480
cggcgagcgg tatcagctca ctcaaaggcg gtaatacggt tatccacaga atcaggggat    3540
aacgcaggaa agaacatgtg agcaaaaggc cagcaaaagg ccaggaaccg taaaaaggcc    3600
gcgttgctgg cgttttttcca taggctccgc cccctgacg agcatcacaa aaatcgacgc    3660
tcaagtcaga ggtggcgaaa cccgacagga ctataaagat accaggcgtt ccccctgga    3720 agctccctcg tgcgctctcc tgttccgacc ctgccgctta ccggatacct gtccgccttt    3780
ctcccttcgg gaagcgtggc gctttctcat agctcacgct gtaggtatct cagttcggtg    3840
taggtcgttc gctccaagct gggctgtgtg cacgaacccc ccgttcagcc cgaccgctgc    3900
gccttatccg gtaactatcg tcttgagtcc aacccggtaa gacacgactt atcgccactg    3960
gcagcagcca ctggtaacag gattagcaga gcgaggtatg taggcggtgc tacagagttc    4020
ttgaagtggt ggcctaacta cggctacact agaagaacag tatttggtat ctgcgctctg    4080
ctgaagccag ttaccttcgg aaaaagagtt ggtagctctt gatccggcaa acaaaccacc    4140
gctggtagcg gtggtttttt tgtttgcaag cagcagatta cgcgcagaaa aaaggatct    4200 caagaagatc ctttgatctt ttctacgggg tctgacgctc agtggaacga aaactcacgt    4260
taagggattt tggtcatgag attatcaaaa aggatcttca cctagatcct tttaaattaa    4320
aaatgaagtt ttaaatcaat ctaaagtata tatgagtaaa cttggtctga cagttaccaa    4380
tgcttaatca gtgaggcacc tatctcagcg atctgtctat ttcgttcatc catagttgcc    4440 tgactcccccg tcgtgtagat aactacgata cgggagggct taccatctgg ccccagtgct    4500
gcaatgatac cgcgagaccc acgctcaccg gctccagatt tatcagcaat aaaccagcca    4560
gccggaaggg ccgagcgcag aagtggtcct gcaactttat ccgcctccat ccagtctatt    4620
```

-continued

```
aattgttgcc gggaagctag agtaagtagt tcgccagtta atagtttgcg caacgttgtt      4680
gccattgcta caggcatcgt ggtgtcacgc tcgtcgtttg gtatggcttc attcagctcc      4740
ggttcccaac gatcaaggcg agttacatga tcccccatgt tgtgcaaaaa agcggttagc      4800
tccttcggtc ctccgatcgt tgtcagaagt aagttggccg cagtgttatc actcatggtt      4860
atggcagcac tgcataattc tcttactgtc atgccatccg taagatgctt ttctgtgact      4920
ggtgagtact caaccaagtc attctgagaa tagtgtatgc ggcgaccgag ttgctcttgc      4980
ccggcgtcaa tacgggataa taccgcgcca catagcagaa ctttaaaagt gctcatcatt      5040
ggaaaacgtt cttcggggcg aaaactctca aggatcttac cgctgttgag atccagttcg      5100
atgtaaccca ctcgtgcacc caactgatct tcagcatctt ttactttcac cagcgtttct      5160
gggtgagcaa aaacaggaag gcaaaatgcc gcaaaaaagg gaataagggc gacacggaaa      5220
tgttgaatac tcatactctt cctttttcaa tattattgaa gcatttatca gggttattgt      5280
ctcatgagcg gatacatatt tgaatgtatt tagaaaaata aacaaatagg ggttccgcgc      5340
acatttcccc gaaaagtgcc acctgatgcg gtgtgaaata ccgcacagat gcgtaaggag      5400
aaaataccgc atcaggaaat tgtaagcgtt aatattttgt taaaattcgc gttaaatttt      5460
tgttaaatca gctcattttt taaccaatag gccgaaatcg gcaaaatccc ttataaatca      5520
aaagaataga ccgagatagg gttgagtgtt gttccagttt ggaacaagag tccactatta      5580
aagaacgtgg actccaacgt caaagggcga aaaccgtctg atcagggcga tggcccacta      5640
cgtgaaccat cacccctaatc aagttttttg gggtcgaggt gccgtaaagc actaaatcgg      5700
aaccctaaag ggagccccccg atttagagct tgacggggaa agccggcgaa cgtggcgaga      5760
aaggaaggga agaaagcgaa aggagcgggc gctagggcgc tggcaagtgt agcggtcacg      5820
ctgcgcgtaa ccaccacacc cgccgcgctt aatgcgccgc tacagggcgc gtccattcgc      5880
cattcaggct gcgcaactgt tgggaagggc gatcggtgcg ggcctcttcg ctattacgcc      5940
agctggcgaa agggggatgt gctgcaaggc gattaagttg ggtaacgcca gggttttccc      6000
agtcacgacg ttgtaaaacg acggccagtg aattgtaata cgactcacta taggggcgaat      6060 tgggcccgac gtcgcatgcc tgcaggtcac tggattttgg ttttaggaat tagaaatttt      6120
attgatagaa gtattttaca aatacaaata catactaagg gtttcttata tgctcaacac      6180
atgagcgaaa ccctataaga cccctaattc ccttatctgg gaactactca cacattattc      6240
tggagaaaaa tagagagaga tagatttgta gagagagact ggtgattttt gcggactcta      6300
gcatggccgc gggat                                                      6315
```

<210> SEQ ID NO 3
<211> LENGTH: 7957
<212> TYPE: DNA
<213> ORGANISM: Artificial Sequence
<220> FEATURE:
<223> OTHER INFORMATION: Vector designated pAM-PAT-AtPIN1-Venus, for
      expression of the PIN1-Venus construct

<400> SEQUENCE: 3

```
ttgtacaaag tggtgatcct ccgttccatg ggctagaagc ttgttgagaa ttcatcgccc        60
gggactgggt taacttccga tcgattctag actagttcta gagtccgcaa aaatcaccag      120
tctctctcta caaatctatc tctctctatt tttctccaga ataatgtgtg agtagttccc      180
agataaggga attagggttc ttatagggtt tcgctcatgt gttgagcata taagaaaccc      240
ttagtatgta tttgtatttg taaaatactt ctatcaataa aatttctaat tcctaaaacc      300
```

```
aaaatccagt gaccgggcgg ccgccaccgc ggtggagggg gatcagattg tcgtttcccg    360
ccttcagttt aaactatcag tgtttgacag gatatattgg cgggtaaacc taagagaaaa    420
gagcgtttat tagaataatc ggatatttaa aagggcgtga aaaggtttat ccgttcgtcc    480
atttgtatgt gtacatcacc gacgagcaag gcaagaccga gcgcctttcc gacgctcacc    540
gggctggttg ccctcgccgc tgggctggcg gccgtctatg gccctgcaaa cgcgccagaa    600
acgccgtcga agccgtgtgc gagacaccgg ccgccggcgt tgtggatacc tcgcggaaaa    660
cttggccctc actgacagat gaggggcgga cgttgacact tgaggggccg actcacccgg    720
cgcggcgttg acagatgagg ggcaggctcg atttcggccg cgacgtgga gctggccagc    780 ctcgcaaatc ggcgaaaacg cctgatttta cgcgagtttc ccacagatga tgtggacaag    840
cctggggata agtgccctgc ggtattgaca cttgaggggc gcgactactg acagatgagg    900
ggcgcgatcc ttgacacttg agggcagag tgctgacaga tgaggggcgc acctattgac    960
atttgagggg ctgtccacag gcagaaaatc cagcattgc aagggtttcc gcccgttttt   1020
cggccaccgc taacctgtct tttaacctgc ttttaaacca atatttataa accttgtttt   1080
taaccagggc tgcgccctgt gcgcgtgacc gcgcacgccg aagggggtg cccccccttc   1140 tcgaaccctc ccggcccgct aacgcgggcc tcccatcccc caggggctg cgcccctcgg   1200 ccgcgaacgg cctcacccca aaaatggcag cgctggcagt ccttgccatt gccgggatcg   1260
gggcagtaac gggatgggcg atcagcccga caagctaccc ctatttgttt attttttctaa   1320 atacattcaa atatgtatcc gctcatgaga caataaccct gataaatgct tcaataatat   1380 tgaaaagga agagtatgag tattcaacat ttccgtgtcg cccttattcc cttttttgcg   1440 gcatttgcc ttcctgtttt tgctcaccca gaaacgctgg tgaaagtaaa agatgctgaa   1500
gatcagttgg gtgcacgagt gggttacatc gaactggatc tcaacagcgg taagatcctt   1560
gagagttttc gccccgaaga acgttttcca atgatgagca cttttaaagt tctgctatgt   1620
ggcgcggtat tatcccgtat tgacgccggg caagagcaac tcggtcgccg catacactat   1680
tctcagaatg acttggttga gtactcacca gtcacagaaa agcatcttac ggatggcatg   1740
acagtaagag aattatgcag tgctgccata accatgagtg ataacactgc ggccaactta   1800
cttctgacaa cgatcggagg accgaaggag ctaaccgctt ttttgcacaa catgggggat   1860
catgtaactc gccttgatcg ttgggaaccg gagctgaatg aagccatacc aaacgacgag   1920
cgtgacacca cgatgcctgt agcaatggca acaacgttgc gcaaactatt aactggcgaa   1980
ctacttactc tagcttcccg gcaacaatta atagactgga tggaggcgga taaagttgca   2040
ggaccacttc tgcgctcggc ccttccggct ggctggttta ttgctgataa atctggagcc   2100
ggtgagcgtg gtctcgcgg tatcattgca gcactgggc cagatggtaa gccctcccgt   2160
atcgtagtta tctacacgac ggggagtcag gcaactatgg atgaacgaaa tagacagatc   2220
gctgagatag gtgcctcact gattaagcat tggtaactgt cagaccaagt ttactcatat   2280
atactttaga ttgatttaaa acttcatttt taatttaaaa ggatctaggt gaagatcctt   2340
tttgataatc tcatgaccaa aatcccttaa cgtgagtttt cgttccactg agcgtcagac   2400
cccgtagaaa agatcaaagg atcttcttga tccttttt ttctgcgcgt aatctgctgc   2460
ttgcaaacaa aaaaaccacc gctaccagcg gtggtttgtt tgccggatca agagctacca   2520 actcttttc cgaaggtaac tggcttcagc agagcgcaga taccaaatac tgtccttcta   2580
gtgtagccgt agttaggcca ccacttcaag aactctgtag caccgcctac atacctcgct   2640
```

```
ctgctaatcc tgttaccagt ggctgctgcc agtggcgata agtcgtgtct taccgggttg    2700
gactcaagac gatagttacc ggataaggcg cagcggtcgg gctgaacggg gggttcgtgc    2760
acacagccca gcttggagcg aacgacctac accgaactga gatacctaca gcgtgagcta    2820
tgagaaagcg ccacgcttcc cgaagggaga aaggcggaca ggtatccggt aagcggcagg    2880
gtcggaacag gagagcgcac gagggagctt ccaggrggaa acgcctggta tctttatagt    2940
cctgtcgggt ttcgccacct ctgacttgag cgtcgatttt tgtgatgctc gtcaggrggg    3000
cggagcctat ggaaaaacgc cagcaacgcg ccttttttac ggttcctggc cttttgctgg    3060
ccttttgctc acatggactc tagctagagg atcacaggca gcaacgctct gtcatcgtta    3120
caatcaacat gctaccctcc gcgagatcat ccgtgtttca aacccggcag cttagttgcc    3180
gttcttccga atagcatcgg taacatgagc aaagtctgcc gccttacaac ggctctcccg    3240
ctgacgccgt cccggactga tgggctgcct gtatcgagtg gtgattttgt gccgagctgc    3300
cggtcgggga gctgttggct ggctggtggc aggatatatt gtggtgtaaa caaattgacg    3360
cttagacaac ttaataacac attgcggacg ttttaatga tcgaatacta acgtctctac    3420
cagatatcag cttgcatgcc ggtcgatcta gtaacataga tgacaccgcg cgcgataatt    3480
tatcctagtt tgcgcgctat attttgtttt ctatcgcgta ttaaatgtat aattgcggga    3540
ctctaatcat aaaaacccat ctcataaata acgtcatgca ttacatgtta attattacat    3600
gcttaacgta attcaacaga aattatatga taatcatcgc aagaccggca acaggattca    3660
atcttaagaa actttattgc caaatgtttg aacgatctgc ttgactctag ggtcatcag    3720 atttcggtga cgggcaggac cggacggggc ggcaccggca ggctgaagtc cagctgccag    3780
aaacccacgt catgccagtt cccgtgcttg aagccggccg cccgcagcat gccgcggggg    3840
gcatatccga gcgcctcgtg catgcgcacg ctcgggtcgt tgggcagccc gatgacagcg    3900
accacgctct tgaagccctg tgcctccagg gacttcagca ggtgggtgta gagcgtggag    3960
cccagtcccg tccgctggtg gcggggggag acgtacacgg tcgactcggc cgtccagtcg    4020
taggcgttgc gtgccttcca ggggcccgcg taggcgatgc cggcgacctc gccgtccacc    4080
tcggcgacga gccagggata gcgctcccgc agacggacga ggtcgtccgt ccactcctgc    4140
ggttcctgcg gctcggtacg gaagttgacc gtgcttgtct cgatgtagtg gttgacgatg    4200
gtgcagaccg ccggcatgtc cgcctcggtg gcacggcgga tgtcggccgg gcgtcgttct    4260
gggctcatgg tagatccccc tcgatcgagt tgagagtgaa tatgagactc taattggata    4320
ccgaggggaa tttatggaac gtcagtggag cattttttgac aagaaatatt tgctagctga    4380
tagtgacctt aggcgacttt tgaacgcgca ataatggttt ctgacgtatg tgcttagctc    4440
attaaactcc agaaacccgc ggctgagtgg ctccttcaac gttgcggttc tgtcagttcc    4500
aaacgtaaaa cggcttgtcc cgcgtcatcg gcggrggtca taacgtgact cccttaattc    4560
tccgctcatg atcagattgt cgtttcccgc cttcggtttg ggcgcgcccg gtctcagaag    4620
accagagggc tattgagact tttcaacaaa gggtaatatc gggaaacctc ctcggattcc    4680
attgcccagc tatctgtcac ttcatcgaaa ggacagtaga aaaggaagat ggcttctaca    4740
aatgccatca ttgcgataaa ggaaaggcta tcgttcaaga atgcctctac cgacagtggt    4800
cccaaagatg gacccccacc cacgaggaac atcgtggaaa aagaagacgt tccaaccacg    4860
tcttcaaagc aagtggattg atgtgataac atggtggagc acgacactct cgtctactcc    4920
aagaatatca aagatacagt ctcagaagac cagagggcta ttgagctttt caacaaagg    4980 gtaatatcgg gaaacctcct cggattccat tgcccagcta tctgtcactt catcgaaagg    5040
```

```
acagtagaaa aggaagatgg cttctacaaa tgccatcatt gcgataaagg aaaggctatc   5100
gttcaagaat gcctctaccg acagtggtcc caaagatgga cccccaccca cgaggaacat   5160
cgtggaaaaa gaagacgttc caaccacgtc ttcaaagcaa gtggattgat gtgatatctc   5220
cactgacgta agggatgacg cacaatccca ctatccttcg caagacccct cctctatata   5280
aggaagttca tttcatttgg agaggacctc gagaaagagg atccacctga ggatcacaag   5340
tttgtacaaa aaagcaggct atgattacgg cggcggactt ctaccacgtt atgacggcta   5400
tggttccgtt atacgtagct atgatcctcg cttacggctc tgtcaaatgg tggaaaatct   5460
tcacaccaga ccaatgctcc ggcataaacc gtttcgtcgc tctcttcgcc gttcctctcc   5520
tctctttcca cttcatcgcc gctaacaacc cttacgccat gaacctccgt ttcctcgccg   5580
cagattctct ccagaaagtc attgtcctct ctctcctctt cctctggtgc aaactcagcc   5640
gcaacggttc tttagattgg accataactc tcttctctct ctcgacactc cccaacactc   5700
tagtcatggg gatacctctt ctcaaaggca tgtatggtaa tttctccggc gacctcatgg   5760
ttcaaatcgt tgttcttcag tgtatcattt ggtacacact catgctcttt ctctttgagt   5820 accgtgggagc taagcttttg atctccgagc agtttccaga cacagcagga tctattgttt   5880
cgattcatgt tgattccgac attatgtctt tagatggaag acaacctttg gaaactgaag   5940
ctgagattaa agaagatggg aagcttcatg ttactgttcg tcgttctaat gcttcaaggt   6000 ctgatatttta ctcgatggtg agcaagggcg aggagctgtt caccggggtg gtgcccatcc   6060
tggtcgagct ggacggcgac gtaaacggcc acaagttcag cgtgtccggc gagggcgagg   6120
gcgatgccac ctacggcaag ctgaccctga agctgatctg caccaccggc aagctgcccg   6180
tgccctggcc cacccctgtg accacctgg gctacggcct gcagtgcttc gcccgctacc   6240
ccgaccacat gaagcagcac gacttcttca gtccgccat gcccgaaggc tacgtccagg   6300
agcgcaccat cttcttcaag gacgacggca actacaagac ccgcgccgag gtgaagttcg   6360
agggcgacac cctggtgaac cgcatcgagc tgaagggcat cgacttcaag gaggacggca   6420
acatcctggg gcacaagctg gagtacaact acaacagcca caacgtctat atcaccgccg   6480
acaagcagaa gaacggcatc aaggccaact tcaagatccg ccacaacatc gaggacggcg   6540
gcgtgcagct cgccgaccac taccagcaga cacccccat cggcgacggc cccgtgctgc   6600
tgcccgacaa ccactacctg agctaccagt ccgccctgag caaagacccc aacgagaagc   6660
gcgatcacat ggtcctgctg gagttcgtga ccgccgccgg gatcactctc ggcatggacg   6720
agctgtacaa gagaaggtct caaggcttat ctgcgacacc tagaccttcg aatctaacca   6780
acgctgagat atattcgctt cagagttcaa gaaacccaac gccacgtggc tctagtttta   6840
atcatactga tttttactcg atgatggctt ctggtggtgg tcgaactct aactttggtc   6900 ctggagaagc tgtgtttggt tctaaaggtc ctactccgag accttccaac tacgaagaag   6960
acggtggtcc tgctaaaccg acggctgctg gaactgctgc tggagctggg aggtttcatt   7020
atcaatctgg aggaagtggt ggcggtggag gagcgcatta tccggcgccg aacccaggga   7080
tgttttcgcc caacactggc ggtggtggag gcacggcggc gaaaggaaac gctccggtgg   7140
ttggtgggaa aagacaagac ggaaacggaa gagatcttca catgtttgtg tggagctcaa   7200
gtgcttcgcc ggtctcagat gtgttcggcg gtggaggagg aaaccaccac gccgattact   7260
ccaccgctac gaacgatcat caaaaggacg ttaagatctc tgtacctcag gggaatagta   7320
acgacaacca gtacgtggag agggaagagt ttagtttcgg taacaaagac gatgatagca   7380
```

```
aagtattggc aacggacggt gggaacaaca taagcaacaa aacgacgcag gctaaggtga    7440
tgccaccaac aagtgtgatg acaagactca ttctcattat ggtttggagg aaacttattc    7500
gtaatcccaa ctcttactcc agtttattcg gcatcacctg gtccctcatt tccttcaagt    7560
ggaacattga aatgccagct cttatagcaa agtctatctc catactctca gatgcaggtc    7620
taggcatggc tatgttcagt cttgggttgt tcatggcgtt aaacccaaga ataatagctt    7680
gtggaaacag aagagcagct tttgcggcgg ctatgagatt tgtcgttgga cctgccgtca    7740
tgctcgttgc ttcttatgcc gttggcctcc gtggcgtcct cctccatgtt gccattatcc    7800
aggcagcttt gccgcaagga atagtaccgt ttgtgtttgc caaagagtat aatgtgcatc    7860
ctgacattct tagcactgcg gtgatatttg ggatgttgat cgcgttgccc ataactcttc    7920
tctactacat tctcttgggt ctatgaaccc agctttc                             7957

<210> SEQ ID NO 4
<211> LENGTH: 21
<212> TYPE: DNA
<213> ORGANISM: Artificial Sequence
<220> FEATURE:
<223> OTHER INFORMATION: artificial microRNA P35

<400> SEQUENCE: 4
tgttgggcga aaacatccgt g                                                21

<210> SEQ ID NO 5
<211> LENGTH: 21
<212> TYPE: DNA
<213> ORGANISM: Artificial Sequence
<220> FEATURE:
<223> OTHER INFORMATION: passenger strand P35* of artificial microRNA
      P35

<400> SEQUENCE: 5
caaggatgtt ttcccccaac t                                                21

<210> SEQ ID NO 6
<211> LENGTH: 21
<212> TYPE: DNA
<213> ORGANISM: Artificial Sequence
<220> FEATURE:
<223> OTHER INFORMATION: mock artificial microRNA

<400> SEQUENCE: 6
tatcataaga gcaggtcctg a                                                21

<210> SEQ ID NO 7
<211> LENGTH: 21
<212> TYPE: DNA
<213> ORGANISM: Artificial Sequence
<220> FEATURE:
<223> OTHER INFORMATION: passenger strand mock* of artificial microRNA
      mock

<400> SEQUENCE: 7
tccggacctg ctcatatgat t                                                21

<210> SEQ ID NO 8
<211> LENGTH: 21
<212> TYPE: DNA
<213> ORGANISM: Artificial Sequence
<220> FEATURE:
<223> OTHER INFORMATION: artificial microRNA P34

<400> SEQUENCE: 8
```

```
taacggttta tgccgcagcg t                                              21

<210> SEQ ID NO 9
<211> LENGTH: 21
<212> TYPE: DNA
<213> ORGANISM: Artificial Sequence
<220> FEATURE:
<223> OTHER INFORMATION: passenger strand P34* of artificial microRNA
      P34

<400> SEQUENCE: 9
acactgcggc ataccgtt t                                                21

<210> SEQ ID NO 10
<211> LENGTH: 21
<212> TYPE: DNA
<213> ORGANISM: Artificial Sequence
<220> FEATURE:
<223> OTHER INFORMATION: artificial microRNA P33

<400> SEQUENCE: 10
tacgatttga accatgaggc c                                              21

<210> SEQ ID NO 11
<211> LENGTH: 21
<212> TYPE: DNA
<213> ORGANISM: Artificial Sequence
<220> FEATURE:
<223> OTHER INFORMATION: passenger strand P33* of artificial microRNA
      P33

<400> SEQUENCE: 11
ggactcatgg ttctaatcgt t                                              21

<210> SEQ ID NO 12
<211> LENGTH: 21
<212> TYPE: DNA
<213> ORGANISM: Artificial Sequence
<220> FEATURE:
<223> OTHER INFORMATION: artificial microRNA GFP-11

<400> SEQUENCE: 12
ttgacttcag cacgtgtctt g                                              21

<210> SEQ ID NO 13
<211> LENGTH: 21
<212> TYPE: DNA
<213> ORGANISM: Artificial Sequence
<220> FEATURE:
<223> OTHER INFORMATION: passenger strand GFP-11* of artificial microRNA
      GFP-11

<400> SEQUENCE: 13
cacgacacgt gctcaagtca t                                              21

<210> SEQ ID NO 14
<211> LENGTH: 21
<212> TYPE: DNA
<213> ORGANISM: Artificial Sequence
<220> FEATURE:
<223> OTHER INFORMATION: artificial microRNA P32

<400> SEQUENCE: 14
tttgggcgaa aacatccctg c                                              21
```

-continued

```
<210> SEQ ID NO 15
<211> LENGTH: 21
<212> TYPE: DNA
<213> ORGANISM: Artificial Sequence
<220> FEATURE:
<223> OTHER INFORMATION: passenger strand P32* of artificial microRNA
      P32

<400> SEQUENCE: 15
gccgggatgt tttggcccaa t                                              21

<210> SEQ ID NO 16
<211> LENGTH: 21
<212> TYPE: DNA
<213> ORGANISM: Artificial Sequence
<220> FEATURE:
<223> OTHER INFORMATION: artificial microRNA GFP-10

<400> SEQUENCE: 16
tgatcagcga gttgcacgcc g                                              21

<210> SEQ ID NO 17
<211> LENGTH: 21
<212> TYPE: DNA
<213> ORGANISM: Artificial Sequence
<220> FEATURE:
<223> OTHER INFORMATION: passenger strand GFP-10* of artificial microRNA
      GFP-10

<400> SEQUENCE: 17
cgacgtgcaa ctccctgatc t                                              21

<210> SEQ ID NO 18
<211> LENGTH: 21
<212> TYPE: DNA
<213> ORGANISM: Artificial Sequence
<220> FEATURE:
<223> OTHER INFORMATION: artificial microRNA P31

<400> SEQUENCE: 18
tttaccgaaa ctaaactgct c                                              21

<210> SEQ ID NO 19
<211> LENGTH: 21
<212> TYPE: DNA
<213> ORGANISM: Artificial Sequence
<220> FEATURE:
<223> OTHER INFORMATION: passenger strand P31*of artificial microRNA P31

<400> SEQUENCE: 19
gaacagttta gttacggtaa t                                              21

<210> SEQ ID NO 20
<211> LENGTH: 21
<212> TYPE: DNA
<213> ORGANISM: Artificial Sequence
<220> FEATURE:
<223> OTHER INFORMATION: artificial microRNA GFP-9

<400> SEQUENCE: 20
ttgtattcca acttgtggcc g                                              21

<210> SEQ ID NO 21
<211> LENGTH: 21
<212> TYPE: DNA
<213> ORGANISM: Artificial Sequence
<220> FEATURE:
```

<223> OTHER INFORMATION: passenger strand GFP-9* of artificial microRNA
      GFP-9

<400> SEQUENCE: 21
cgaccacaag ttgcaataca t                                              21

<210> SEQ ID NO 22
<211> LENGTH: 21
<212> TYPE: DNA
<213> ORGANISM: Artificial Sequence
<220> FEATURE:
<223> OTHER INFORMATION: artificial microRNA P30

<400> SEQUENCE: 22
tatgacggca ggtcgaacga g                                              21

<210> SEQ ID NO 23
<211> LENGTH: 21
<212> TYPE: DNA
<213> ORGANISM: Artificial Sequence
<220> FEATURE:
<223> OTHER INFORMATION: passenger strand P30* of artificial microRNA
      P30

<400> SEQUENCE: 23
ctagttcgac ctggcgtcat t                                              21

<210> SEQ ID NO 24
<211> LENGTH: 21
<212> TYPE: DNA
<213> ORGANISM: Artificial Sequence
<220> FEATURE:
<223> OTHER INFORMATION: artificial microRNA GFP-7

<400> SEQUENCE: 24
ttaatgatca gcgagttgca c                                              21

<210> SEQ ID NO 25
<211> LENGTH: 21
<212> TYPE: DNA
<213> ORGANISM: Artificial Sequence
<220> FEATURE:
<223> OTHER INFORMATION: passenger strand GFP-7* of artificial microRNA
      GFP-7

<400> SEQUENCE: 25
gtacaactcg ctgttcatta t                                              21

<210> SEQ ID NO 26
<211> LENGTH: 21
<212> TYPE: DNA
<213> ORGANISM: Artificial Sequence
<220> FEATURE:
<223> OTHER INFORMATION: artificial microRNA P29

<400> SEQUENCE: 26
taaattacca tacatgcctt t                                              21

<210> SEQ ID NO 27
<211> LENGTH: 21
<212> TYPE: DNA
<213> ORGANISM: Artificial Sequence
<220> FEATURE:
<223> OTHER INFORMATION: passenger strand P29* of artificial microRNA
      P29

<400> SEQUENCE: 27

```
aacggcatgt atgctaattt t                                              21

<210> SEQ ID NO 28
<211> LENGTH: 21
<212> TYPE: DNA
<213> ORGANISM: Artificial Sequence
<220> FEATURE:
<223> OTHER INFORMATION: artificial microRNA GFP-6

<400> SEQUENCE: 28
ttctggtaaa aggacagggc c                                              21

<210> SEQ ID NO 29
<211> LENGTH: 21
<212> TYPE: DNA
<213> ORGANISM: Artificial Sequence
<220> FEATURE:
<223> OTHER INFORMATION: passenger strand GFP-6* of artificial microRNA
      GFP-6

<400> SEQUENCE: 29
ggacctgtcc tttaaccaga t                                              21

<210> SEQ ID NO 30
<211> LENGTH: 21
<212> TYPE: DNA
<213> ORGANISM: Artificial Sequence
<220> FEATURE:
<223> OTHER INFORMATION: artificial microRNA P28

<400> SEQUENCE: 30
tttaaaacta gagcgacgcg g                                              21

<210> SEQ ID NO 31
<211> LENGTH: 21
<212> TYPE: DNA
<213> ORGANISM: Artificial Sequence
<220> FEATURE:
<223> OTHER INFORMATION: passenger strand P28* of artificial microRNA
      P28

<400> SEQUENCE: 31
ccacgtcgct ctacttttaa t                                              21

<210> SEQ ID NO 32
<211> LENGTH: 21
<212> TYPE: DNA
<213> ORGANISM: Artificial Sequence
<220> FEATURE:
<223> OTHER INFORMATION: artificial microRNA P27

<400> SEQUENCE: 32
tataatgaaa cctcccaggt c                                              21

<210> SEQ ID NO 33
<211> LENGTH: 21
<212> TYPE: DNA
<213> ORGANISM: Artificial Sequence
<220> FEATURE:
<223> OTHER INFORMATION: passenger strand P27* of artificial microRNA
      P27

<400> SEQUENCE: 33
gaactgggag gttacattat t                                              21
```

-continued

```
<210> SEQ ID NO 34
<211> LENGTH: 21
<212> TYPE: DNA
<213> ORGANISM: Artificial Sequence
<220> FEATURE:
<223> OTHER INFORMATION: artificial microRNA P62

<400> SEQUENCE: 34
ttgaagtgga aagagacgac t                                            21

<210> SEQ ID NO 35
<211> LENGTH: 21
<212> TYPE: DNA
<213> ORGANISM: Artificial Sequence
<220> FEATURE:
<223> OTHER INFORMATION: passenger strand P62* of artificial microRNA
      P62

<400> SEQUENCE: 35
agccgtctct ttcgacttca t                                            21

<210> SEQ ID NO 36
<211> LENGTH: 21
<212> TYPE: DNA
<213> ORGANISM: Artificial Sequence
<220> FEATURE:
<223> OTHER INFORMATION: artificial microRNA P26

<400> SEQUENCE: 36
tatgattaaa actacagccg c                                            21

<210> SEQ ID NO 37
<211> LENGTH: 21
<212> TYPE: DNA
<213> ORGANISM: Artificial Sequence
<220> FEATURE:
<223> OTHER INFORMATION: passenger strand P26* of artificial microRNA
      P26

<400> SEQUENCE: 37
gcagctgtag tttaaatcat t                                            21

<210> SEQ ID NO 38
<211> LENGTH: 21
<212> TYPE: DNA
<213> ORGANISM: Artificial Sequence
<220> FEATURE:
<223> OTHER INFORMATION: artificial microRNA P61

<400> SEQUENCE: 38
tactgaacat agccatgcct a                                            21

<210> SEQ ID NO 39
<211> LENGTH: 21
<212> TYPE: DNA
<213> ORGANISM: Artificial Sequence
<220> FEATURE:
<223> OTHER INFORMATION: passenger strand P61* of artificial microRNA
      P61

<400> SEQUENCE: 39
taagcatggc tatcttcagt t                                            21

<210> SEQ ID NO 40
<211> LENGTH: 21
<212> TYPE: DNA
<213> ORGANISM: Artificial Sequence
```

```
<220> FEATURE:
<223> OTHER INFORMATION: artificial microRNA P25

<400> SEQUENCE: 40
ttataacgga accataggcc t                                         21

<210> SEQ ID NO 41
<211> LENGTH: 21
<212> TYPE: DNA
<213> ORGANISM: Artificial Sequence
<220> FEATURE:
<223> OTHER INFORMATION: passenger strand P25* of artificial microRNA
      P25

<400> SEQUENCE: 41
agacctatgg ttcggttata t                                         21

<210> SEQ ID NO 42
<211> LENGTH: 21
<212> TYPE: DNA
<213> ORGANISM: Artificial Sequence
<220> FEATURE:
<223> OTHER INFORMATION: artificial microRNA P60

<400> SEQUENCE: 42
ttccggagca ttggtcggga g                                         21

<210> SEQ ID NO 43
<211> LENGTH: 21
<212> TYPE: DNA
<213> ORGANISM: Artificial Sequence
<220> FEATURE:
<223> OTHER INFORMATION: passenger strand P60* of artificial microRNA
      P60

<400> SEQUENCE: 43
ctaccgacca atggtccgga t                                         21

<210> SEQ ID NO 44
<211> LENGTH: 21
<212> TYPE: DNA
<213> ORGANISM: Artificial Sequence
<220> FEATURE:
<223> OTHER INFORMATION: artificial microRNA P24

<400> SEQUENCE: 44
tccaaagtta gagttgcgac g                                         21

<210> SEQ ID NO 45
<211> LENGTH: 21
<212> TYPE: DNA
<213> ORGANISM: Artificial Sequence
<220> FEATURE:
<223> OTHER INFORMATION: passenger strand P24* of artificial microRNA
      P24

<400> SEQUENCE: 45
cgccgcaact ctatctttgg t                                         21

<210> SEQ ID NO 46
<211> LENGTH: 21
<212> TYPE: DNA
<213> ORGANISM: Artificial Sequence
<220> FEATURE:
<223> OTHER INFORMATION: artificial microRNA P59

<400> SEQUENCE: 46
```
ttgaagtgga aagacaggac t                                              21

<210> SEQ ID NO 47
<211> LENGTH: 21
<212> TYPE: DNA
<213> ORGANISM: Artificial Sequence
<220> FEATURE:
<223> OTHER INFORMATION: passenger strand P59* of artificial microRNA
      P59

<400> SEQUENCE: 47
agccctgtct ttcgacttca t                                              21

<210> SEQ ID NO 48
<211> LENGTH: 21
<212> TYPE: DNA
<213> ORGANISM: Artificial Sequence
<220> FEATURE:
<223> OTHER INFORMATION: artificial microRNA P23

<400> SEQUENCE: 48
tgattacgaa taagtttcct c                                              21

<210> SEQ ID NO 49
<211> LENGTH: 21
<212> TYPE: DNA
<213> ORGANISM: Artificial Sequence
<220> FEATURE:
<223> OTHER INFORMATION: passenger strand P23* of artificial microRNA
      P23

<400> SEQUENCE: 49
gaagaaactt attggtaatc t                                              21

<210> SEQ ID NO 50
<211> LENGTH: 21
<212> TYPE: DNA
<213> ORGANISM: Artificial Sequence
<220> FEATURE:
<223> OTHER INFORMATION: artificial microRNA P58

<400> SEQUENCE: 50
tgtcatcaca cttgttggcg g                                              21

<210> SEQ ID NO 51
<211> LENGTH: 21
<212> TYPE: DNA
<213> ORGANISM: Artificial Sequence
<220> FEATURE:
<223> OTHER INFORMATION: passenger strand P58* of artificial microRNA
      P58

<400> SEQUENCE: 51
ccaccaacaa gtgagatgac t                                              21

<210> SEQ ID NO 52
<211> LENGTH: 21
<212> TYPE: DNA
<213> ORGANISM: Artificial Sequence
<220> FEATURE:
<223> OTHER INFORMATION: artificial microRNA P22

<400> SEQUENCE: 52
ttgatgccga ataaactgca g                                              21

```
<210> SEQ ID NO 53
<211> LENGTH: 21
<212> TYPE: DNA
<213> ORGANISM: Artificial Sequence
<220> FEATURE:
<223> OTHER INFORMATION: passenger strand P22* of artificial microRNA
      P22

<400> SEQUENCE: 53
ctacagttta ttccgcatca t                                              21

<210> SEQ ID NO 54
<211> LENGTH: 21
<212> TYPE: DNA
<213> ORGANISM: Artificial Sequence
<220> FEATURE:
<223> OTHER INFORMATION: artificial microRNA P57

<400> SEQUENCE: 54
tggacggcga agacggcgac a                                              21

<210> SEQ ID NO 55
<211> LENGTH: 21
<212> TYPE: DNA
<213> ORGANISM: Artificial Sequence
<220> FEATURE:
<223> OTHER INFORMATION: passenger strand P57* of artificial microRNA
      P57

<400> SEQUENCE: 55
tgccgccgtc ttccccgtcc t                                              21

<210> SEQ ID NO 56
<211> LENGTH: 21
<212> TYPE: DNA
<213> ORGANISM: Artificial Sequence
<220> FEATURE:
<223> OTHER INFORMATION: artificial microRNA P21

<400> SEQUENCE: 56
ttataacgga accatagccc t                                              21

<210> SEQ ID NO 57
<211> LENGTH: 21
<212> TYPE: DNA
<213> ORGANISM: Artificial Sequence
<220> FEATURE:
<223> OTHER INFORMATION: passenger strand P21* of artificial microRNA
      P21

<400> SEQUENCE: 57
agagctatgg ttcggttata t                                              21

<210> SEQ ID NO 58
<211> LENGTH: 21
<212> TYPE: DNA
<213> ORGANISM: Artificial Sequence
<220> FEATURE:
<223> OTHER INFORMATION: artificial microRNA P56

<400> SEQUENCE: 58
tggaaagaga ggagtgggac g                                              21

<210> SEQ ID NO 59
<211> LENGTH: 21
<212> TYPE: DNA
<213> ORGANISM: Artificial Sequence
```

```
<220> FEATURE:
<223> OTHER INFORMATION: passenger strand P56* of artificial microRNA
      P56

<400> SEQUENCE: 59
cgccccactc ctcactttcc t                                              21

<210> SEQ ID NO 60
<211> LENGTH: 21
<212> TYPE: DNA
<213> ORGANISM: Artificial Sequence
<220> FEATURE:
<223> OTHER INFORMATION: artificial microRNA P20

<400> SEQUENCE: 60
taaaactaga gccacgtgcc g                                              21

<210> SEQ ID NO 61
<211> LENGTH: 21
<212> TYPE: DNA
<213> ORGANISM: Artificial Sequence
<220> FEATURE:
<223> OTHER INFORMATION: passenger strand P20* of artificial microRNA
      P20

<400> SEQUENCE: 61
cgacacgtgg ctcaagtttt t                                              21

<210> SEQ ID NO 62
<211> LENGTH: 21
<212> TYPE: DNA
<213> ORGANISM: Artificial Sequence
<220> FEATURE:
<223> OTHER INFORMATION: artificial microRNA P55

<400> SEQUENCE: 62
taacgtggta gaagtgcgcg g                                              21

<210> SEQ ID NO 63
<211> LENGTH: 21
<212> TYPE: DNA
<213> ORGANISM: Artificial Sequence
<220> FEATURE:
<223> OTHER INFORMATION: passenger strand P55* of artificial microRNA
      P55

<400> SEQUENCE: 63
ccacgcactt ctagcacgtt t                                              21

<210> SEQ ID NO 64
<211> LENGTH: 21
<212> TYPE: DNA
<213> ORGANISM: Artificial Sequence
<220> FEATURE:
<223> OTHER INFORMATION: artificial microRNA P19

<400> SEQUENCE: 64
taacgtggta gaagtccgcg g                                              21

<210> SEQ ID NO 65
<211> LENGTH: 21
<212> TYPE: DNA
<213> ORGANISM: Artificial Sequence
<220> FEATURE:
<223> OTHER INFORMATION: passenger strand P19* of artificial microRNA
      P19
```

```
<400> SEQUENCE: 65
ccacggactt ctagcacgtt t                                              21

<210> SEQ ID NO 66
<211> LENGTH: 21
<212> TYPE: DNA
<213> ORGANISM: Artificial Sequence
<220> FEATURE:
<223> OTHER INFORMATION: artificial microRNA P54

<400> SEQUENCE: 66
taaagttaga gttcggaccg c                                              21

<210> SEQ ID NO 67
<211> LENGTH: 21
<212> TYPE: DNA
<213> ORGANISM: Artificial Sequence
<220> FEATURE:
<223> OTHER INFORMATION: passenger strand P54* of artificial microRNA
      P54

<400> SEQUENCE: 67
gcagtccgaa ctcaaacttt t                                              21

<210> SEQ ID NO 68
<211> LENGTH: 21
<212> TYPE: DNA
<213> ORGANISM: Artificial Sequence
<220> FEATURE:
<223> OTHER INFORMATION: artificial microRNA P18

<400> SEQUENCE: 68
tataatggca acatgcaggg g                                              21

<210> SEQ ID NO 69
<211> LENGTH: 21
<212> TYPE: DNA
<213> ORGANISM: Artificial Sequence
<220> FEATURE:
<223> OTHER INFORMATION: passenger strand P18* of artificial microRNA
      P18

<400> SEQUENCE: 69
ccactgcatg ttggcattat t                                              21

<210> SEQ ID NO 70
<211> LENGTH: 21
<212> TYPE: DNA
<213> ORGANISM: Artificial Sequence
<220> FEATURE:
<223> OTHER INFORMATION: artificial microRNA P53

<400> SEQUENCE: 70
tgttgggcga aaacgtccgt g                                              21

<210> SEQ ID NO 71
<211> LENGTH: 21
<212> TYPE: DNA
<213> ORGANISM: Artificial Sequence
<220> FEATURE:
<223> OTHER INFORMATION: passenger strand P53* of artificial microRNA
      P53

<400> SEQUENCE: 71
caaggacgtt ttcccccaac t                                              21
```

<210> SEQ ID NO 72
<211> LENGTH: 21
<212> TYPE: DNA
<213> ORGANISM: Artificial Sequence
<220> FEATURE:
<223> OTHER INFORMATION: artificial microRNA P17

<400> SEQUENCE: 72
tataatggca acatgggggg g                                              21

<210> SEQ ID NO 73
<211> LENGTH: 21
<212> TYPE: DNA
<213> ORGANISM: Artificial Sequence
<220> FEATURE:
<223> OTHER INFORMATION: passenger strand P17* of artificial microRNA
      P17

<400> SEQUENCE: 73
ccaccccatg ttggcattat t                                              21

<210> SEQ ID NO 74
<211> LENGTH: 21
<212> TYPE: DNA
<213> ORGANISM: Artificial Sequence
<220> FEATURE:
<223> OTHER INFORMATION: artificial microRNA P52

<400> SEQUENCE: 74
ttcgagtaaa tatcaggccc t                                              21

<210> SEQ ID NO 75
<211> LENGTH: 21
<212> TYPE: DNA
<213> ORGANISM: Artificial Sequence
<220> FEATURE:
<223> OTHER INFORMATION: passenger strand P52* of artificial microRNA
      P52

<400> SEQUENCE: 75
agagcctgat attaactcga t                                              21

<210> SEQ ID NO 76
<211> LENGTH: 21
<212> TYPE: DNA
<213> ORGANISM: Artificial Sequence
<220> FEATURE:
<223> OTHER INFORMATION: artificial microRNA P16

<400> SEQUENCE: 76
taaagttaga gttccgaccg c                                              21

<210> SEQ ID NO 77
<211> LENGTH: 21
<212> TYPE: DNA
<213> ORGANISM: Artificial Sequence
<220> FEATURE:
<223> OTHER INFORMATION: passenger strand P16* of artificial microRNA
      P16

<400> SEQUENCE: 77
gcagtcggaa ctcaaacttt t                                              21

<210> SEQ ID NO 78
<211> LENGTH: 21
<212> TYPE: DNA

```
<213> ORGANISM: Artificial Sequence
<220> FEATURE:
<223> OTHER INFORMATION: artificial microRNA P51

<400> SEQUENCE: 78
taacgtggta gaagtcccgc g                                              21

<210> SEQ ID NO 79
<211> LENGTH: 21
<212> TYPE: DNA
<213> ORGANISM: Artificial Sequence
<220> FEATURE:
<223> OTHER INFORMATION: passenger strand P51* of artificial microRNA
      P51

<400> SEQUENCE: 79
cgagggactt ctagcacgtt t                                              21

<210> SEQ ID NO 80
<211> LENGTH: 21
<212> TYPE: DNA
<213> ORGANISM: Artificial Sequence
<220> FEATURE:
<223> OTHER INFORMATION: artificial microRNA P15

<400> SEQUENCE: 80
ttagccgtca taacgtggta c                                              21

<210> SEQ ID NO 81
<211> LENGTH: 21
<212> TYPE: DNA
<213> ORGANISM: Artificial Sequence
<220> FEATURE:
<223> OTHER INFORMATION: passenger strand P15* of artificial microRNA
      P15

<400> SEQUENCE: 81
gtcccacgtt atgtcggcta t                                              21

<210> SEQ ID NO 82
<211> LENGTH: 21
<212> TYPE: DNA
<213> ORGANISM: Artificial Sequence
<220> FEATURE:
<223> OTHER INFORMATION: artificial microRNA P50

<400> SEQUENCE: 82
tagattcgaa ggtctacgtc t                                              21

<210> SEQ ID NO 83
<211> LENGTH: 21
<212> TYPE: DNA
<213> ORGANISM: Artificial Sequence
<220> FEATURE:
<223> OTHER INFORMATION: passenger strand P50* of artificial microRNA
      P50

<400> SEQUENCE: 83
agccgtagac cttggaatct t                                              21

<210> SEQ ID NO 84
<211> LENGTH: 21
<212> TYPE: DNA
<213> ORGANISM: Artificial Sequence
<220> FEATURE:
<223> OTHER INFORMATION: artificial microRNA P14
```

```
<400> SEQUENCE: 84
ttagccgtca taacgtggca g                                              21

<210> SEQ ID NO 85
<211> LENGTH: 21
<212> TYPE: DNA
<213> ORGANISM: Artificial Sequence
<220> FEATURE:
<223> OTHER INFORMATION: passenger strand P14* of artificial microRNA
      P14

<400> SEQUENCE: 85
ctaccacgtt atgtcggcta t                                              21

<210> SEQ ID NO 86
<211> LENGTH: 21
<212> TYPE: DNA
<213> ORGANISM: Artificial Sequence
<220> FEATURE:
<223> OTHER INFORMATION: artificial microRNA P49

<400> SEQUENCE: 86
tgaagagtta tgggcgaccc g                                              21

<210> SEQ ID NO 87
<211> LENGTH: 21
<212> TYPE: DNA
<213> ORGANISM: Artificial Sequence
<220> FEATURE:
<223> OTHER INFORMATION: passenger strand P49* of artificial microRNA
      P49

<400> SEQUENCE: 87
cgagtcgccc atatctcttc t                                              21

<210> SEQ ID NO 88
<211> LENGTH: 21
<212> TYPE: DNA
<213> ORGANISM: Artificial Sequence
<220> FEATURE:
<223> OTHER INFORMATION: artificial microRNA P13

<400> SEQUENCE: 88
ttagccgtca taacgtggtg g                                              21

<210> SEQ ID NO 89
<211> LENGTH: 21
<212> TYPE: DNA
<213> ORGANISM: Artificial Sequence
<220> FEATURE:
<223> OTHER INFORMATION: passenger strand P13* of artificial microRNA
      P13

<400> SEQUENCE: 89
cccccacgtt atgtcggcta t                                              21

<210> SEQ ID NO 90
<211> LENGTH: 21
<212> TYPE: DNA
<213> ORGANISM: Artificial Sequence
<220> FEATURE:
<223> OTHER INFORMATION: artificial microRNA P48

<400> SEQUENCE: 90
tatgactaga gtgttcgggg g                                              21
```

<210> SEQ ID NO 91
<211> LENGTH: 21
<212> TYPE: DNA
<213> ORGANISM: Artificial Sequence
<220> FEATURE:
<223> OTHER INFORMATION: passenger strand P48* of artificial microRNA
      P48

<400> SEQUENCE: 91
ccaccgaaca ctcaagtcat t                                              21

<210> SEQ ID NO 92
<211> LENGTH: 21
<212> TYPE: DNA
<213> ORGANISM: Artificial Sequence
<220> FEATURE:
<223> OTHER INFORMATION: artificial microRNA P12

<400> SEQUENCE: 92
tgatgccgaa taaactggag c                                              21

<210> SEQ ID NO 93
<211> LENGTH: 21
<212> TYPE: DNA
<213> ORGANISM: Artificial Sequence
<220> FEATURE:
<223> OTHER INFORMATION: passenger strand P12* of artificial microRNA
      P12

<400> SEQUENCE: 93
gccccagttt attgggcatc t                                              21

<210> SEQ ID NO 94
<211> LENGTH: 21
<212> TYPE: DNA
<213> ORGANISM: Artificial Sequence
<220> FEATURE:
<223> OTHER INFORMATION: artificial microRNA P47

<400> SEQUENCE: 94
tgtggagtaa tcggcgtgct g                                              21

<210> SEQ ID NO 95
<211> LENGTH: 21
<212> TYPE: DNA
<213> ORGANISM: Artificial Sequence
<220> FEATURE:
<223> OTHER INFORMATION: passenger strand P47* of artificial microRNA
      P47

<400> SEQUENCE: 95
caacacgccg atttctccac t                                              21

<210> SEQ ID NO 96
<211> LENGTH: 21
<212> TYPE: DNA
<213> ORGANISM: Artificial Sequence
<220> FEATURE:
<223> OTHER INFORMATION: artificial microRNA P11

<400> SEQUENCE: 96
taacgtggta gaagtgcgcg g                                              21

<210> SEQ ID NO 97
<211> LENGTH: 21
<212> TYPE: DNA

```
<213> ORGANISM: Artificial Sequence
<220> FEATURE:
<223> OTHER INFORMATION: passenger strand P11* of artificial microRNA
      P11

<400> SEQUENCE: 97
ccacgcactt ctagcacgtt t                                              21

<210> SEQ ID NO 98
<211> LENGTH: 21
<212> TYPE: DNA
<213> ORGANISM: Artificial Sequence
<220> FEATURE:
<223> OTHER INFORMATION: artificial microRNA P46

<400> SEQUENCE: 98
tgaagagtta tgggcaacgg g                                              21

<210> SEQ ID NO 99
<211> LENGTH: 21
<212> TYPE: DNA
<213> ORGANISM: Artificial Sequence
<220> FEATURE:
<223> OTHER INFORMATION: passenger strand P46* of artificial microRNA
      P46

<400> SEQUENCE: 99
ccagttgccc atatctcttc t                                              21

<210> SEQ ID NO 100
<211> LENGTH: 21
<212> TYPE: DNA
<213> ORGANISM: Artificial Sequence
<220> FEATURE:
<223> OTHER INFORMATION: artificial microRNA P10

<400> SEQUENCE: 100
taagcgaata tatctcggcg c                                              21

<210> SEQ ID NO 101
<211> LENGTH: 21
<212> TYPE: DNA
<213> ORGANISM: Artificial Sequence
<220> FEATURE:
<223> OTHER INFORMATION: passenger strand P10* of artificial microRNA
      P10

<400> SEQUENCE: 101
gcaccgagat ataatcgctt t                                              21

<210> SEQ ID NO 102
<211> LENGTH: 21
<212> TYPE: DNA
<213> ORGANISM: Artificial Sequence
<220> FEATURE:
<223> OTHER INFORMATION: artificial microRNA P45

<400> SEQUENCE: 102
tatgacggca ggtcgaacgg c                                              21

<210> SEQ ID NO 103
<211> LENGTH: 21
<212> TYPE: DNA
<213> ORGANISM: Artificial Sequence
<220> FEATURE:
<223> OTHER INFORMATION: passenger strand P45* of artificial microRNA
      P45
```

<400> SEQUENCE: 103
gcagttcgac ctggcgtcat t                                              21

<210> SEQ ID NO 104
<211> LENGTH: 21
<212> TYPE: DNA
<213> ORGANISM: Artificial Sequence
<220> FEATURE:
<223> OTHER INFORMATION: artificial microRNA P9

<400> SEQUENCE: 104
tgattacgaa taagtttcct g                                              21

<210> SEQ ID NO 105
<211> LENGTH: 21
<212> TYPE: DNA
<213> ORGANISM: Artificial Sequence
<220> FEATURE:
<223> OTHER INFORMATION: passenger strand P9* of artificial microRNA P9

<400> SEQUENCE: 105
caagaaactt attggtaatc t                                              21

<210> SEQ ID NO 106
<211> LENGTH: 21
<212> TYPE: DNA
<213> ORGANISM: Artificial Sequence
<220> FEATURE:
<223> OTHER INFORMATION: artificial microRNA P44

<400> SEQUENCE: 106
tttatgggca acgcggtcga c                                              21

<210> SEQ ID NO 107
<211> LENGTH: 21
<212> TYPE: DNA
<213> ORGANISM: Artificial Sequence
<220> FEATURE:
<223> OTHER INFORMATION: passenger strand P44* of artificial microRNA
      P44

<400> SEQUENCE: 107
gtagaccgcg ttggccataa t                                              21

<210> SEQ ID NO 108
<211> LENGTH: 21
<212> TYPE: DNA
<213> ORGANISM: Artificial Sequence
<220> FEATURE:
<223> OTHER INFORMATION: artificial microRNA P8

<400> SEQUENCE: 108
taaagttaga gttccgacga c                                              21

<210> SEQ ID NO 109
<211> LENGTH: 21
<212> TYPE: DNA
<213> ORGANISM: Artificial Sequence
<220> FEATURE:
<223> OTHER INFORMATION: passenger strand P8* of artificial microRNA P8

<400> SEQUENCE: 109
gtagtcggaa ctcaaacttt t                                              21

```
<210> SEQ ID NO 110
<211> LENGTH: 21
<212> TYPE: DNA
<213> ORGANISM: Artificial Sequence
<220> FEATURE:
<223> OTHER INFORMATION: artificial microRNA P43

<400> SEQUENCE: 110
ttcgttacta ttcccctgac g                                          21

<210> SEQ ID NO 111
<211> LENGTH: 21
<212> TYPE: DNA
<213> ORGANISM: Artificial Sequence
<220> FEATURE:
<223> OTHER INFORMATION: passenger strand P43* of artificial microRNA
      P43

<400> SEQUENCE: 111
cgccagggga atactaacga t                                          21

<210> SEQ ID NO 112
<211> LENGTH: 21
<212> TYPE: DNA
<213> ORGANISM: Artificial Sequence
<220> FEATURE:
<223> OTHER INFORMATION: artificial microRNA P7

<400> SEQUENCE: 112
tttaaaacta gagccacgcg g                                          21

<210> SEQ ID NO 113
<211> LENGTH: 21
<212> TYPE: DNA
<213> ORGANISM: Artificial Sequence
<220> FEATURE:
<223> OTHER INFORMATION: passenger strand P7* of artificial microRNA P7

<400> SEQUENCE: 113
ccacgtggct ctactttaa t                                           21

<210> SEQ ID NO 114
<211> LENGTH: 21
<212> TYPE: DNA
<213> ORGANISM: Artificial Sequence
<220> FEATURE:
<223> OTHER INFORMATION: artificial microRNA P42

<400> SEQUENCE: 114
ttagttggaa ggtctcggac t                                          21

<210> SEQ ID NO 115
<211> LENGTH: 21
<212> TYPE: DNA
<213> ORGANISM: Artificial Sequence
<220> FEATURE:
<223> OTHER INFORMATION: passenger strand P42* of artificial microRNA
      P42

<400> SEQUENCE: 115
agcccgagac cttgcaacta t                                          21

<210> SEQ ID NO 116
<211> LENGTH: 21
<212> TYPE: DNA
<213> ORGANISM: Artificial Sequence
<220> FEATURE:
```

```
<223> OTHER INFORMATION: artificial microRNA P6

<400> SEQUENCE: 116
ttcgagtaaa tatcagacgt t                                              21

<210> SEQ ID NO 117
<211> LENGTH: 21
<212> TYPE: DNA
<213> ORGANISM: Artificial Sequence
<220> FEATURE:
<223> OTHER INFORMATION: passenger strand P6* of artificial microRNA P6

<400> SEQUENCE: 117
aaagtctgat attaactcga t                                              21

<210> SEQ ID NO 118
<211> LENGTH: 21
<212> TYPE: DNA
<213> ORGANISM: Artificial Sequence
<220> FEATURE:
<223> OTHER INFORMATION: artificial microRNA P41

<400> SEQUENCE: 118
tatgactaga gtgttgcggg g                                              21

<210> SEQ ID NO 119
<211> LENGTH: 21
<212> TYPE: DNA
<213> ORGANISM: Artificial Sequence
<220> FEATURE:
<223> OTHER INFORMATION: passenger strand P41* OF artificial microRNA
      P41

<400> SEQUENCE: 119
ccacgcaaca ctcaagtcat t                                              21

<210> SEQ ID NO 120
<211> LENGTH: 21
<212> TYPE: DNA
<213> ORGANISM: Artificial Sequence
<220> FEATURE:
<223> OTHER INFORMATION: artificial microRNA P5

<400> SEQUENCE: 120
ttcgagtaaa tatcggacgt t                                              21

<210> SEQ ID NO 121
<211> LENGTH: 21
<212> TYPE: DNA
<213> ORGANISM: Artificial Sequence
<220> FEATURE:
<223> OTHER INFORMATION: passenger strand P5* OF artificial microRNA P5

<400> SEQUENCE: 121
aaagtccgat attaactcga t                                              21

<210> SEQ ID NO 122
<211> LENGTH: 21
<212> TYPE: DNA
<213> ORGANISM: Artificial Sequence
<220> FEATURE:
<223> OTHER INFORMATION: artificial microRNA P40

<400> SEQUENCE: 122
taatatcaga ccttcaagcg t                                              21
```

<210> SEQ ID NO 123
<211> LENGTH: 21
<212> TYPE: DNA
<213> ORGANISM: Artificial Sequence
<220> FEATURE:
<223> OTHER INFORMATION: passenger strand P40* OF artificial microRNA
      P40

<400> SEQUENCE: 123
acacttgaag gtcagatatt t                                            21

<210> SEQ ID NO 124
<211> LENGTH: 21
<212> TYPE: DNA
<213> ORGANISM: Artificial Sequence
<220> FEATURE:
<223> OTHER INFORMATION: artificial microRNA P4

<400> SEQUENCE: 124
tttgggcgaa aacatccctc g                                            21

<210> SEQ ID NO 125
<211> LENGTH: 21
<212> TYPE: DNA
<213> ORGANISM: Artificial Sequence
<220> FEATURE:
<223> OTHER INFORMATION: passenger strand P4* OF artificial microRNA P4

<400> SEQUENCE: 125
cgcgggatgt tttggcccaa t                                            21

<210> SEQ ID NO 126
<211> LENGTH: 21
<212> TYPE: DNA
<213> ORGANISM: Artificial Sequence
<220> FEATURE:
<223> OTHER INFORMATION: artificial microRNA P39

<400> SEQUENCE: 126
taacggttta tgcccgagcg t                                            21

<210> SEQ ID NO 127
<211> LENGTH: 21
<212> TYPE: DNA
<213> ORGANISM: Artificial Sequence
<220> FEATURE:
<223> OTHER INFORMATION: passenger strand P39* of artificial microRNA
      P39

<400> SEQUENCE: 127
acactcgggc ataccgtt t                                              21

<210> SEQ ID NO 128
<211> LENGTH: 21
<212> TYPE: DNA
<213> ORGANISM: Artificial Sequence
<220> FEATURE:
<223> OTHER INFORMATION: artificial microRNA P3

<400> SEQUENCE: 128
taaattacca tacatgcctc t                                            21

<210> SEQ ID NO 129
<211> LENGTH: 21
<212> TYPE: DNA
<213> ORGANISM: Artificial Sequence

```
-continued

<220> FEATURE:
<223> OTHER INFORMATION: passenger strand P3* of artificial microRNA P3

<400> SEQUENCE: 129
agcggcatgt atgctaattt t                                              21

<210> SEQ ID NO 130
<211> LENGTH: 21
<212> TYPE: DNA
<213> ORGANISM: Artificial Sequence
<220> FEATURE:
<223> OTHER INFORMATION: artificial microRNA P38

<400> SEQUENCE: 130
tttatgggca acgcgaccga c                                              21

<210> SEQ ID NO 131
<211> LENGTH: 21
<212> TYPE: DNA
<213> ORGANISM: Artificial Sequence
<220> FEATURE:
<223> OTHER INFORMATION: passenger strand P38* of artificial microRNA
      P38

<400> SEQUENCE: 131
gtaggtcgcg ttggccataa t                                              21

<210> SEQ ID NO 132
<211> LENGTH: 21
<212> TYPE: DNA
<213> ORGANISM: Artificial Sequence
<220> FEATURE:
<223> OTHER INFORMATION: artificial microRNA P2

<400> SEQUENCE: 132
taagcgaata tatctcaggg t                                              21

<210> SEQ ID NO 133
<211> LENGTH: 21
<212> TYPE: DNA
<213> ORGANISM: Artificial Sequence
<220> FEATURE:
<223> OTHER INFORMATION: passenger strand P2* of artificial microRNA P2

<400> SEQUENCE: 133
acactgagat ataatcgctt t                                              21

<210> SEQ ID NO 134
<211> LENGTH: 21
<212> TYPE: DNA
<213> ORGANISM: Artificial Sequence
<220> FEATURE:
<223> OTHER INFORMATION: artificial microRNA P37

<400> SEQUENCE: 134
tccaaagtta gagttccgac g                                              21

<210> SEQ ID NO 135
<211> LENGTH: 21
<212> TYPE: DNA
<213> ORGANISM: Artificial Sequence
<220> FEATURE:
<223> OTHER INFORMATION: passenger strand P37* of artificial microRNA
      P37

<400> SEQUENCE: 135
```
cgccggaact ctatctttgg t                                        21

<210> SEQ ID NO 136
<211> LENGTH: 21
<212> TYPE: DNA
<213> ORGANISM: Artificial Sequence
<220> FEATURE:
<223> OTHER INFORMATION: artificial microRNA P1

<400> SEQUENCE: 136
taagcgaata tatctcagcg c                                        21

<210> SEQ ID NO 137
<211> LENGTH: 21
<212> TYPE: DNA
<213> ORGANISM: Artificial Sequence
<220> FEATURE:
<223> OTHER INFORMATION: passenger strand P1* of artificial microRNA P1

<400> SEQUENCE: 137
gcactgagat ataatcgctt t                                        21

<210> SEQ ID NO 138
<211> LENGTH: 21
<212> TYPE: DNA
<213> ORGANISM: Artificial Sequence
<220> FEATURE:
<223> OTHER INFORMATION: artificial microRNA P36

<400> SEQUENCE: 138
taatatcaga ccttggagcg t                                        21

<210> SEQ ID NO 139
<211> LENGTH: 21
<212> TYPE: DNA
<213> ORGANISM: Artificial Sequence
<220> FEATURE:
<223> OTHER INFORMATION: passenger strand P36* of artificial microRNA
      P36

<400> SEQUENCE: 139
acactccaag gtcagatatt t                                        21

<210> SEQ ID NO 140
<211> LENGTH: 24
<212> TYPE: DNA
<213> ORGANISM: Artificial Sequence
<220> FEATURE:
<223> OTHER INFORMATION: primer

<400> SEQUENCE: 140
gactagagcc aagctgatct cctt                                     24

<210> SEQ ID NO 141
<211> LENGTH: 24
<212> TYPE: DNA
<213> ORGANISM: Artificial Sequence
<220> FEATURE:
<223> OTHER INFORMATION: primer

<400> SEQUENCE: 141
aggtcactgg attttggttt tagg                                     24

<210> SEQ ID NO 142
<211> LENGTH: 24
<212> TYPE: DNA

```
<213> ORGANISM: Artificial Sequence
<220> FEATURE:
<223> OTHER INFORMATION: Primer

<400> SEQUENCE: 142
tgccggtgat cttctcggaa aaca                                              24

<210> SEQ ID NO 143
<211> LENGTH: 24
<212> TYPE: DNA
<213> ORGANISM: Artificial Sequence
<220> FEATURE:
<223> OTHER INFORMATION: Primer

<400> SEQUENCE: 143
agaaaccatc ggcgcagcta ttta                                              24

<210> SEQ ID NO 144
<211> LENGTH: 24
<212> TYPE: DNA
<213> ORGANISM: Artificial Sequence
<220> FEATURE:
<223> OTHER INFORMATION: Primer

<400> SEQUENCE: 144
tcacttcctc gctgcgctca agtg                                              24

<210> SEQ ID NO 145
<211> LENGTH: 24
<212> TYPE: DNA
<213> ORGANISM: Artificial Sequence
<220> FEATURE:
<223> OTHER INFORMATION: Primer

<400> SEQUENCE: 145
tcgtattggg aatccccgaa catc                                              24
```

METHOD FOR INTRODUCING A POLYNUCLEOTIDE INTO NON-ADHESIVELY GROWING PLANT CELLS

PRIORITY

This application corresponds to the national phase of International Application No. PCT/EP2011/070602 filed Nov. 21, 2011, which, in turn, claims priority to European Patent Application No. 10.191985.0 filed Nov. 19, 2010, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Jul. 18, 2013, is named LNK_133_Sequence_Listing_US_ST25.txt and is 64,154 bytes in size.

BACKGROUND

Plant as well as bacterial or fungal protoplasts are cells in which the cell wall was partially or completely removed by either mechanical or enzymatic treatment. Since 1961, when enzymatic methods of protoplast isolation from plant tissues were reported, these cell-wall-less cells faced various periods of "popularity". In 1970s totipotency of plant protoplasts was demonstrated by generating fertile plants from these cells. This led to a "golden age" period during which major methods and techniques for cell preparation, handling and treatments including approaches for DNA uptake were developed. Further expectations were raised with respect to generation of plants with novel properties using genetic manipulation of protoplasts (e.g. nuclear and organelle transformation, or generation of hybrids and cybrids). Protoplasts were used as a versatile system to study plant cell development and physiology, cytodifferentiation, organellogenesis, membrane transport and plant virus function and interaction of viruses with plant cells. Recent advances in genomics, transcriptomics, proteomics and discovery of fluorescent proteins led to "renaissance" of protoplasts in modern science. Despite regular exploitation of protoplasts to study gene and protein function application of protoplasts in high-throughput assays are rather rare. Reasons for this are absence of efficient, practical and economical methods to handle and maintain cell cultures at large scales. Protoplast isolation is now routine from a wide range of plant species. Typically, a protoplast isolation procedure consists of a filtration step to remove large debris after cell wall digestion and one or several centrifugation steps using solutions osmotically and ionically adjusted for a given species to further purify intact and, in special cases, specific cell types, e.g. guard cells, epidermis cells and other cells. Numerous factors, such as different plant material, pre-isolation, isolation and post-isolation physical and chemical requirements and nutrient composition of media used and combination of growth regulators, influence division frequencies of protoplasts and subsequent development of protoplast-derived colonies. Seasonal and internal clock conditions may influence cell behaviour even in vitro, but very likely is species specific.

After preparation cells are typically used for analysis and subsequent culture immediately. Protoplasts can be used, for example, for drug assays, transient and/or stable transformation or somatic hybridisation. However, as freshly prepared plant protoplasts do not easily take up foreign nucleic acids protocols need to be developed for efficient DNA uptake at large scale.

BART et al: PLANT METHODS, vol. 2, page 13 (2006) describes a novel system for gene silencing using siRNAs in rice leaf and stem-derived protoplasts. The protoplasts were transformed with various plasmids using PEG as a transformation agent. For the transformation the DNA was dissolved in a liquid.

YAMADA et al: METHODS IN MOLECULAR BIOLOGY, vol. 643 (2010), pages 33-45 describes protocols for the identification of regulatory protein genes involved in alkaloid biosynthesis using a transient RNAi system. Transformation is carried out using PEG as transformation agent and DNA dissolved in a liquid.

CRAIG et al: PLANT CELL REPORTS, vol. 24, no. 10 (2005), pages 603-611 compares particle bombardment of leaf explants and PEG-mediated transformation of protoplasts. The nucleic acids used for PEG-mediated transformation were dissolved in a liquid.

YOO et al: NATURE PROTOCOLS vol. 2, no. 7 (2007), pages 1565-1572 investigates *Arabidopsis* mesophyll protoplasts as a cell system for transient gene expression analysis. "DNA-PEG-calcium transfection" using DNA in solution is described.

An Advertising Feature of GenVault Corporation, Carlsbad, Calif., USA [Kansagara et al: NATURE METHODS, vol. 5 (September 2008)] describes dry-state, room-temperature storage of DNA and RNA. The nucleic acids stored in this way, however, cannot be directly used in their dry state. Rather, they first have to be eluted and purified before further use, e.g. in transformation.

In contrast to many human and animal cell cultures (e.g. fibroblasts, pancreatic islet cells, human colon cancer cells and many others) plant protoplasts are an example of non-adhesively growing cells. So far only liquid cultured protoplasts could be used in assays enabling high-throughput analysis. There are several drawbacks of liquid culture. The main one is the impossibility to find the same object/cell for microscopy observation again and again over continuous time periods whenever container with cultured protoplasts should be translocated or moved. This becomes particularly essential if e.g. multiple emission channels are to be compared and analyzed by means of computational tools. Only a switch between 2 channels may lead to microvibrations resulting in cell translocation and thus in a shift between different channels. Another limitation is not-avoidable cell aggregation when cultured in liquid medium over continuous time period. This makes impossible appropriate analysis by e.g. microscopy means. In addition, protoplast populations often consist of more than one cell type by origin, which could additionally be at different developmental states. The cellular heterogeneity and data extrapolation is a problem, and liquid culture does not allow to solve it.

Immobilisation of non-adhesively growing cells is necessary to prevent non-predictable and uncontrolled cell movement, which is not avoidable if cells float freely in the culture medium. Protoplast embedding into semi-solid matrixes allows developing cells to generate microenvironments. Numerous reports demonstrated that immobilisation of plant protoplasts resulted in higher plating efficiencies and optimised cell development. Furthermore, effect of drugs and/or physiologically active compounds can be easily investigated by replacing of incubation/culture media. Immobilised cells or surface growing cells could be subjected to automated microscopy to generate image data suitable for statistical analysis afterwards.

US 2002/173037 A1 describes a method of protoplast culture which comprises mixing protoplasts with alginate solution, placing a $CaCl_2$ solution on a glass microslide, placing a mixture of protoplasts and alginate solution on the glass microslide and immediately covering by a glass coverglass, adding $CaCl_2$ solution in an amount of 70 to 100 µl from the sides of coverglass, sliding down the coverglass towards one side after four to ten minutes and placing it in a petridish containing protoplast culture medium, sealing the petridishes with parafilm and incubating in dark/diffused light at 20 to 27° C., and transferring the extra thin alginate layer with 20-25 celled colonies to regeneration medium for development of culture. This process is rather cumbersome, e.g. the coverglasses have to be handled by forceps (see FIG. 1). Thus, it is not suitable for a high-throughput screening or a fully automated process.

Golds et al: J PLANT PHYSIOL, vol. 140, pages 582-587 established the "thin alginate layer" (TAL) technique, in which protoplasts are enmeshed in an alginate medium and placed in liquid culture medium.

PATI al.: PROTOPLASMA, vol. 226, no. 3-4 (2005), pages 217-221 developed "extra thin alginate films" (ETAF) in order to establish a technique for protoplast culture. The ETAF technique described in this reference requires placing protoplasts on a microscope slide and placing a coverglass on top of the cells. The coverglass is then removed with the help of jeweler's forceps. This technique is not suitable for a high-throughput screening or a fully automated process due to the rather complicated handling involving coverglasses and forceps.

The TAL technique may be suitable for cell tracking, but this will require transfer of the carrier into a plate/container appropriate for microscopy. In addition, this method cannot be used for automation of handling procedures and is based on exclusively man-operated manipulation. Also, the TAL-technique is not suitable for high-throughput analysis since culture of polypropylene grids takes place in liquid environment, in which carriers are swimming, rotating etc. and not in multiwell format. This causes movement of the carrier with embedded protoplasts and without manual adjustments it is impossible to find the same object of interest again. Further, this method is not suitable for multi-well format.

The same criteria apply to the ETAF technique. This method is exclusively man-powered, handling is complicated and not suitable for high-throughput analysis. In addition, non-skilled persons cannot avoid high rates of contamination during manipulation. It requires translocation of the formed film by manual manipulations and cannot be automated, thus omitting high-throughput-oriented assays.

Despite existing procedures to immobilise non-adhesively growing cells such as plant protoplasts, none of them is suited efficiently for both, high-throughput and high-content analysis in combination with high resolution microscopy analysis, such as TIRF (Total Internal Reflection Fluorescence) microscopy. Established procedures result in cell trapping at various focal planes, thus increasing impact of artefacts on data quality while performing image analysis. The present invention provides methods which can be carried out in an automated manner, e.g. in high-throughput analysis, and thus allows successfully to overcome most of the above-mentioned obstacles.

The present invention provides an efficient method for high-throughput single cell analysis using robotic handling and automated microscopy. It was surprisingly found that the use of dried DNA for transforming plant cells resulted in highly reproducible transformation efficiencies which is important for automation of the transformation process. Especially the variation in the co-transformation efficiency was lower as compared to known transformation techniques using DNA dissolved in a liquid (see Example 5). It was further found that the transformation efficiency using the dried DNA was very low unless the cells were sedimented prior to or during the transformation.

SUMMARY OF THE INVENTION

A first aspect of the present invention is a method for introducing a polynucleotide into plant protoplast cells, comprising the following steps:
  (a) providing a solid support having immobilized thereto the polynucleotide in dry state;
  (b) contacting the plant protoplasts with the polynucleotide on the solid support so as to obtain transformed plant protoplast cells; and
  (c) optionally washing the plant protoplasts.

Another aspect of this invention is an automated method for analyzing cells, comprising the following steps:
  providing a culture of non-adhesively growing cells, preferably of plant protoplast cells;
  arranging the cells in a monolayer and immobilizing them in the monolayer; and
  detecting at least one parameter by microscopic analysis.

The non-adhesively growing cells according to this aspect include animal cells, yeast cells and plant cells. Preferably, the non-adhesively growing cells are plant protoplast cells.

Yet another aspect of the invention is a screening method to identify efficient artificial microRNA sequences, comprising the following steps:
  introducing a plasmid into plant protoplast cells so as to obtain transformed plant protoplast cells, wherein said plasmid comprises a nucleic acid sequence encoding a candidate artificial microRNA, a nucleic acid sequence representing the target gene of the candidate artificial microRNA, and optionally a nucleic acid sequence encoding a transformation marker;
  culturing the transformed plant protoplast cells under conditions that allow expression at least of the nucleic acid sequence encoding the candidate artificial microRNA, and of the nucleic acid sequence representing the target gene of the candidate artificial microRNA;
  selecting as efficient microRNA that candidate artificial microRNA sequence which is capable of efficiently inhibiting expression of the target gene.

Accordingly, the present invention relates to the following embodiments:

(1) A method for introducing a polynucleotide into non-adhesively growing eukaryotic cells from either plant or animal origin, comprising the following steps:
  (a) providing a solid support having immobilized thereto the polynucleotide in dry state;
  (b) contacting the non-adhesively growing cells with the polynucleotide on the solid support so as to obtain transformed non-adhesively growing cells, wherein step (b) comprises
    (i) adding to the solid support a suspension comprising the non-adhesively growing cells,
    (ii) arranging the non-adhesively growing cells in a layer on the solid support,
    (iii) adding a transformation agent to the suspension; and
    (iv) optionally removing the transformation agent from the non-adhesively growing cells;

and
(c) optionally washing the non-adhesively growing cells.

(2) The method of item (1), wherein step (a) comprises adding a solution containing the polynucleotide onto the solid support and removing the water from the solution on the solid support.

(3) The method of item (1) or (2), wherein after step (iii) the non-adhesively growing cells are incubated for 1 to 30 minutes in the presence of the transformation agent so as to obtain the transformed non-adhesively growing cells.

(4) The method of any one of items (1) to (3), wherein said transformation agent is selected from the group consisting of polyethylene glycol (PEG), poly-L-ornithine, polyvinyl alcohol and divalent ions.

(5) The method according to any one of items (1) to (4), wherein at least 3 different polynucleotides are immobilized on the same solid support, each polynucleotide being spatially separated from the other polynucleotides.

(6) The method according to item (5), wherein said solid support has a plurality of locations, preferably cavities, and each polynucleotide is immobilized at a separate location, preferably at the bottom of a separate cavity.

(7) The method of any one of items (1) to (6), wherein said non-adhesively growing cells are plant protoplast cells.

(8) The method of any one of items (1) to (7), wherein said polynucleotide comprises a nucleic acid sequence encoding artificial microRNA, a nucleic acid sequence representing the target gene of the artificial microRNA, and optionally a nucleic acid sequence encoding a transformation marker.

(9) A method for analyzing non-adhesively growing cells, comprising the following steps:
  introducing a polynucleotide into non-adhesively growing cells by a method according to any one of items (1) to (8) to obtain transformed non-adhesively growing cells;
  culturing the transformed non-adhesively growing cells under conditions that allow expression of at least one coding sequence comprised in the polynucleotide;
  arranging the transformed non-adhesively growing cells in a monolayer and immobilizing them in the monolayer; and
  detecting at least one parameter by microscopic analysis.

(10) The method of item (9), wherein the immobilization of the non-adhesively growing cells in a monolayer is achieved by adding a gelling substance to the non-adhesively growing cells, centrifuging the protoplast cells to obtain a monolayer of non-adhesively growing cells, and solidifying the gelling substance to form a gel in which the non-adhesively growing cells are embedded.

(11) The method of item (9) or (10), wherein said at least one parameter is selected from the group consisting of fluorescence, luminescence, morphology and combinations thereof.

(12) A screening method to identify efficient plant microRNA sequences, comprising the following steps:
  introducing a polynucleotide into non-adhesively growing cells by the method of item (8) so as to obtain transformed plant protoplast cells;
  culturing the transformed non-adhesively growing cells under conditions that allow expression at least of the nucleic acid sequence encoding the candidate artificial microRNA, and of the nucleic acid sequence representing the target gene of the candidate artificial microRNA;
  selecting as efficient microRNA that candidate artificial microRNA sequence which is capable of inhibiting expression of the target gene.

(13) The screening method of item (12), wherein the target gene is labeled with a first fluorescent protein, and the transformation marker is a second fluorescent protein.

(14) The screening method of item (10) or (11), wherein at least 24 different artificial microRNAs are examined in one screening cycle using one single solid support.

(15) The screening method of any one of items (12) to (14), wherein the inhibition of expression of the target gene is determined by microscopy.

(16) An automated method for analyzing a cell, comprising the following steps:
  providing a culture of non-adhesively growing cells;
  arranging the non-adhesively growing cells in a monolayer and immobilizing them in the monolayer; and
  detecting at least one parameter by microscopic analysis.

(17) The method of item (16), wherein said non-adhesively growing cells are plant protoplast cells.

(18) The method of item (16) or (17), wherein the immobilization of the non-adhesively growing cells in a monolayer is achieved by adding a gelling substance to the non-adhesively growing cells, centrifuging the protoplast cells to obtain a monolayer of non-adhesively growing cells, and solidifying the gelling substance to form a gel in which the non-adhesively growing cells are embedded.

(19) The method of any one of items (16) or (18), wherein said at least one parameter is selected from the group consisting of fluorescence, luminescence, morphology and combinations thereof.

(20) The method of any one of items (16) or (19), wherein said non-adhesively growing cells have been transformed with a polynucleotide to arranging them in a monolayer, preferably by a method as defined in any one of items (1) to (8).

(21) The method of item (20), wherein said polynucleotide is a linear double-stranded DNA consisting of a promoter, an open reading frame, and a terminator, and wherein said nucleic acid is directly used for the transformation without inserting it into a plasmid.

(22) A screening method to identify efficient artificial microRNA sequences, comprising the following steps:
  introducing a plasmid into non-adhesively growing plant cells so as to obtain transformed plant protoplast cells, wherein said plasmid comprises a nucleic acid sequence encoding a candidate artificial microRNA, a nucleic acid sequence representing the target gene of the candidate artificial microRNA, and optionally a nucleic acid sequence encoding a transformation marker;
  culturing the transformed non-adhesively growing plant cells under conditions that allow expression at least of the nucleic acid sequence encoding the candidate artificial microRNA, and of the nucleic acid sequence representing the target gene of the candidate artificial microRNA;
  determining the inhibition of expression of the target gene by the candidate artificial microRNA; and
  selecting as efficient microRNA that candidate artificial microRNA sequence which is capable of efficiently inhibiting expression of the target gene.

(23) The screening method of item (22), wherein the target gene is labeled with a first fluorescent protein, and the transformation marker is a second fluorescent protein.

(24) The screening method of item (22) or (23), wherein at least 24 different candidate artificial microRNAs are examined in one screening cycle.

(25) The screening method of any one of items (22) to (24), wherein the inhibition of expression of the target gene is determined by microscopy.

(26) The screening method of any one of items (22) to (25), wherein the plasmid is transformed into non-adhesively growing plant cells by a method as defined in any one of items (1) to (8).

(27) The screening method of any one of items (22) to (25), wherein, prior to the step of determining the inhibition of expression of the target gene, the transformed non-adhesively growing plant cells are arranged in a monolayer and immobilized in the monolayer, preferably as defined in item (18).

(28) The method of any one of items (1) to (15), wherein said polynucleotide is a linear double-stranded DNA consisting of a promoter, an open reading frame, and a terminator, and wherein said nucleic acid is directly used for the transformation without inserting it into a plasmid.

DETAILED DESCRIPTION

Definitions

In the context of this disclosure, a number of terms and abbreviations are used. The following definitions are provided.

"microRNA or miRNA" refers to oligoribonucleic acid, which regulates expression of a polynucleotide comprising the target sequence. microRNAs (miRNAs) are noncoding RNAs of about 19 to about 24 nucleotides (nt) in length that have been identified in both animals and plants which regulate expression of a polynucleotide comprising the target sequence. They are processed from longer precursor transcripts that range in size from approximately 70 to 2000 nt or longer, and these precursor transcripts have the ability to form stable hairpin structures. In plants, miRNAs usually have single, highly complementary target sites that mostly locate to coding regions. A miRNA is an "artificial miRNA" when it is genetically engineered. The artificial miRNA is thus predetermined to specifically target a single gene or multiple genes.

"pri-miRNAs" or "primary miRNAs" are long, polyadenylated RNAs transcribed by RNA polymerase II that encode miRNAs. "pre-miRNAs" are primary miRNAs that have been processed to form a shorter sequence that has the capacity to form a stable hairpin and is further processed to release a miRNA.

A "target gene" refers to a gene that encodes a target RNA, i.e., a gene from which a target RNA is transcribed. The gene may encode mRNA, tRNA, small RNA, etc. A "target sequence" refers to an RNA whose expression is to be modulated, e.g., down-regulated. The target sequence may be a portion of an open reading frame, 5' or 3' untranslated region, exon(s), intron(s), flanking region, etc.

A "star sequence" or "miRNA* strand" is the complementary sequence within a miRNA precursor that forms a duplex with the miRNA. The complementarity of the star sequence does not need to be perfect.

A new strategy developed using the knowledge on miRNA biology offered by combination of the advantages of RNAi and T-DNA insertion techniques. As plant miRNAs tend to show a high degree of sequence complementarity to their target RNA, several research groups assumed that miRNAs could be used for gene silencing studies. Based on different endogenous miRNA precursor sequences, they designed strategies to replace the 21-nucleotide stretch of the mature miRNA against a 21-nucleotide sequence complementary to a given target gene. By simultaneously exchanging the 21 nucleotides of the miRNA* strand, the stem-loop structure of the precursor was preserved and the processing resulted in a novel miRNA/miRNA* duplex against a chosen target gene. Their advantage lies in the specificity of sequence homology, based on the short length of only 21 nucleotides. They could therefore be applied for the knock-down of single as well as multiple genes with a single construct.

A recombinant construct comprises an artificial combination of nucleic acid fragments, e.g., regulatory and coding sequences that are not found together in nature. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

As used here "suppression" or "silencing" or "inhibition" are used interchangeably to denote the down-regulation of the expression of a product of a target sequence. If the suppression by an artificial miRNA is concerned, the degree of suppression by this artificial miRNA is determined relative to the same organism lacking the nucleic acid encoding the artificial miRNA (e.g. relative to a cell comprising the same target sequence which, however, lacks the nucleic acid sequence encoding the artificial miRNA). This "same organism" (e.g. a cell) should be identical to the test organism (cell) comprising the nucleic acid encoding the artificial miRNA, except that the nucleic acid sequence encoding the artificial miRNA to be tested is absent. Suppression includes expression that is decreased by at least about 10%, preferably by at least about 25%, more preferably by at least about 50%, more preferably by at least about 75%, most preferably by at least about 90%, e.g. by about 95% or about 100% relative to the same organism (e.g. a cell) which lacks the nucleic acid sequence encoding the artificial microRNA.

As used herein, "encodes" or "encoding" refers to a DNA sequence which can be processed to generate an RNA and/or polypeptide.

As used herein, "expression" or "expressing" refers to production of a functional product, such as, the generation of an RNA transcript from a DNA sequence. The term may also refer to a polypeptide produced from an mRNA generated from a DNA precursor. Thus, expression of a nucleic acid fragment may refer to transcription of the nucleic acid fragment and/or translation of RNA into a polypeptide.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores. Preferably, the plant cells used herein are monocotyledonous or dicotyledonous plant cells, but also lower plants such as algae or mosses like *Physcomitrella patens* or else.

An example of a monocotyledonous cell is a maize cell. Preferably, the plant cell is a dicot plant cell. Examples of dicot plant cells include soybean, rapeseed, sunflower, flax, cotton, barley, bean, pea, tobacco, and *Arabidopsis*.

The term "introduced" means providing a nucleic acid (e.g., expression construct) or protein into a cell. Introduction of nucleic acid into plant cells is referred to herein also as "transformation". The transformation may be transient or stable.

Method for Introducing a Polynucleotide into Plant Protoplast Cells

According to a first aspect, the present invention pertains to a method for introducing a polynucleotide into plant protoplast cells, comprising the following steps: (a) providing a solid support having immobilized thereto the polynucleotide in dry state; (b) contacting the plant protoplasts with the polynucleotide on the solid support so as to obtain transformed plant protoplast cells; and (c) optionally washing the plant protoplasts.

Preferably, the plant protoplast cells used herein are derived from monocotyledonous or dicotyledonous plants or lower plants. The phrase "derived from" means "obtained from" or "isolated from". An example of a monocotyledonous plant is maize. Preferably, the plant protoplast cells are derived from dicotyledonous plants. Examples of dicotyledonous plants include soybean, rapeseed, sunflower, flax, cotton, barley, bean, pea, tobacco, and *Arabidopsis*. Most preferably, the plant protoplast cells are derived from *Arabidopsis*, e.g. *Arabidopsis thaliana*.

Methods for isolating plant protoplast cells are known to the skilled person. Suitable protocols can be found in, e.g., *Arabidopsis* protocols, $2^{nd}$ edition 2005 (Methods in molecular biology) edited by Julio Salinas and Jose J. Sanchez-Serrano (ISBN 978-1-61737-539-2); Davey and Anthony, Plant Cell Culture: Essential Methods, $1^{st}$ ed. 2010, (ISBN 978-0470686485).

The solid support may be made of any material which does not adversely affect the growth of plant protoplast cells. Preferably, the solid support does not contain tungsten or gold, or it does not consist of tungsten or gold. More preferably the solid support does not contain a metal, or it does not consist of a metal. The solid support is preferably made of a water-impermeable material. Suitable materials include, but are not limited to, glass, polystyrene, polypropylene, polycarbonate. Preferably, the solid support is suitable to allow one or more of optical absorbance, fluorescence and luminescence detection. Typically, the solid support comprises one or more planar or concave surfaces; and/or the solid support does not have a spherical form. In a preferred embodiment, the solid support has a plurality of locations, preferably cavities, where different polynucleotides may be immobilized. This embodiment is preferably a multi-well plate having a plurality of "wells" or "cavities". At the bottom of the cavities, the surface is preferably planar or concave. Suitable types include multi-well culture plates in 6-, 12-, 24-, 48-, 96-, 384- or higher well formats. Preferred are 24-well plates, more preferred are 48-well plates, most preferred are 96-well plates. The nominal volume of each well is preferably from 0.1 ml to about 2 ml, most preferably it is about 0.5-1 ml.

In a preferred embodiment, the polynucleotide is immobilized on the solid support by adding a solution containing the polynucleotide onto the solid support and removing the water from the solution on the solid support. The removal of the water can be achieved by letting evaporate the water over about 6-48 h, preferably over about 12-36 h, e.g. 24 h. This is preferably done under sterile conditions, e.g. under a sterile flow hood. Alternatively, the water may be removed by vacuum exsiccation.

Typically, 0.1 µg to 10 µg, preferably 0.2 µg to 5 µg, more preferably 0.3 µg to 2 µg, most preferably 0.5 µg to 1.5 µg of (each) polynucleotide is added to the solid support or to each separate location of the solid support.

The dried DNA immobilized on the solid support can be stored, e.g. at −20° C. or lower, for at least 1 month, e.g. for at least 2 or 3 or 4 or 5 or 6 months or 12 months or longer.

The transformation step may comprise adding to the solid support a suspension comprising the plant protoplasts. The protoplasts are preferably suspended in a suitable medium that does not adversely affect or inhibit later transformation, e.g. TM550 (see Table 1 infra). As an example, the following medium can be used: 0.5 mM MES (salt-free), 15 mM $MgCl_2$, 0.48 mM mannitol, pH 5.8 (TM550).

The cell density in the protoplast suspension may range from about $1 \times 10^4$ to about $1 \times 10^8$, preferably from about $1 \times 10^5$ to about $1 \times 10^7$, more preferably from about $5 \times 10^5$ to about $2 \times 10^5$, most preferably it is about $1 \times 10^6$ protoplast cells per ml. The suspension of non-adhesively growing plant cells may be added directly to the dried DNA on the solid support. Alternatively, the dried DNA may first be re-dissolved in a suitable solution, followed by addition of the cell suspension. Preferably, 10 µl to 500 µl, more preferably 20 µl to 200 µl, still more preferably 25 µl to 100 µl, most preferably 30 µl to 50 µl of protoplast suspension is added to the DNA, e.g. in a cavity of a multi-well plate.

Afterwards the cells are arranged in a layer on the solid support. Typically, the cells are sedimented so as to arrange them in a layer on the solid support (e.g. at the bottom of a well or cavity of a multi-well plate). The term "sedimenting", as used herein, includes actively sedimenting the cells by applying a centrifugal force to the cells, and passively sedimenting the cells, i.e. allowing the cells to sediment (settle) on the solid support by way of the normal gravity. The cells may be allowed to sediment for about 0.3 to 60 min, preferably for about 0.5 to 10 min, most preferably for about 1 to 2 minutes (passive sedimentation). Alternatively, protoplasts could be centrifuged for at least 30 seconds at least 2 g, e.g. for 1 min at 10 g (Active sedimentation). After the sedimentation step the cells are arranged in a layer, preferably a monolayer, on the solid support, e.g. at the bottom of a well or cavity of a multi-well plate.

Next the transformation of the cells is effected, preferably by a chemically induced nucleic acid uptake. Suitable procedures are known to those of skill in the art (Negrutiu I, Shillito R, Potrykus I, Biasini G, Sala F (1987) Hybrid genes in the analysis of transformation conditions. I. Setting up a simple method for direct gene transfer in plant protoplasts. Plant Mol Biol 8: 363-373; Koop H U, Steinmuller K, Wagner H, Rössler C, Eibl C, Sacher L (1996) Integration of foreign sequences into the tobacco plastome via polyethylene glycol-mediated protoplast transformation. Planta, 199: 193-201; Yoo S D, Cho Y H, Sheen J (2007) *Arabidopsis* mesophyll protoplasts: a versatile cell system for transient gene expression analysis. Nat Protoc 2:1565-1572). Preferably, a transformation agent is added to the protoplast suspension comprising the polynucleotide in order to induce nucleic acid uptake. The transformation agent may be polyethylene glycol (PEG) or another suitable agent which induces DNA uptake into protoplasts. Alternative transformation agents include poly-L-ornithine, polyvinyl alcohol and divalent ions. Preferably, the PEG is PEG 1500. The transformation agent is usually comprised in a solution which is added to protoplast suspension. For example, an equal volume of 40% PEG 1500 may be added to the protoplast suspension. A preferred composition to be added to the protoplast suspension is as follows: 67 mM $Ca(NO_3)_2 \cdot 4H_2O$, 270 mM Mannitol, 384 g/l PEG1500, pH 9.75 (see also Table 1 infra).

After addition, the suspension is preferably incubated for about 7 to 10 minutes. After that, TM550 may be added, preferably about 40 to 60% of the volume of the suspension (protoplasts+transformation agent composition) already present in the well. After about further 1 to 3 minutes, e.g.

2 minutes, a suitable solution (e.g. TM550) is added to increase the total volume to about 1 ml. The protoplasts may be washed once or several times with a suitable medium, e.g. TM550, in order to remove the transformation agent, e.g. PEG, and $Ca^{2+}$ ions. After the washing, the transformed protoplasts may be resuspended in a suitable solution, e.g. PCA (see Table 2 infra).

As mentioned supra, the solid support is preferably a multi-well plate. Accordingly, it is preferred that a plurality of different polynucleotides are immobilized in different wells of the plate, respectively. Preferably, the number of different polynucleotides on the same solid support is at least 2, more preferably at least 6, more preferably at least 12, most preferably at least 24, e.g. 48 or 96. It is important that each polynucleotide is spatially separated from the other polynucleotides. This is of course accomplished if each polynucleotide is immobilized at the bottom of a different well of a multi-well plate.

The polynucleotide is preferably plasmid DNA. The polynucleotide may comprise various nucleic acid sequences encoding different products. Usually, the polynucleotide comprises a nucleic acid sequence encoding a transformation marker. Suitable transformation markers include fluorescent proteins, e.g. red fluorescent protein ("mCherry") or green fluorescent protein (GFP). In another embodiment, the polynucleotide comprises a nucleic acid sequence encoding plant microRNA. In a preferred embodiment, the polynucleotide comprises a nucleic acid sequence encoding a plant microRNA, and a nucleic acid sequence encoding the corresponding target gene. In the most preferred embodiment, the polynucleotide comprises a nucleic acid sequence encoding an artificial microRNA, a nucleic acid sequence representing the target gene of the artificial microRNA, and a nucleic acid sequence encoding a transformation marker. These nucleic acid sequences are preferably present on a single DNA plasmid. Preferred embodiments of the nucleic acid sequences, of the vectors and plasmids that may be used are disclosed infra in respect of the method of screening. These embodiments apply to this first aspect of the invention *mutatis mutandis*.

The DNA uptake method of this invention can be carried out in a fully automated manner. A particular advantage is that the plates having the dried DNA immobilized thereto can be stored and shipped for later use, without loss in transformation efficiency. Another important advantage is that only small amounts of a plasmid are required for foreign polynucleotides uptake.

Monolayer Embedding of Non-Adhesively Growing Cells

In another aspect, this invention relates to an automated method for analyzing cells, comprising the following steps
  providing a culture of non-adhesively growing cells, preferably of plant protoplast cells;
  arranging the cells in a monolayer;
  immobilizing the cells in the monolayer; and
  detecting at least one parameter by microscopic analysis.

The non-adhesively growing cells according to this aspect include animal cells, yeast cells and plant cells. Preferably, the non-adhesively growing cells are plant protoplast cells.

Protoplasts can be isolated and cultured by known methods, see supra. The protoplast culture may be provided in wells of a multi-well plate as described supra with respect to the transformation method of the invention. The protoplasts may or may not be transformed. The protoplasts are then suspended in a suitable immobilization medium which comprises at least one gelling substance. A gelling substance is a substance that can convert a solution into a gel. The conversion from a solution into a gel may require cooling or addition of divalent metal ions such as $Ca^{2+}$. The gelling substance may be a water-soluble polysaccharide. Gelling substances include but are not limited to agar, κ-carrageenan, ι-carrageenan, alginic acid, alginate, agarose, furcellaran, jellan gum, glucono-δ-lactone, azotobactor vinelandii gum, xanthan gum, pectin, guar gum, locust bean gum, tara gum, cassia gum, glucomannan, tragacanth gum, karaya gum, pullulan, gum arabic, arabinogalactan, dextran, sodium carboxymethyl cellulose, methyl cellulose, cyalume seed gum, starch, chitin, chitosan, and curdlan. Preferred gelling substances according to this invention include but are not limited to low melting temperature agarose, agar and alginic acid (ratios and concentrations may vary upon species used, but are preferably $Ca^{2+}$ free).

The immobilization medium preferably contains mannitol and MES (2-[N-morpholino]ethane-sulfonic acid). The concentration of MES may range from 1 mM to about 100 mM, preferably from about 5 mM to about 50 mM, most preferably from about 10 mM to about 20 mM.

The concentration of mannitol in the immobilization medium may range from 10 mM to 1 M, preferably it is from 100 mM to 500 mM. The immobilization medium may further comprise calcium chloride, magnesium chloride and/or magnesium sulfate at suitable concentrations. Preferred immobilization media are disclosed in the examples section.

If alginic acid is used as a gelling substance the immobilization medium should not comprise $Ca^{2+}$ ions. A suitable immobilization medium for alginic acid mediated embedding is described supra. If low melting temperature agarose or agar is used as gelling substance, the immobilization medium may contain calcium ions, e.g. at a concentration from 1 mM to 1 M preferably from 10 mM to 100 mM.

If agarose is used as a gelling substance, the concentration of agarose in the immobilization medium is preferably from 1% (w/w) to 5% (w/w), preferably it is about 2% (w/w). If low melting temperature agarose is used, it is important to maintain the temperature above 30° C., preferably above 35° C. in order to avoid generation of agarose aggregates.

The concentration of alginic acid in the immobilization medium is preferably from 0.5% (w/v) to 5% (w/v), more preferably from 1.5% (w/v) to 3% (w/v).

Next a gravity force is applied to form a cell monolayer at the bottom of the multi-well slide or plate. This can be achieved either by allowing the cells to sediment (passive sedimentation), e.g. for at least 5 minutes, or by centrifugation for at least 30 seconds at 2 g or more, e.g. for 1 min at 10 g (active sedimentation).

The cells are then trapped at the bottom of the solid support (multi-well plate or slide) by solidification of the gelling substance. This may be achieved by lowering the temperature to below 40° C., preferably to below 35° C., preferably to below 30° C. (in case of agar or agarose), or by adding a solution containing at least 10 mM $Ca^{2+}$ salts at the top of the protoplasts mixed with the alginic acid containing medium as microdrops 5 μl or smaller) (in case of alginic acid as gelling substance). If alginic acid is used as a a gelling substance, the gelling is induced by increasing the calcium concentration to at least 1 mM, preferably to at least 50 mM, more preferably to at least 125 mM.

For further culture, a suitable culture medium may be added on top of the gels formed, e.g. to the nominal filling volume of the well. The immobilized protoplast cells can be further cultured in their immobilized state by adding suitable media on top of the solidified protoplast composition. Similarly, the immobilized in that way protoplasts are accessible to exposure of any test substances in this stage, i.e. prior to analysis.

The method according to this aspect of the invention therefore comprises in a specific embodiment the step of contacting the immobilized protoplast cells with a test compound, and determining the effect of the test compound on the protoplast cells. This is preferably done by (i) determining at least one parameter of the cells in the presence of test compound, (ii) determining at least one parameter of the cells in the absence of test compound, and (iii) comparing the parameters determined in (i) and (ii).

The parameters are usually determined by microscopy and include, but are not limited to, fluorescence, morphology and combinations thereof. Methods of microscopy include, but are not limited to, those described in, e.g., Hasek J, Streiblová E. Fluorescence microscopy methods. Methods Mol Biol 53, 391-405 (1996), Ehlert A, Weltmeier F, Wang X, Mayer C S, Smeekens S, Vicente-Carbajosa J, Dröge-Laser W. Two-hybrid protein-protein interaction analysis in *Arabidopsis* protoplasts: establishment of a heterodimerization map of group C and group S bZIP transcription factors. Plant J 46, 890-900 (2006), Bücherl C, Aker J, de Vries S, Borst J W. Probing protein-protein Interactions with FRET-FLIM. Methods Mol Biol 655, 389-399 (2010).

The method of this aspect of the invention is preferably combined with a preceding transformation of the protoplast cells prior to embedding/immobilization. In that embodiment, the method may comprise expression of transformed nucleic acid sequence(s) and determining the effect of that expression on the cells. Preferably, the polynucleotide transformed is one as defined above in respect of the method for introducing polynucleotides into plant protoplast cells according to the first aspect of the invention.

All steps can be carried out in a fully automated manner, e.g. by using pipetting and dispersing robots known in the art.

Any preferred embodiments described supra in respect of the method for introducing polynucleotides into plant protoplast cells can be applied to this aspect *mutatis mutandis*.

mlRNA Screening Method

Yet another aspect of the invention is a screening method to identify efficient plant microRNA sequences, comprising the following steps:
  introducing a plasmid into plant protoplast cells so as to obtain transformed plant protoplast cells, wherein said plasmid comprises a nucleic acid sequence encoding a candidate artificial microRNA, a nucleic acid sequence representing the target gene of the candidate artificial microRNA, and optionally a nucleic acid sequence encoding a transformation marker;
  culturing the transformed plant protoplast cells under conditions that allow expression at least of the nucleic acid sequence encoding the candidate artificial microRNA, and of the nucleic acid sequence representing the target gene of the candidate artificial microRNA;
  selecting as efficient microRNA that candidate artificial microRNA sequence which is capable of efficiently inhibiting expression of the target gene.

The method is preferably carried out in combination with the method for introducing polynucleotides into plant protoplast cells described herein. All embodiments described above apply to this screening method as well.

The screening method uses a vector comprising a nucleic acid sequence encoding a candidate artificial microRNA, a nucleic acid sequence representing the target gene of the candidate microRNA, and a nucleic acid sequence encoding a transformation marker. These components are present on a single vector. This avoids the need for transformation of multiple plasmids or the like. Typical elements of plant transformation plasmids may also be included in the plasmid used in accordance with this invention.

Preferably, the three main elements of the vector, (i) the nucleic acid sequence encoding the candidate artificial microRNA, (ii) the nucleic acid sequence representing the target gene of the candidate microRNA ("the target sequence"), and (iii) the nucleic acid sequence encoding the transformation marker are expressed in the protoplast cell. Efficient expression can be achieved by using a suitable promoter operably linked to the respective nucleic acid sequence. Various promoters can be used. The promoter may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal. Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the Nos promoter, the pEmu promoter, the rubisco promoter, the GRP1-8 promoter and other transcription initiation regions from various plant genes known to those of skill.

The artificial candidate microRNA may be designed on the basis of known design tools, e.g. that described in Ossowski, S., Schwab, R. & Weigel, D. Gene silencing in plants using artificial microRNAs and other small RNAs. *Plant J* 53, 674-690 (2008). However, it surprisingly turned out that only a small fraction of the so designed microRNAs were efficient in silencing the target gene. Thus, there is a need for a screening process in order to identify microRNA sequences which are actually efficient in silencing a given target molecule.

Target sequences may include coding regions and non-coding regions such as promoters, enhancers, terminators, introns and the like. Preferably, target sequences are located within coding regions.

The transformation marker is used to label cells that have been successfully transformed. Suitable transformation markers used in the invention include, but are not limited to, any fluorescent proteins, e.g. those described in Shaner, N. C. et al. Improved monomeric red, orange and yellow fluorescent proteins derived from Discosoma sp. red fluorescent protein. *Nat Biotechnol* 22, 1567-1572 (2004).

The nucleic acid encoding the target sequence is preferably fused to a nucleic acid encoding a marker, e.g. a fluorescent protein such as green fluorescent protein, a luminescent protein such as luciferase, or an enzyme which catalyzes a detectable reaction. This "target marker" can then be detected as a measure of the level of expression of the target sequence. If the target gene is an enzyme, it may be possible that the expression product of the target gene is the target marker itself.

The method thus comprises in a preferred embodiment the steps of:
  determining the expression of the "target marker",
  comparing the level of expression of the target marker to that of a control cell, e.g. a protoplast cell transformed with a control vector comprising a nucleic acid sequence encoding a mock artificial miRNA or with a control vector lacking a nucleic acid sequence encoding the candidate miRNA sequence, and selecting the candidate miRNA sequence as efficient miRNA sequence if the level of expression of the target marker in the cell transformed with the vector encoding the candidate miRNA is significantly lower (e.g. by at least 10%, preferably by at least 25%, more preferably by at least 50%, most preferably by at least 75% or at least 90%) than that in the control cell transformed with the control vector.

The present screening method can be advantageously combined with the other aspects of the invention, namely the method for introducing a polynucleotide into plant protoplast cells, and the immobilization/embedding technique described supra.

A particular embodiment, which is applicable to all aspects of the present invention, includes the use of PCR products for transformation, preferably for transient transformation. In the methods of the invention the polynucleotide or DNA to be transformed may therefore be a PCR product comprising the DNA of interest, preferably a promoter, an open reading frame, and a terminator. The PCR product is directly used for transformation without cloning it into a plasmid or vector. Most preferably, the polynucleotide or DNA to be transformed consists of a promoter, an open reading frame, and a terminator. That is, the PCR product contains substantially no flanking regions. The advantage is that such PCR product will lead to much higher transformation efficiencies than PCR products including flanking regions (see Example 9).

The use of PCR products for transformation is advantageous as it is much faster than the classical cloning approach involving the use of plasmids for transformation. This embodiment is therefore particularly suited for automated methods and high-throughput processes.

EXAMPLES

Figure 1:
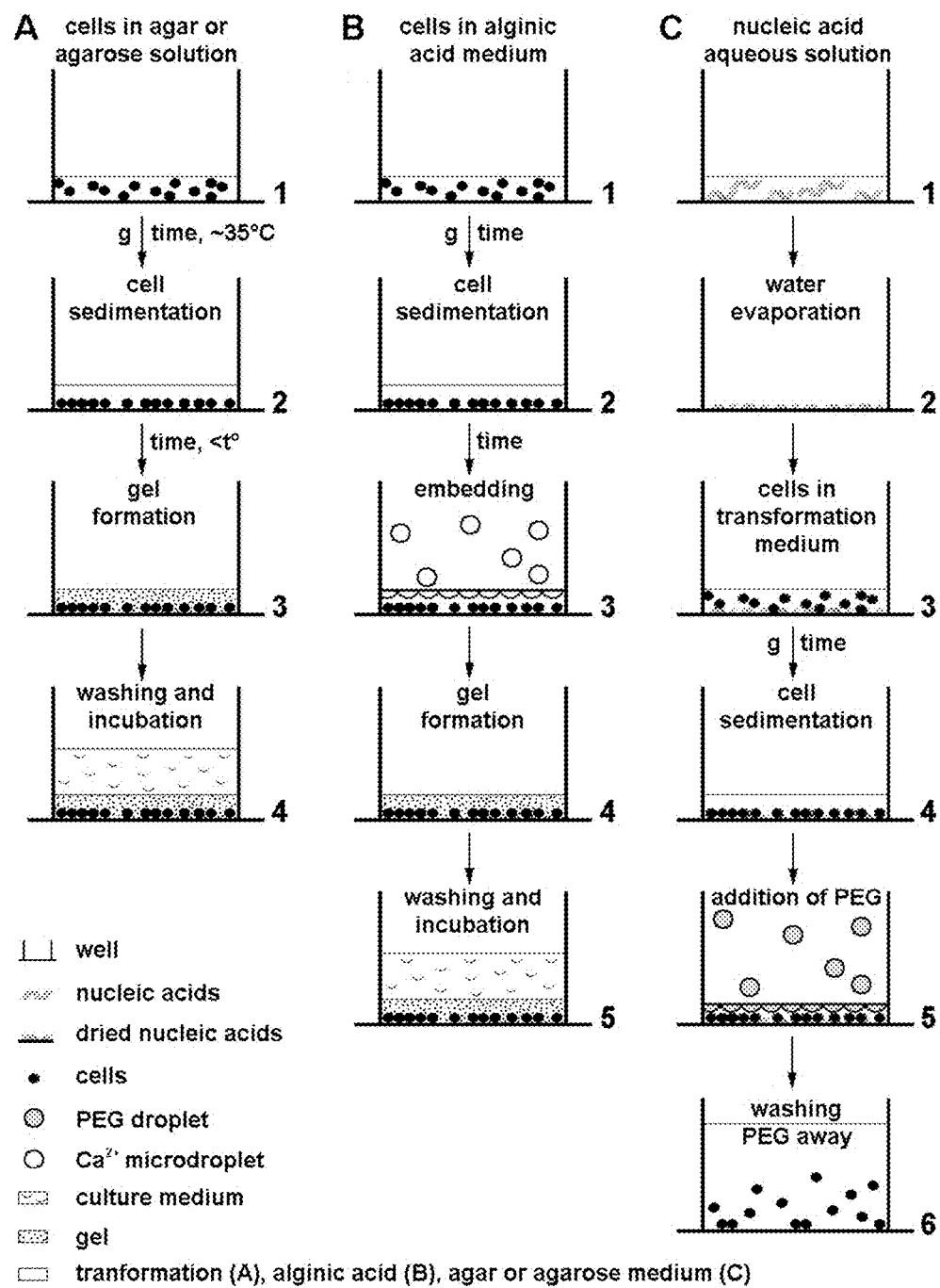
FIG. 1. Illustration of main steps for transient transformation of cells in microwells using dried nucleic acids (A) and for cell immobilisation based on cell sedimentation and subsequent trapping at the bottom of microwells either in alginic acid medium (B) or low melting temperature gelling substances (C).

Some media and solutions used in the examples are listed in the following tables:

TABLE 1

Solutions for protoplast isolation and immobilization. Unit is mM, pH 5.8-5.83 unless indicated otherwise."

| | PEG | Alg-A | W5$^c$ | TM550 | MMC600 | MSC600 |
|---|---|---|---|---|---|---|
| Alginic acid | | 2.8% (w/v) | | | | |
| MES | | 10 mM | | 5 mM | 10 mM | 10 mM |
| CaCl$_2$•2H$_2$0 | | | 125 mM | | 20 mM | 20 mM |
| Ca(NO$_3$)$_2$•4H$_2$0 | 67 mM | | | | | |
| Glucose | | | 5 mM | | | |
| KCl | | | 5 mM | | | |
| MgCl$_2$•6H$_2$0 | | 10 mM | | 15 mM | | |
| MgSO$_4$•7H$_2$O | | 10 mM | | | | |
| Mannitol$^a$ | 270 mM | | 550 mOsm | 550 mOsm | 600 mOsm | |
| NaCl | | | | 150 mM | | |
| Sucrose$^b$ | | | | | | 600 mOsm |
| PEG1500 (g/l) | 384.6 | | | | | |

$^a$approximately 90 g for 1 l of medium give 550 mOsm;
$^b$approximately 165 g for 1 l of medium;
$^c$according to Menczel et al. Effect of radiation dosage efficiency of chloroplast transfer by protoplast fusion in *Nicotiana*. Genetics 100, 487-495 (1982)

TABLE 2

Plant culture, preplasmolysis and culture protoplasts media. Unit is mg/l unless indicated otherwise, pH 5.8-5.83

| | F-PIN$^a$ | F-PCN$^b$ | SCN$^c$ | PCA$^d$ | SCA$^e$ |
|---|---|---|---|---|---|
| KNO$_3$ | 1012 | 1012 | 2527.5 | 2527.5 | 2527.5 |
| CaCl$_2$•2H$_2$O | 640 | 640 | 150 | 450 | 150 |
| MgSO$_4$•7H$_2$O | 370 | 370 | 246.5 | 746 | 1140 |
| KH$_2$PO$_4$ | 170 | 170 | | | |
| NaH$_2$PO$_4$•H$_2$O | | | 150 | 150 | 150 |
| (NH$_4$)$_2$SO$_4$ | | | 134 | 134 | 134 |
| NH$_4$-succinate (mM) | 20 | 20 | | | |
| EDTAFe(III) Na Salt | 40 | 40 | 40 | 40 | 40 |
| KI | 0.83 | 0.83 | 0.75 | 0.75 | 0.75 |

TABLE 2-continued

Plant culture, preplasmolysis and culture protoplasts media.
Unit is mg/l unless indicated otherwise, pH 5.8-5.83

| | F-PIN[a] | F-PCN[b] | SCN[c] | PCA[d] | SCA[e] |
|---|---|---|---|---|---|
| $H_3BO_3$ | 6.2 | 6.2 | 3 | 3 | 3 |
| $MnSO_4 \cdot H_2O$ | 22.3 | 22.3 | 10 | 10 | 10 |
| $ZnSO_4 \cdot 7H_2O$ | 8.6 | 8.6 | 2 | 2 | 2 |
| $Na_2MoO_4 \cdot 2H_2O$ | 0.25 | 0.25 | 0.25 | 0.25 | 0.25 |
| $CuSO_4 \cdot 5H_2O$ | 0.025 | 0.025 | 0.025 | 0.025 | 0.025 |
| $CoCl_2 \cdot 6H_2O$ | 0.025 | 0.025 | 0.025 | 0.025 | 0.025 |
| Inositol | 200 | 200 | 100 | 200 | 100 |
| Pyridoxine-HCl | 2 | 2 | 1 | 2 | 1 |
| Thiamin-HCl | 1 | 1 | 10 | 1 | 10 |
| Ca-panthotenate | 2 | 2 | | 2 | |
| Biotin | 0.2 | 0.2 | | 0.2 | |
| Nicotinic acid | 2 | 2 | 1 | 2 | 1 |
| MES | 976 | 976 | | 976 | |
| Sucrose | 130 | 20 | 20 | | 15 |
| Glucose | | 65 | | 80 | |
| Coconut water (ml) | | | | 20 | |
| BAP | 1 | 1 | | | |
| Dicamba | | | | 4 | |
| NAA | 0.1 | 0.1 | | 0.5 | |
| Agar (g) | | | 8 | | |
| Gelrite (g) | | | | | 2 |

[a,b,c]-according to Dovzhenko et al. (1998) Protoplasma 204, 114-118
[d,e]-according to Dovzhenko et al. (2003) Protoplasma 222, 107-111

TABLE 3

Artificial miRNAs (amiR) and their passenger strands (amiR*)

| | amiR (5'-3') | SEQ ID NO: | amiR* (5'-3') | SEQ ID NO: |
|---|---|---|---|---|
| P1 | TAAGCGAATATATCTCAGCGC | 136 | GCACTGAGATATAATCGCTTT | 137 |
| P2 | TAAGCGAATATATCTCAGGGT | 132 | ACACTGAGATATAATCGCTTT | 133 |
| P3 | TAAATTACCATACATGCCTCT | 128 | AGCGGCATGTATGCTAATTTT | 129 |
| P4 | TTTGGGCGAAAACATCCCTCG | 124 | CGCGGGATGTTTTGGCCCAAT | 125 |
| P5 | TTCGAGTAAATATCGGACGTT | 120 | AAAGTCCGATATTAACTCGAT | 121 |
| P6 | TTCGAGTAAATATCAGACGTT | 116 | AAAGTCTGATATTAACTCGAT | 117 |
| P7 | TTTAAAACTAGAGCCACGCGG | 112 | CCACGTGGCTCTACTTTTAAT | 113 |
| P8 | TAAAGTTAGAGTTCCGACGAC | 108 | GTAGTCGGAACTCAAACTTTT | 109 |
| P9 | TGATTACGAATAAGTTTCCTG | 104 | CAAGAAACTTATTGGTAATCT | 105 |
| P10 | TAAGCGAATATATCTCGGCGC | 100 | GCACCGAGATATAATCGCTTT | 101 |
| P11 | TAACGTGGTAGAAGTGCGCGG | 96 | CCACGCACTTCTAGCACGTTT | 97 |
| P12 | TGATGCCGAATAAACTGGAGC | 92 | GCCCCAGTTTATTGGGCATCT | 93 |
| P13 | TTAGCCGTCATAACGTGGTGG | 88 | CCCCCACGTTATGTCGGCTAT | 89 |
| P14 | TTAGCCGTCATAACGTGGCAG | 84 | CTACCACGTTATGTCGGCTAT | 85 |
| P15 | TTAGCCGTCATAACGTGGTAC | 80 | GTCCCACGTTATGTCGGCTAT | 81 |
| P16 | TAAAGTTAGAGTTCCGACCGC | 76 | GCAGTCGGAACTCAAACTTTT | 77 |
| P17 | TATAATGGCAACATGGGGGGG | 72 | CCACCCCATGTTGGCATTATT | 73 |
| P18 | TATAATGGCAACATGCAGGGG | 68 | CCACTGCATGTTGGCATTATT | 69 |
| P19 | TAACGTGGTAGAAGTCCGCGG | 64 | CCACGGACTTCTAGCACGTTT | 65 |
| P20 | TAAAACTAGAGCCACGTGCCG | 60 | CGACACGTGGCTCAAGTTTTT | 61 |
| P21 | TTATAACGGAACCATAGCCCT | 56 | AGAGCTATGGTTCGGTTATAT | 57 |

TABLE 3-continued

Artificial miRNAs (amiR) and their passenger strands (amiR*)

| | amiR (5'-3') | SEQ ID NO: | amiR* (5'-3') | SEQ ID NO: |
|---|---|---|---|---|
| P22 | TTGATGCCGAATAAACTGCAG | 52 | CTACAGTTTATTCCGCATCAT | 53 |
| P23 | TGATTACGAATAAGTTTCCTC | 48 | GAAGAAACTTATTGGTAATCT | 49 |
| P24 | TCCAAAGTTAGAGTTGCGACG | 44 | CGCCGCAACTCTATCTTTGGT | 45 |
| P25 | TTATAACGGAACCATAGGCCT | 40 | AGACCTATGGTTCGGTTATAT | 41 |
| P26 | TATGATTAAAACTACAGCCGC | 36 | GCAGCTGTAGTTTAAATCATT | 37 |
| P27 | TATAATGAAACCTCCCAGGTC | 32 | GAACTGGGAGGTTACATTATT | 33 |
| P28 | TTTAAAACTAGAGCGACGCGG | 30 | CCACGTCGCTCTACTTTTAAT | 31 |
| P29 | TAAATTACCATACATGCCTTT | 26 | AACGGCATGTATGCTAATTTT | 27 |
| P30 | TATGACGGCAGGTCGAACGAG | 22 | CTAGTTCGACCTGGCGTCATT | 23 |
| P31 | TTTACCGAAACTAAACTGCTC | 18 | GAACAGTTTAGTTACGGTAAT | 19 |
| P32 | TTTGGGCGAAAACATCCCTGC | 14 | GCCGGGATGTTTTGGCCCAAT | 15 |
| P33 | TACGATTTGAACCATGAGGCC | 10 | GGACTCATGGTTCTAATCGTT | 11 |
| P34 | TAACGGTTTATGCCGCAGCGT | 8 | ACACTGCGGCATATACCGTTT | 9 |
| P35 | TGTTGGGCGAAAACATCCGTG | 4 | CAAGGATGTTTTCCCCCAACT | 5 |
| P36 | TAATATCAGACCTTGGAGCGT | 138 | ACACTCCAAGGTCAGATATTT | 139 |
| P37 | TCCAAAGTTAGAGTTCCGACG | 134 | CGCCGGAACTCTATCTTTGGT | 135 |
| P38 | TTTATGGGCAACGCGACCGAC | 130 | GTAGGTCGCGTTGGCCATAAT | 131 |
| P39 | TAACGGTTTATGCCCGAGCGT | 126 | ACACTCGGGCATATACCGTTT | 127 |
| P40 | TAATATCAGACCTTCAAGCGT | 122 | ACACTTGAAGGTCAGATATTT | 123 |
| P41 | TATGACTAGAGTGTTGCGGGG | 118 | CCACGCAACACTCAAGTCATT | 119 |
| P42 | TTAGTTGGAAGGTCTCGGACT | 114 | AGCCCGAGACCTTGCAACTAT | 115 |
| P43 | TTCGTTACTATTCCCCTGACG | 110 | CGCCAGGGGAATACTAACGAT | 111 |
| P44 | TTTATGGGCAACGCGGTCGAC | 106 | GTAGACCGCGTTGGCCATAAT | 107 |
| P45 | TATGACGGCAGGTCGAACGGC | 102 | GCAGTTCGACCTGGCGTCATT | 103 |
| P46 | TGAAGAGTTATGGGCAACGGG | 98 | CCAGTTGCCCATATCTCTTCT | 99 |
| P47 | TGTGGAGTAATCGGCGTGCTG | 94 | CAACACGCCGATTTCTCCACT | 95 |
| P48 | TATGACTAGAGTGTTCGGGGG | 90 | CCACCGAACACTCAAGTCATT | 91 |
| P49 | TGAAGAGTTATGGGCGACCCG | 86 | CGAGTCGCCCATATCTCTTCT | 87 |
| P50 | TAGATTCGAAGGTCTACGTCT | 82 | AGCCGTAGACCTTGGAATCTT | 83 |
| P51 | TAACGTGGTAGAAGTCCCGCG | 78 | CGAGGGACTTCTAGCACGTTT | 79 |
| P52 | TTCGAGTAAATATCAGGCCCT | 74 | AGAGCCTGATATTAACTCGAT | 75 |
| P53 | TGTTGGGCGAAAACGTCCGTG | 70 | CAAGGACGTTTTCCCCCAACT | 71 |
| P54 | TAAAGTTAGAGTTCGGACCGC | 66 | GCAGTCCGAACTCAAACTTTT | 67 |
| P55 | TAACGTGGTAGAAGTGCGCGG | 62 | CCACGCACTTCTAGCACGTTT | 63 |
| P56 | TGGAAAGAGAGGAGTGGGACG | 58 | CGCCCCACTCCTCACTTTCCT | 59 |
| P57 | TGGACGGCGAAGACGGCGACA | 54 | TGCCGCCGTCTTCCCCGTCCT | 55 |
| P58 | TGTCATCACACTTGTTGGCGG | 50 | CCACCAACAAGTGAGATGACT | 51 |
| P59 | TTGAAGTGGAAAGACAGGACT | 46 | AGCCCTGTCTTTCGACTTCAT | 47 |

TABLE 3-continued

Artificial miRNAs (amiR) and their passenger strands (amiR*)

| | amiR (5'-3') | SEQ ID NO: | amiR* (5'-3') | SEQ ID NO: |
|---|---|---|---|---|
| P60 | TTCCGGAGCATTGGTCGGGAG | 42 | CTACCGACCAATGGTCCGGAT | 43 |
| P61 | TACTGAACATAGCCATGCCTA | 38 | TAAGCATGGCTATCTTCAGTT | 39 |
| P62 | TTGAAGTGGAAAGAGACGACT | 34 | AGCCGTCTCTTTCGACTTCAT | 35 |
| GFP-6 | TTCTGGTAAAAGGACAGGGCC | 28 | GGACCTGTCCTTTAACCAGAT | 29 |
| GFP-7 | TTAATGATCAGCGAGTTGCAC | 24 | GTACAACTCGCTGTTCATTAT | 25 |
| GFP-9 | TTGTATTCCAACTTGTGGCCG | 20 | CGACCACAAGTTGCAATACAT | 21 |
| GFP-10 | TGATCAGCGAGTTGCACGCCG | 16 | CGACGTGCAACTCCCTGATCT | 17 |
| GFP-11 | TTGACTTCAGCACGTGTCTTG | 12 | CACGACACGTGCTCAAGTCAT | 13 |
| mock | TATCATAAGAGCAGGTCCTGA | 6 | TCCGGACCTGCTCATATGATT | 7 |

Example 1. Monolayer Embedding of Tobacco Leaf Protoplasts for Vontinuous Cell Tracking Wholly expanded leaves from 3-4 weeks old tobacco plant cultures (*Nicotiana tabacum* cv. Petite Havana) were used for protoplast isolation. Two leaves were cut in stripes 1-2 mm in width and preplasmolysed for 1 h in 10 ml of F-PIN medium as described in Dovzhenko et al. (1998) Protoplasma 204, 114-118. Preplasmolysis medium was replaced with 10 ml of fresh F-PIN supplemented with Cellulase Onozuka R-10 (DUCHEFA) and Macerozyme Onozuka R-10 (DUCHEFA) 0.25% each. Digestion was performed overnight (14 h) in the dark. Digestion medium was further filtered through 100 μm sieves in 12 ml tube (Greiner, Germany) to remove non-digested tissues. Afterwards 2 ml of TM550 were overlaid on a top of filtered F-PIN containing protoplasts. Intact protoplasts were collected from the interlayer between TM550 and protoplast/digestion mixture after 10 min flotation at 100 g and transferred to a new tube. Total volume was adjusted to 10 ml with W5 medium and protoplast number was estimated. Protoplasts were further pelleted for 5 min at 100 g and supernatant was discarded. After the last centrifugation step protoplast pellet was mixed with TM550 to achieve density of $2 \times 10^4$ cells per 1 ml. Protoplasts/TM550 mixture was further mixed at ratio 1:1 with Alg-A medium for $Ca^{2+}$-alginate embedding or with TM550 containing 2% of low melting temperature agarose for agarose embedding. It is important to maintain temperature above 30° C. (recommended 35° C.) until formation of a cell layer at a well bottom and to avoid generation of agarose aggregates.

Figure 2:
FIG. 2. Alginate matrix formation after adding microdroplets of W5.
Figure 3:
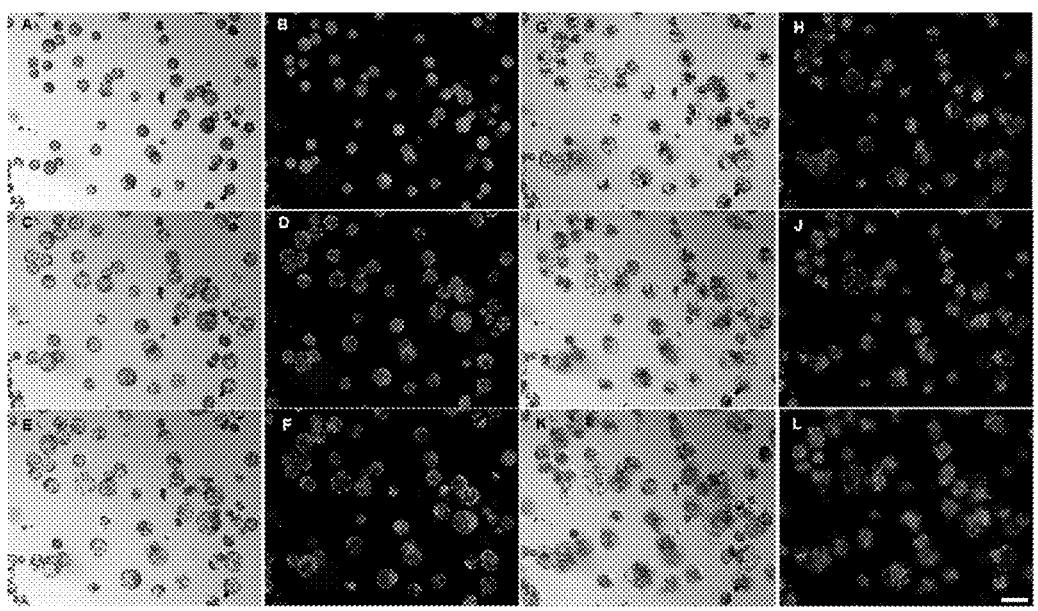
FIG. 3. Development of tobacco leaf protoplasts using PME. Bright field (A, C, E, G, I, K) and chlorophyll autofluorescence channel (B, D, F, H, J, L) images were acquired with 24 h interval after embedding (A, B). Scale bar=60 µm.
Figure 4:
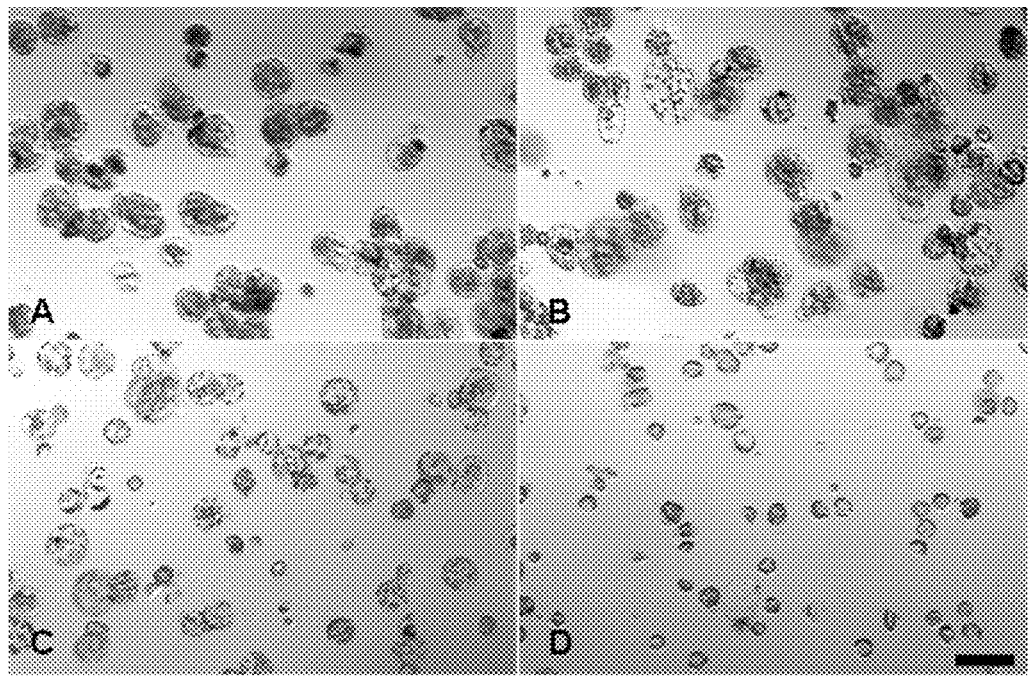
FIG. 4. Effect of compound R113 do we need to disclose this compound as this will be subject of another patent application to be filed soon, Alternative: kinase inhibitor? on tobacco leaf protoplast development after 6 days of culture. Normal development of protoplasts cultured in F-PCN medium (A) or in F-PCN with 1 µm of R113 (B). Inhibition of cell divisions and colony formation in F-PCN medium supplemented with 10 µM of R113 (C), complete inhibition of cell division and cell death in F-PCN supplemented with 25 µM of R113 (D). Scale bar=60 µm.

For cell immobilisation using low melting temperature agarose 100 μl or 200 μl of protoplast embedding mixture per were transferred into 96-well plates or 8-well slides respectively (FIG. 1A 1). After formation of cell layers at 30-35° C. achieved either by centrifugation for at least 1 min at 10 g or by sedimentation for at least 20-30 min (FIG. 1A 2) plates can be placed at room temperature for agarose solidification (FIG. 1A 3). Embedded cells should be washed twice for 15 min with the culture F-PCN medium and 200 μl of fresh F-PCN were added after the last washing (FIG. 1A 4). It is important to note, that within first 24 h of culture mild expansion of agarose gel with embedded cells was not avoidable due to long lasting water uptake from the culture medium.

Figure 5:
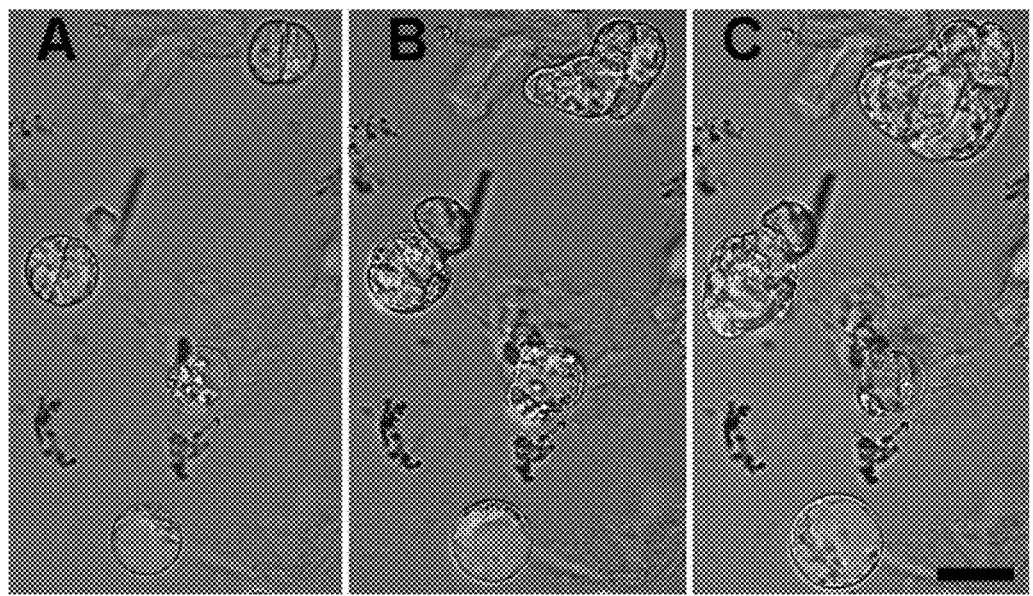
FIG. 5. Tracking of developing protoplasts from *Arabidopsis* seedlings. Images were acquired after 24 h (A), 48 h (B) and 96 h of culture using the PME-technique. Scale bar=40 µm.

For cell immobilisation using $Ca^{2+}$-alginate embedding 100 μl or 200 μl of protoplast embedding mixture per were transferred into 96-well plates or 8-well slides respectively (FIG. 1B 1). To form a cell layer protoplasts could be either centrifuged at 10 g for at least 1 min or sedimented for at least 20-30 min (FIG. 1B 2). Afterwards the upper surface of the protoplast embedding mixture was covered with 20 μl or 40 μl for 96-well plates or 8-well slides respectively of W5 or another osmotically adjusted solution with a high $Ca^{2+}$-salt 20 mM) content in a form of micro-droplets 1 μl droplets if manually or 100-500 nl droplets if using dispersing robots, FIG. 1B 3, FIG. 2). After 5 min final volume of W5 medium was adjusted to 200 μl and after additional at least 15 min cell immobilisation was achieved (FIG. 1B 4). W5 medium was replaced with 200 μl of the culture F-PCN medium for washing. After two washings, 200 μl of fresh F-PCN were added for subsequent protoplast culture (FIG. 1B 5). Embedded cells were observed with 24 h interval and their development was documented by imaging of the same area using inverted microscope (Axiovert 200M, Zeiss) for a period of 1 week (FIG. 3). Due to formation of a single cell layer at the bottom of culture wells and subsequent immobilization this technique was named protoplast-monolayer-embedding technique (PME).

Example 2. Effect of R113 Compound on Development of Tobacco Leaf Protoplasts

Protoplast isolation was done as described in the example 1 prior the washing with the culture medium. Cell immobilisation was performed in 8-well slides (IBIDI). After the removal of W5 medium, F-PCN with various concentration of compound R113 per well was used for washing and further cell culture. Analysis of cell division efficiency (FIG. 4) was performed using inverted microscope (Axiovert 200M, Zeiss).

Example 3. Monolayer Embedding of *Arabidopsis* Protoplasts for Continuous Cell Tracking

*Arabidopsis* protoplasts were isolated from hypocotyls of 7-days old *Arabidopsis* seedlings (Col-0) germinated on SCA medium according to Dovzhenko et al. (2003) Protoplasma 222, 107-111. Explants were cut in 0.5-1 mm fragments and preplasmolysed in MMC600 for 1 h. Afterwards the medium was substituted with fresh MMC600 supplemented with 0.5% Cellulase Onozuka R-10 (DUCHEFA), 0.5% Macerozyme Onozuka R-10 and 0.05% Driselase (SIGMA). After 14 h of digestion, protoplast containing medium was filtered through 32 µm sieves. Protoplasts containing medium was further mixed with an equal volume of TM550 and collected by centrifugation for 10 min at 100 g. Supernatant was removed and the pellet was mixed with TM550:Alg-A mixture (1:1) to achieve density $1 \cdot 10^4$ protoplasts per 100 µl. 100 µl aliquots of protoplast embedding mixture were transferred in 96-well plate and immobilized as described in the example 1. After the removal of W5 medium, PCA medium was used for washing and culture steps. Cell observations (FIG. 5) were done using inverted microscope (Axiovert 200M, Zeiss).

Example 4. Analysis of Promoter Activity Using Monolayer Embedding

Figure 6:
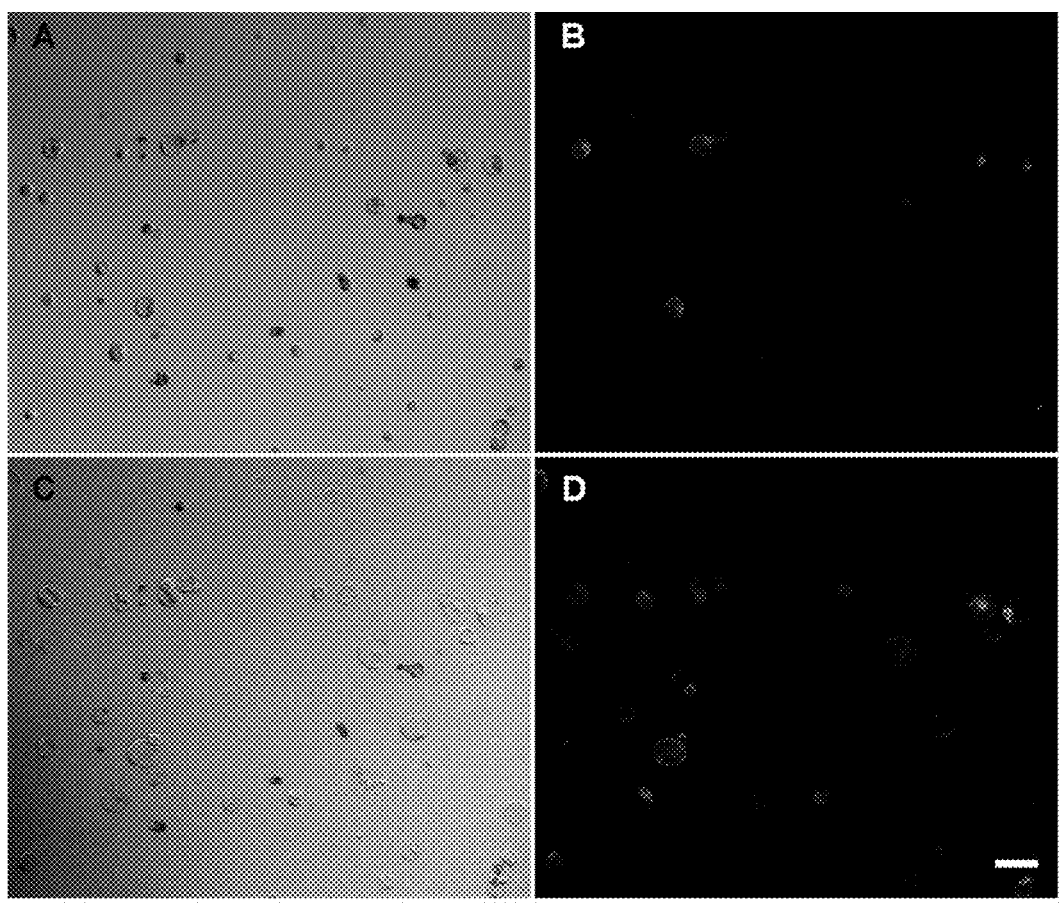
FIG. 6. Immobilization of protoplasts from DR5-GFP *Arabidopsis* marker line. Bright field (A,C) and GFP channel (B,D) images were acquired right after immobilization (A,B) and after 72 h of culture (C,D) demonstrating an increase in promoter activity in cells at later time point. Scale bar=40 µm.

Cotyledons from 7-days old *Arabidopsis* seedlings (DR5-GFP line, Col-0 background) were removed and cut in 0.5-1 mm fragments. Preplasmolysis and digestion was performed as describe in the example 3, however no Driselase was used for digestion. After filtration through 56 µm sieves, protoplasts were collected in 12 ml tube and pelleted for 10 min at 100 g. Supernatant was discarded and 10 ml of MSC600 was added. For flotation 2 ml of TM550 were overlayed on a top of MSC600 and centrifuged for 10 min at 100 g. Interlayer was collected and transferred into a new 12 ml tube. Total volume was adjusted to 10 ml with W5 medium. Protoplasts were washed for 5 min at 50 g and afterwards pellet was resuspended in TM550 to achieve density $2 \cdot 10^4$ protoplasts per 100 µl. After mixing 1:1 with Alg-A medium, 100 µl aliquots of protoplast embedding mixture were used for cell immobilisation in 96-well plates. Immobilisation and subsequent culture procedure were performed as described in example 3. While GFP fluorescence was detected only in 3% of freshly isolated protoplasts, it was observed in over than 95% of intact cells after 48 h of culture thus demonstrating activity of DR5 promoter (FIG. 6).

Example 5. Transient Transformation of *Arabidopsis* Shoot Protoplasts Using Dried DNA Purified plasmid DNA was dissolved in ultra-pure sterile water. Aliquots of aqueous DNA solution at various concentrations (0, 0.1, 0.5, 1 and 5 µg per 10 µl) were transferred inside 96-well plate (ABIGene). Water evaporation took place under the sterile bench overnight (FIG. 1C 1,2). After complete evaporation plates could be used either immediately or stored at −20° C.

Figure 7:
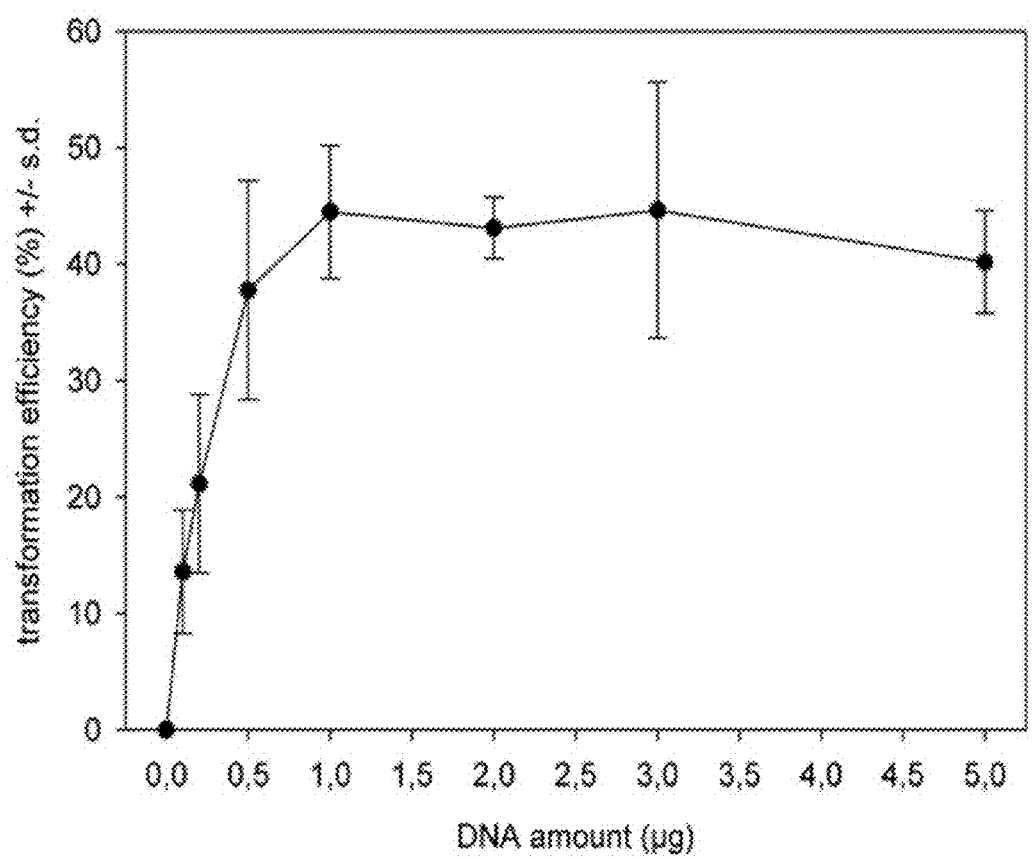
FIG. 7. Efficiency of transient transformation of *Arabidopsis* leaf protoplasts using dried DNA (FIG. 14, Table 3). Expression of mCherry protein driven under control of the rolD promoter was estimated after 24 h. Data represents mean values of three independent experiments, error bars indicate standard deviation.

*Arabidopsis* shoots from 3-weeks old seedlings (Col-0) were used. Digestion and isolation were performed as described in example 4. After last washing step cell density was adjusted to $1 \times 10^5$ and aliquots of 30 µl were transferred into the wells containing dried DNA (FIG. 1C 3). Afterwards cells were left to sediment for at least 2 min (FIG. 1C 4). Alternatively, protoplasts could be centrifuged for 1 min at 10 g. Further PEG-mediated DNA uptake was performed by adding an equal volume of 40% PEG1500 solution to protoplasts in wells (FIG. 1C 5). After 8 min of the PEG treatment, a half of the total volume of TM550 was added and after additional 2 min total volume was increased to 1 ml using TM550 (FIG. 1C 6). To avoid formation of protoplast-aggregates, well contents were mixed using 1 ml 8-well pipette. Sedimentation for at least 30 min was performed to collect cells. Alternatively, protoplasts could be centrifuged for 10 min at 50 g. Supernatant (950 µl) was discarded and protoplast pellet was resuspended in 300 µl of PCA. Transformation efficiencies (FIG. 7) were estimated after 30 hours using inverted microscope (Axiovert 200M, Zeiss).

Co-transformation with at least two (or more) either plasmids or PCR amplified fragments was performed. Plasmids carrying expression cassette of GFP or endoplasmic reticulum-mCherry were either mixed and dried upon water evaporation under a sterile bench inside 96-well plates or mixed and used directly for transformation. Transformation was carried out as described above. Equal amount of each plasmid was used (0.5 µg per plasmid). To simulate a simple pipetting robot, all manipulations (adding cells, adding reagents prior washing step after transformation) were performed by using multichannel pipette. Cells were added directly to wells containing either dried DNA or DNA dissolved in water and no further mixing was performed prior adding PEG1500 solution. Comparison of transformation and co-transformation efficiencies was performed after 24 h. Images were acquired using iMIC (TILL Photonics, Germany) automated microscope, and image analysis was performed using ImageJ free software. At least 250 cells per individual transformation were analysed (Table 4).

TABLE 4

Analysis of GFP and ER-mCherry co-transformation efficiencies using dried DNA or DNA dissolved in water. Each line represents one transformation experiment.

| Co-transformed cells out of all transformed, % | | Co-transformed cells out of all cells, % | |
|---|---|---|---|
| Dried DNA | DNA in solution | Dried DNA | DNA in solution |
| 92.41 | 88.0 | 20.33 | 6.1 |
| 85.15 | 86.0 | 12.76* | 5.9 |
| 94.12 | 85.7 | 21.05 | 7.2 |
| 92.31 | 91.6 | 20.47 | 13.9 |
| 91.39 | 88.4 | 19.11 | 13.4 |
| 92.41 | 84.6 | 18.31 | 17.6 |
|  | 96.2 |  | 34.2 |
|  | 93.5 |  | 42.1 |
|  | 87.7 |  | 31.2 |

Figure 8:
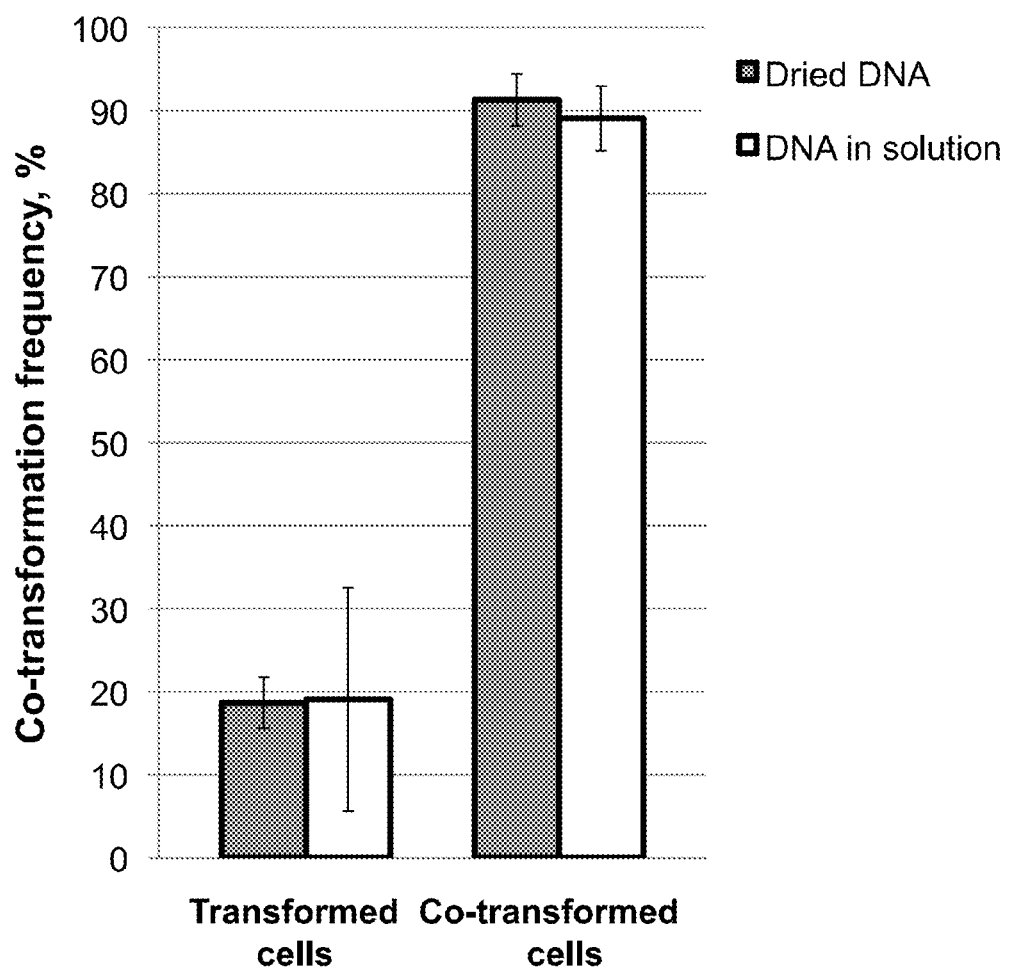
FIG. 8. Co-transformation of *Arabidopsis* protoplasts using dried and dissolved DNA.

*wrong amount of PEG (~½ of required volume) was added during this transformation, due to defect of pipette's channel Significant variation of co-transformation efficiencies was observed using DNA dissolved in water, while using dried DNA approach highly reproducible results could be obtained (FIG. 8). This criteria is essential for automation of the whole procedure.

Example 6. Transient Transformation of Tobacco Leaf Protoplasts Using Dried DNA in Combination with Continuous Cell Tracking Plasmid DNA aliquots (1 µg per 10 µl of ultrapure water) were dried as described in the example 5 (FIG. 1C).

Figure 9:
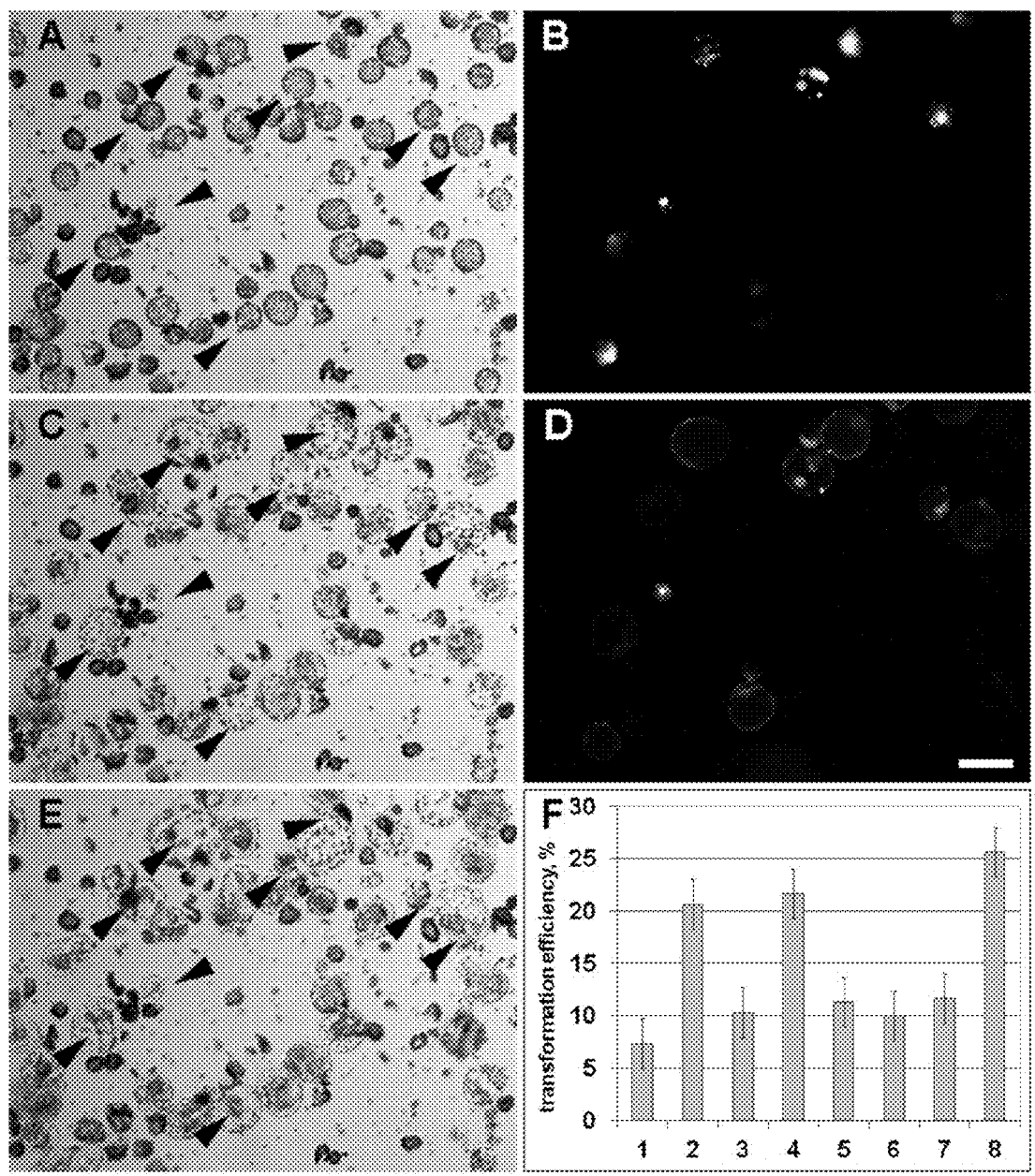
FIG. 9. Transient transformation of tobacco leaf protoplasts using dried DNA. Effect of transient expression of 35S::PIN8-Venus (FIG. 15) construct on protoplast development (A-E). Arrow heads in bright field images (A, C, E) mark positions of transiently transformed cells identified in YFP channel (B, D) after 24 h (A,B), 96 n (C,D) and 144 h (E) of culture. Scale bar=60 µm. Efficiency of transient transformation of tobacco protoplasts using dried plasmid DNA: 1-1 µg of 35S::Venus, 2-2 µg of 35S::Venus (FIG. 16), 3-1 µg of 35S::ER-YFP, 4-2 µg of 35S::ER-YFP, 5-2 µg of 35S::Golgi-YFP, 6-2 µg of 35S::PIN1-Venus, 7-1 µg of 35S::PIN8-Venus, 8-2 µg of 35S::PIN8-Venus. All constructs except of PIN1 and PIN8 tagged with yellow fluorescent protein Venus were taken from Nelson et al. A multicoloured set of in vivo organelle markers for co-localization studies in *Arabidopsis* and other plants. Plant J 51, 1126-1136 (2006). Data represents mean values of three independent experiments, error bars indicate standard deviation.
Figure 10:
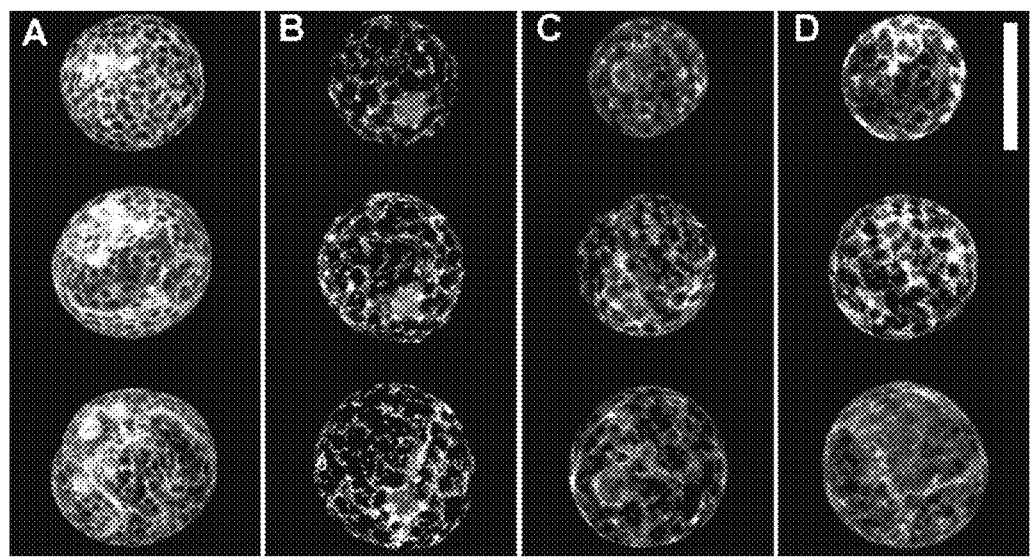
FIG. 10. Tracking and 3D reconstructions of developing tobacco protoplasts after the PME immobilization. Image were acquired with 24 h interval starting 24 h after PEG mediated DNA uptake. Different subcellular compartments where visualised using subcellular markers translationaly fused to fluorescent proteins: cytoplasmic YFP (A), mitochondrial YFP (B), endoplasmatic reticulum mCherry (C) and tonoplast mCherry (D). All constructs were taken from Nelson et al. A multicoloured set of in vivo organelle markers for co-localization studies in *Arabidopsis* and other plants. Plant J 51, 1126-1136 (2006). Scale bar=40 µm FIG. 11. Knock-down of a stable reporter gene (GFP) by artificial microRNAs (FIG. 14, Table 3). Mean absolute GFP pixel intensity of transformed cells over time (57±20 cells per sample per day).

Tobacco leaf protoplasts were isolated as described in the Example 1 prior the embedding procedure. After protoplast pelleting in W5 medium and removal of the supernatant, cell density was adjusted to $2 \cdot 10^6$ cells/ml with TM550. Aliquots of 30 µl ($2$-$2.5 \cdot 10^5$ cells) were transferred into the wells using 8-channel pipette. Afterwards cells were left to sediment for at least 2 min. Alternatively, protoplasts could be centrifuged for 1 min at 10 g. Further PEG-mediated DNA uptake was performed by adding an equal volume of 40% PEG1500 solution to protoplasts in wells. After 8 min of the PEG treatment, a half of the total volume of TM550 was added and after additional 2 min total volume was increased to 1 ml using TM550. To avoid formation of protoplast-aggregates, well contents were mixed using 1 ml-tip pipette. Sedimentation for at least 30 min was performed to collect cells. Alternatively, protoplasts could be centrifuged for 10 min at 50 g. Supernatant (950 µl) was discarded and protoplast pellet was resuspended in 250 µl of TM550. Protoplasts were further mixed with Alg-A medium for embedding. Embedding was further performed as described in the example 1 (FIG. 1B). After the embedding transformation efficiencies, protein localisation and effect of gene expression was analysed using automated inverted microscope (iMIC or MORE, TILL Photonics, FIG. 9) and confocal laser scanning microscope (LSM5META, Zeiss, FIG. 10).

Example 7. RNAi-Mediated Gene Knock-Down Using Artificial miRNAs

Figure 11:
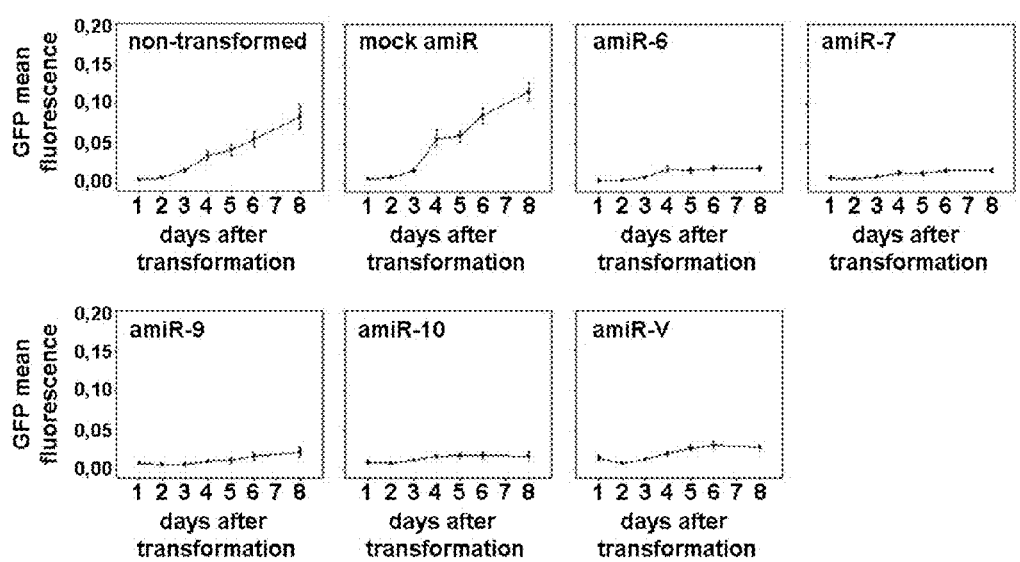

*Arabidopsis* shoots from 3-weeks old seedlings (35S::GFP in Col-0 background) were used. Digestion and isolation were performed as described in example 4. After last washing step cell density was adjusted to $1 \cdot 10^5$ and aliquots of 30 µl were transferred into 96-well plate. 1-2 µg DNA in 5 µl of ultra-pure sterile water was mixed with protoplasts. PEG-mediated DNA uptake was performed by adding an equal (35 µl) volume of 40% PEG1500 solution. After 8 min of the PEG treatment, a half of the total volume of TM550 was added and after additional 2 min total volume was increased to 1 ml using TM550. After careful mixing with 1 ml pipette for separation of protoplast aggregates, sedimentation for at least 30 min was performed to collect cells. Supernatant (950 µl) was discarded and protoplast pellet was resuspended in 75 µl of TM550. Protoplasts were further mixed with Alg-A medium for embedding. Embedding and subsequent culture were performed as described in the example 3. Effect of artificial miRNA (amiRNA) on gene expression (FIG. 11) was analysed for a period of 6 days using automated inverted microscope (Axiovert 200M, Zeiss).

Example 8. Screening of Artificial miRNA Efficiency

Figure 12:
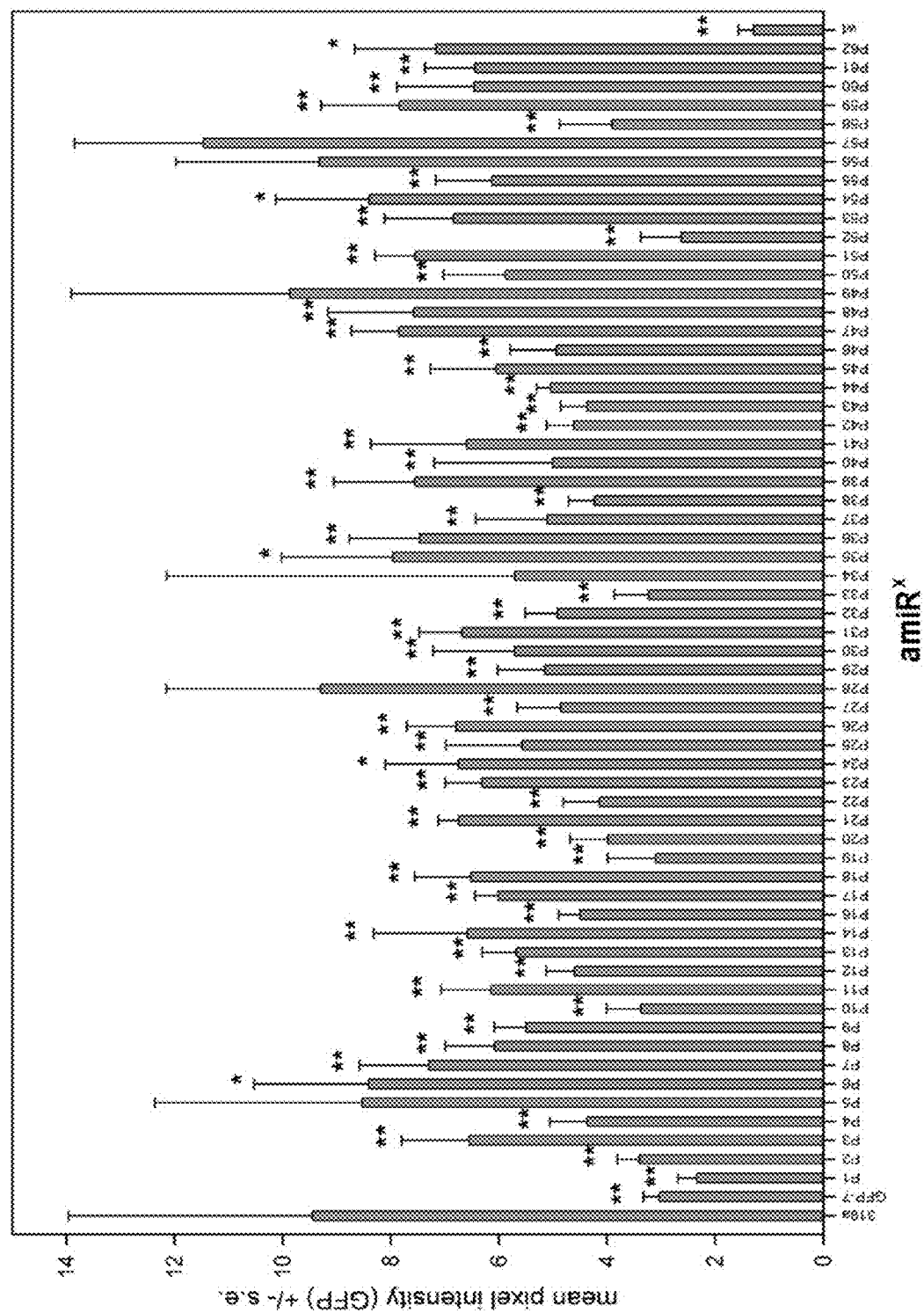
FIG. 12. Validation of artificial microRNAs efficiency by knock-down of the transiently expressed target gene, PIN1, translationally fused with the GFP (FIG. 14, Table 3). Transformed cells express the marker mCherry, PIN1:: mGFP5 and an amiRNA; wt represents cells expressing only mCherry. Images were taken 2 days after transformation, asterisks indicate significant (*, p<0.05) or highly significant (**, p<0.0005) difference to miR$^{319}$a sample; bars represent median pixel intensity values of the respective cell population; error bars correspond to standard error.
Figure 13:
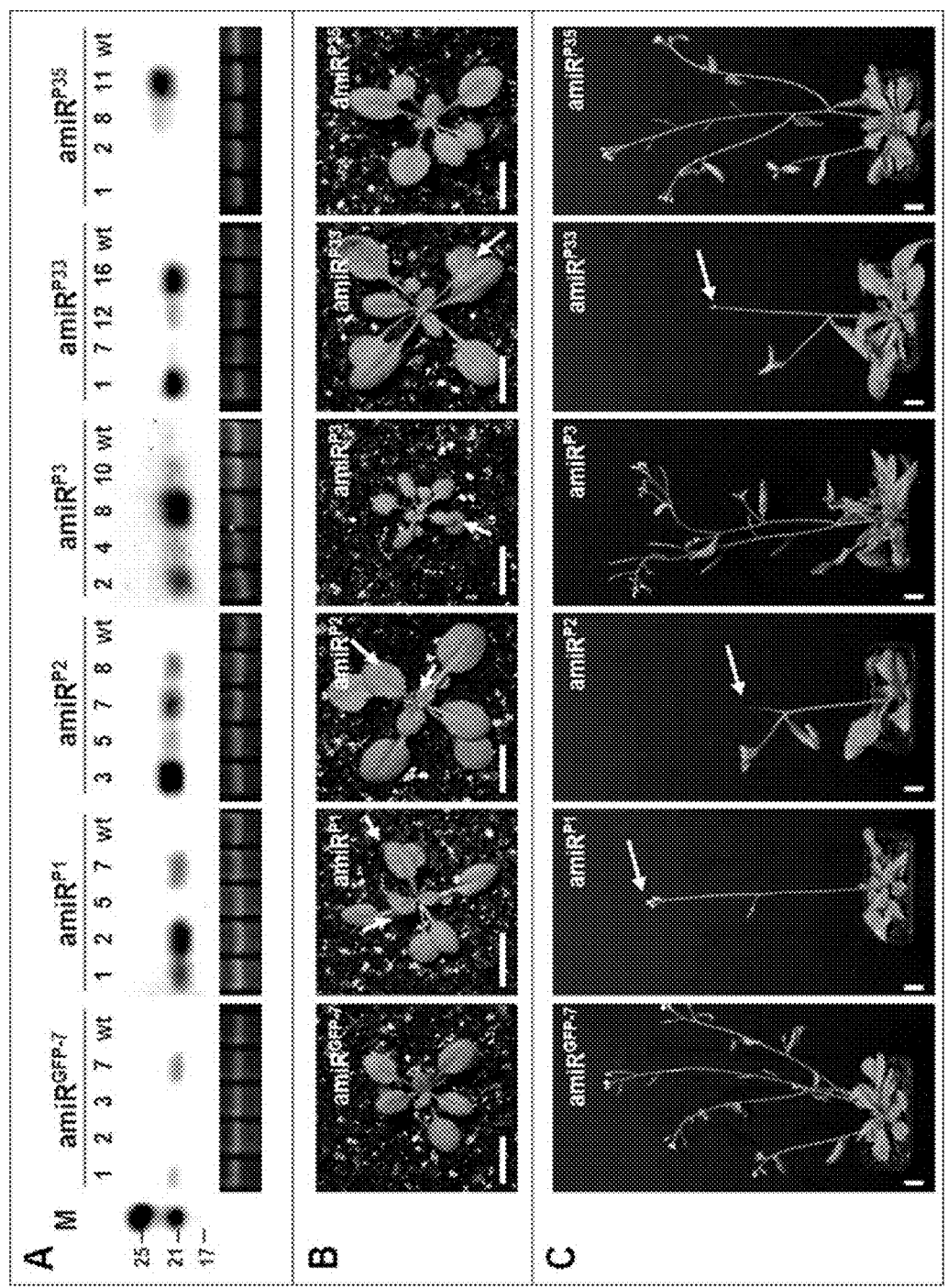
FIG. 13. Expression of amiR$^{PIN1}$ in stable transgenic lines (Col-0 wild-type background). A: Northern Blot analysis shows expression and processing of amiRNAs in several independent lines (upper panel). 5S rRNA serves as loading control (lower panel). DNA oligonucleotides antisense to the respective amiRNA and end-labelled with γ-ATP were used as probes. B-C: Representative phenotypes observed among independent lines transformed with the same construct. B: Altered phyllotaxis pattern of rosette leaves (arrows) in plants expressing amiR$^{P1}$, amiR$^{P2}$, amiR$^{P3}$ and amiR$^{P33}$ 2 weeks after germination; scale bar=10 mm. C: Altered shoot phyllotaxis and pint-like shoot phenotypes (arrows) in lines expressing amiR$^{P1}$, amiR$^{P2}$ and amiR$^{P33}$ (scale bar=10 mm).
Figure 14:
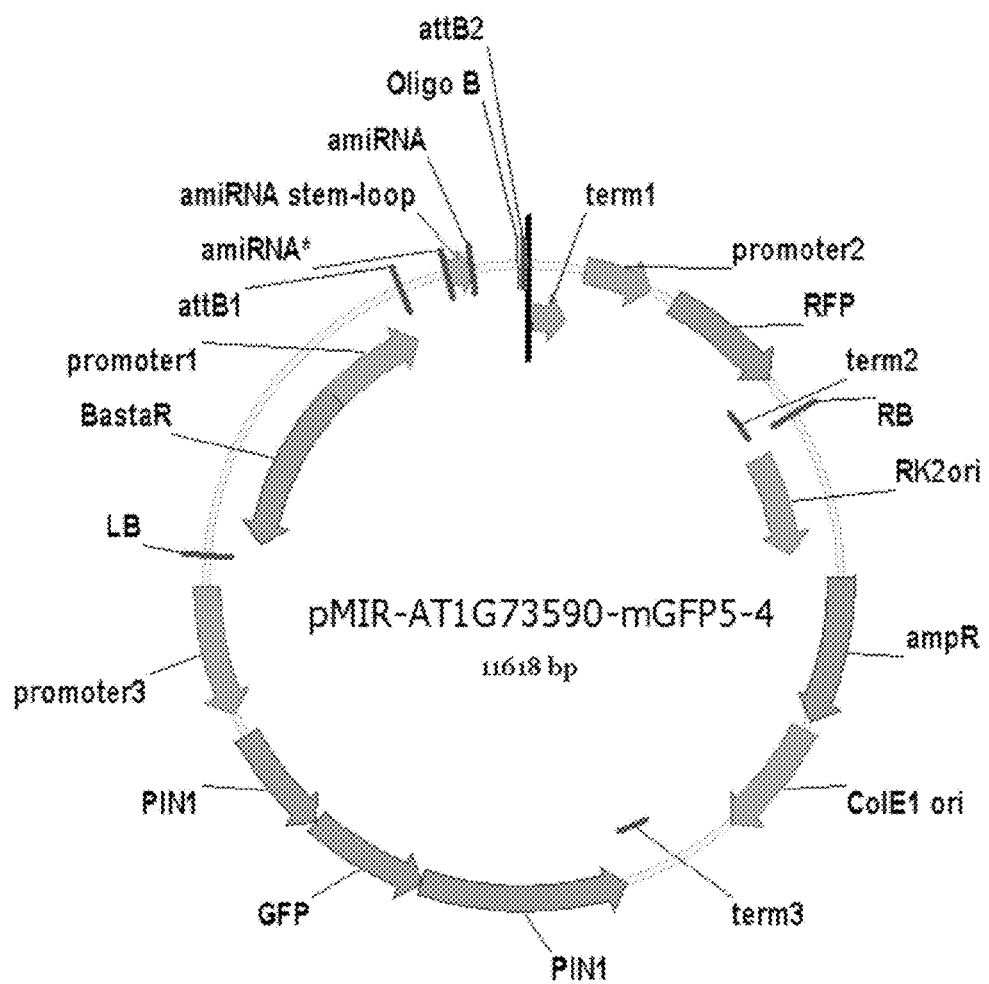
FIG. 14. Map of amiRNA screening vector pMIR-AT1G73590-mGFP5-4 consisting of three screening elements under corresponding regulatory elements: the amiRNA gene (amiRNA and passenger amiRNA* sequences could be substituted according to Table 3), the target gene PIN1 fused to the reporter marker GFP (this expression element was present for the example 8, but not for the example 7) and the transformation marker mCherry. The nucleotide sequence of pMIR-AT1G73590-mGFP5-4 is shown in SEQ ID NO:1.

*Arabidopsis* shoots from 3-weeks old seedlings (Col-0) were used. Digestion, isolation, and culture procedures were performed as described in example 5. Transformation was performed as described in the example 7. Efficiencies of amiRNAs were estimated as a read-out of fluorescence intensity of the target gene translationally fused with the reporter gene (FIG. 12). Randomly selected amiRNA constructs were further used for generation of transgenic plants which exhibited phenotypes confirming microscopy-based conclusions on amiRNA efficiency (FIG. 13).

Example 9. Cloning Free Screening Approach in Plant Cells

Experiment 1. Transient Transformation and Co-Transformation Using PCR Product Transient Transformation (PPTT)

Figure 17:
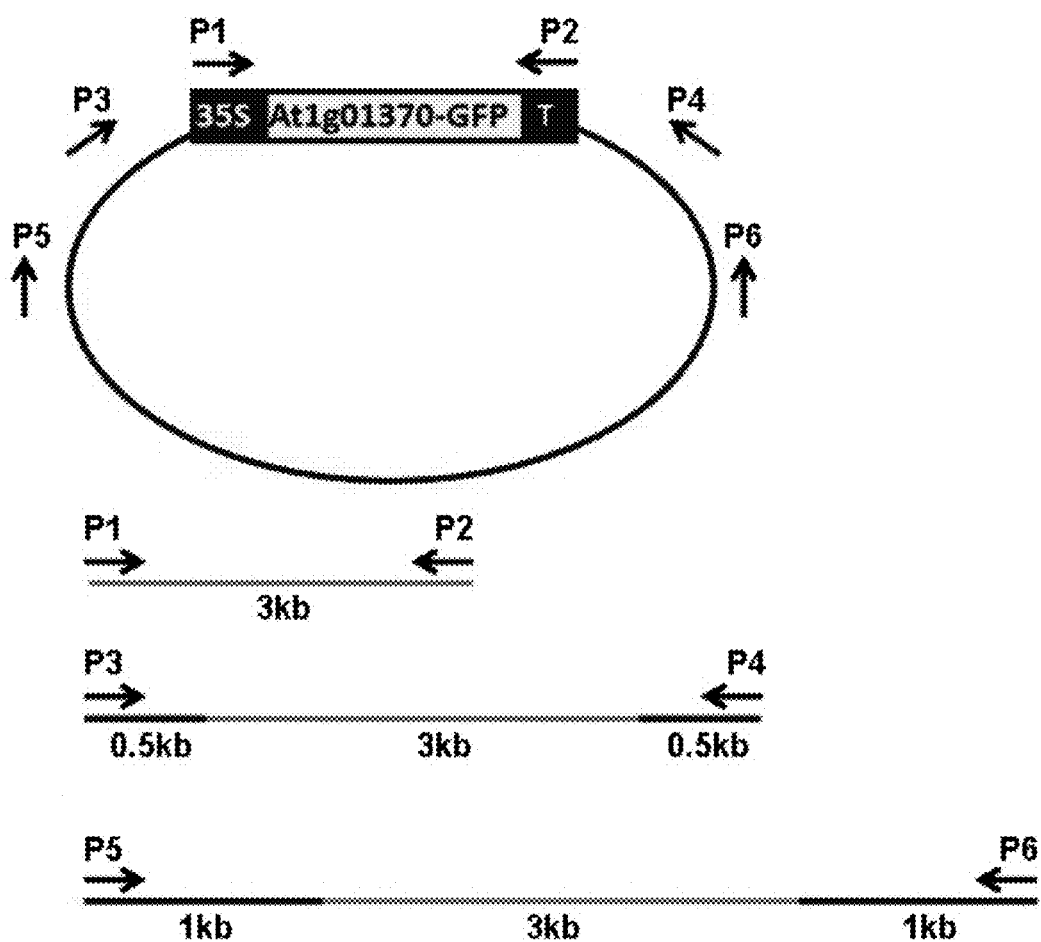
FIG. 17. A scheme representing primer design for the PPTT experiment shown in Example 9.

We compared impact of extra flanks around the "promoter-gene-GFP-terminator" expression cassette against transformation using plasmid DNA. Protoplast isolation and transformation using either tobacco or *Arabidopsis* leaf protoplasts was performed as previously described in this application. PCR products were amplified as shown on FIG. 17. Primers were designed to match this design: P1-gactagagccaagctgatctcctt (SEQ ID NO:140), P2-aggtcactggatttt-gttttagg (SEQ ID NO:141), P3-tgccggtgatcttctcggaaaaca (SEQ ID NO:142), P4-agaaaccatcggcgcagctattta (SEQ ID NO:143), P5-tcacttcctcgctgcgctcaagtg (SEQ ID NO:144), P6-tcgtattgggaatccccgaacatc (SEQ ID NO:145).

Figure 18:
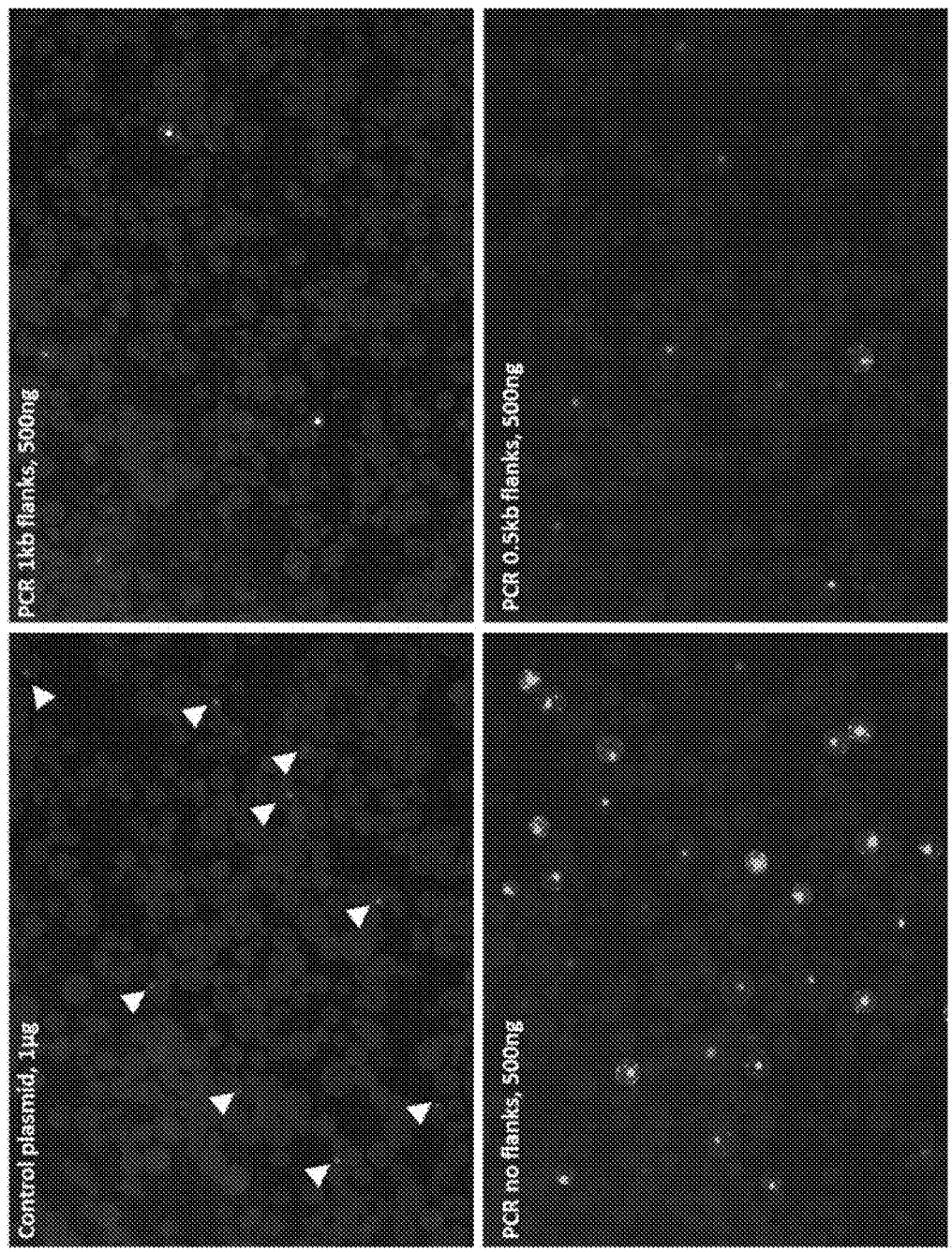
FIG. 18. Fluorescence microscopy analysis of transformation efficiencies using plasmid and PCR-expression cassettes in aqueous solution, 24 h after transformation (Example 9).

Transformation using dried or liquid PCR-amplified DNA product was performed, and both transformation procedures were efficient. Intriguingly, PPTT is working much more efficient in comparison to a standard, plasmid DNA-based transient transformation (FIG. 18). Furthermore, for plant species such as tobacco, in which transformation efficiencies when using plasmid DNA are always worse than in *Arabidopsis* increased number of transformed cells was observed (FIG. 18).

Experiment 2. Co-Expression of ER-mCherry Marker and At1g01730-GFP in Tobacco and *Arabidopsis* Protoplasts.

After PCR amplification and purification, ER-mCherry and At1g01730-GFP expression cassettes were mixed, dried, and PEG-mediated DNA uptake was performed. Microscopy analysis revealed co-expression of both genes in more than 95% of transformed cells for both, *Arabidopsis* and tobacco protoplasts.

Experiment 3. amiRNA, Split-FP Screenings Using PPTT

Figure 19:
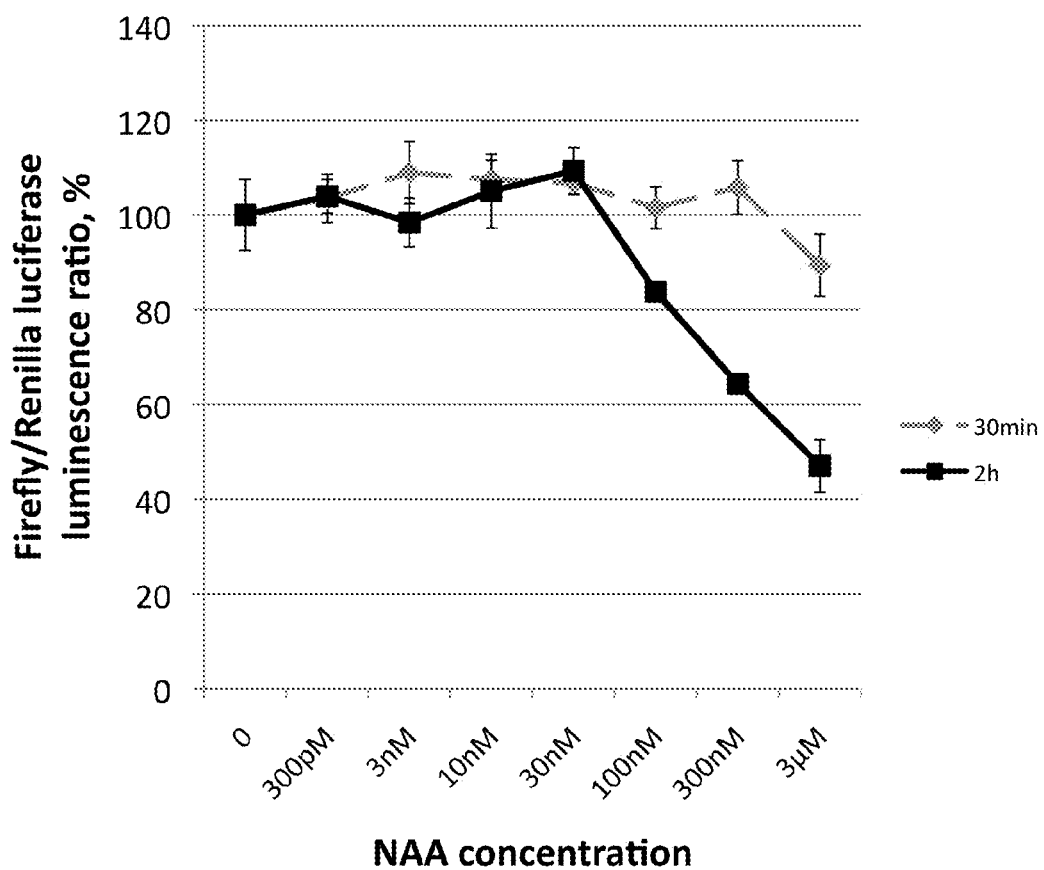
FIG. 19. Concentration-dependent effect of auxin NAA on firefly/renilla ratio (Example 9)

Our further aim to combine PPTT with amiRNA and other functional screenings such as split-GFP, split-YFP etc. Since co-expression of vectors works perfect, split screenings could be done straight away using confirmed interacting pair. Transformation with the luciferase reporter and subsequent luciferase activity measurements were successfully tested using auxin sensor construct (FIG. 19).

Figure 20A:
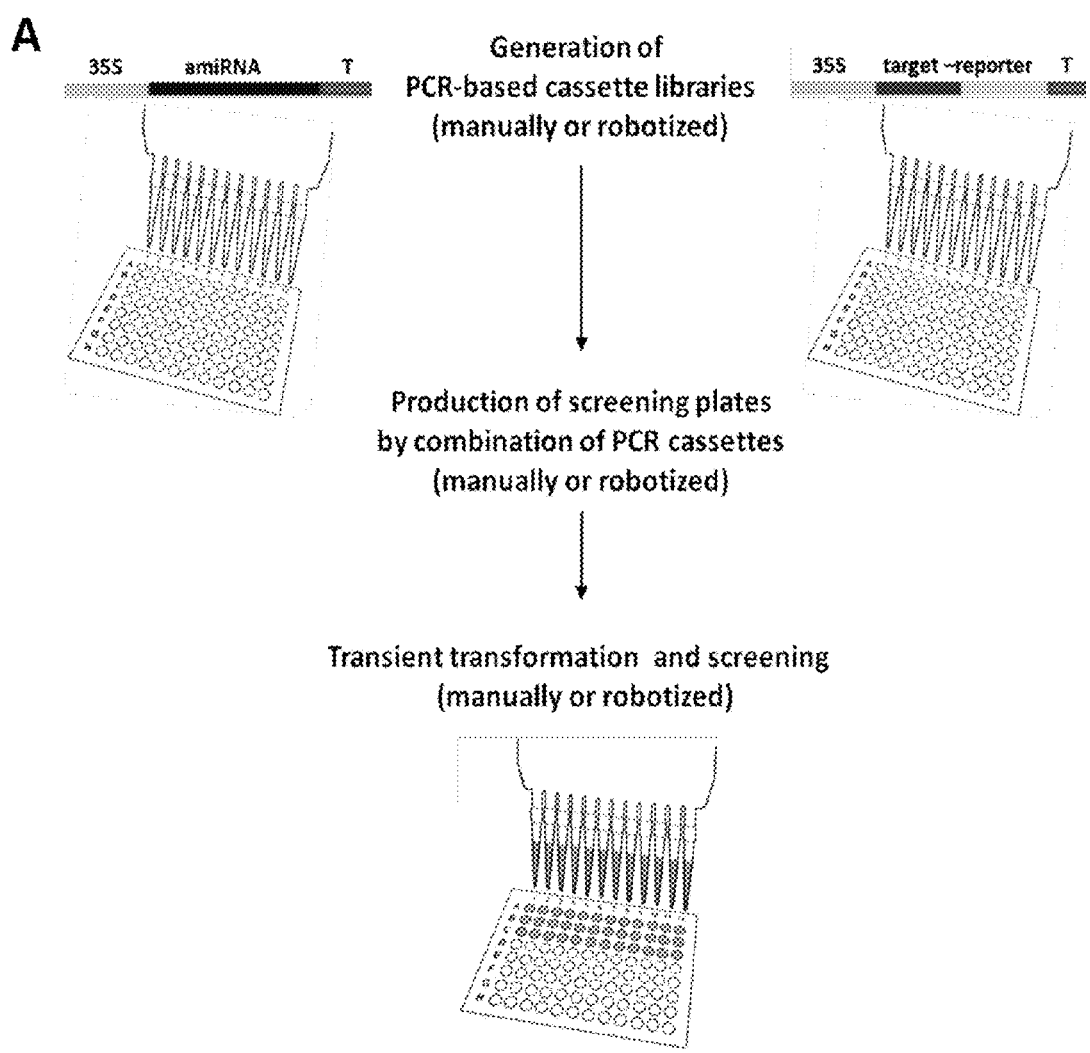
FIG. 20. Co-transformation (a) and single-product (b) PCR-based amiRNA screening strategies. All steps are applicable for automation.
Figure 20B:
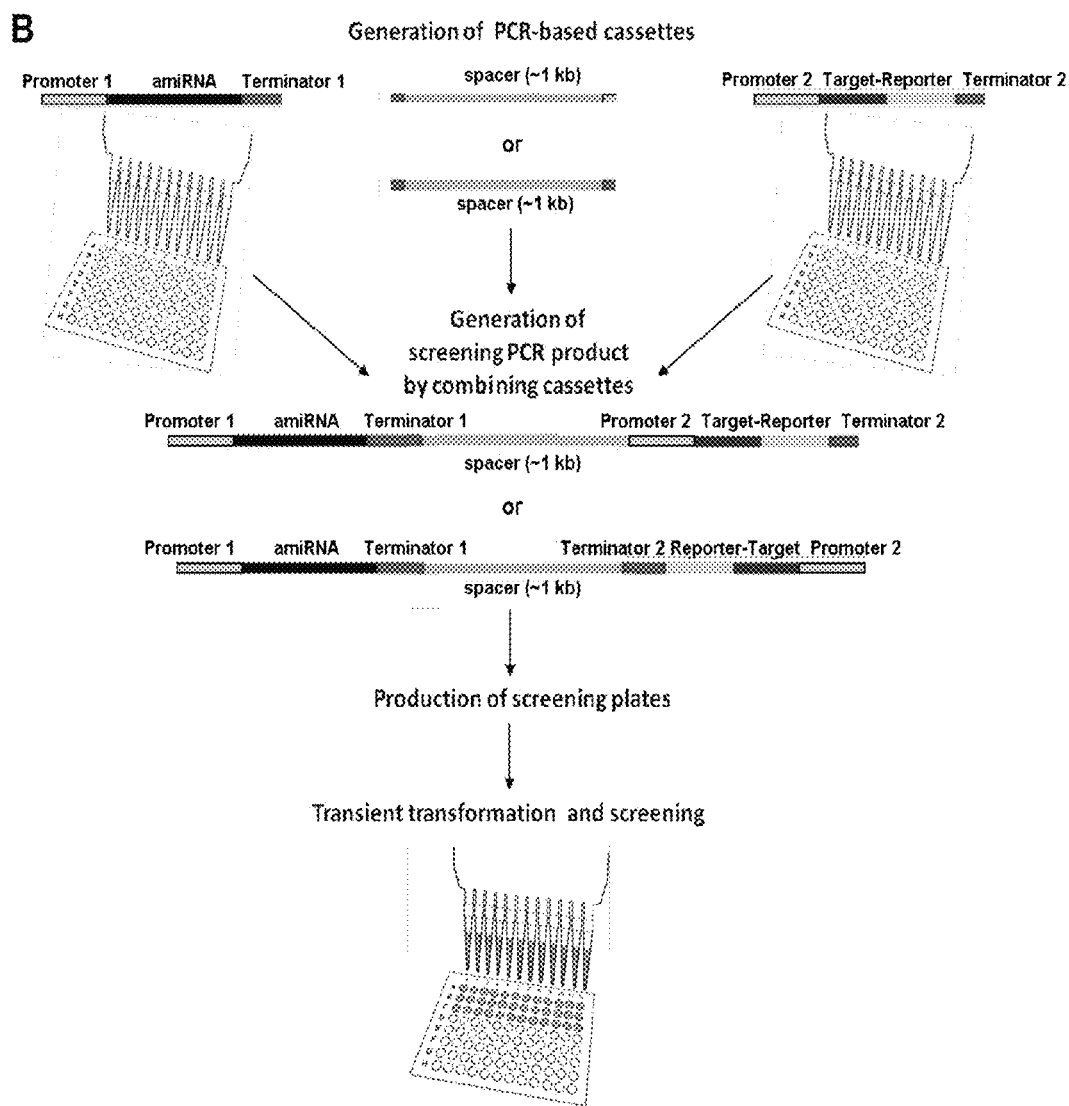

The amiRNA fluorescence based marker screening can be redesigned with luciferase activity evaluation using PPTT (FIG. 20). This design will allow completely automated sample manipulations, measurements and data reading where human will be responsible only for providing consumables and material, and transfer the screening plates from the robot to incubator and a reading instrument (microscope, plate-readers etc.). If needed, each step can be automated.

Example 10. Quantitative Analysis of Cellular Expansion Using PIN8, an Intracellular Modulator of Auxin Homeostasis Plant hormone auxin is an important regulator of plan growth, development and responses to environmental stimuli. The molecular mechanisms to actively transport this compound was evolved achieving the maximal complexity in higher plants. There are several protein families which are involved in regulation of auxin transport and generation of auxin gradients. One of them is PIN protein family which consists of 8 members in *Arabidopsis*, AtPIN1-AtPIN8. AtPINs are expressed specifically in different tissues being typically localized to the plasma membrane. Understanding of AtPIN function was crucial to understand the mechanism of auxin efflux as well as the auxin gradient formation in tissues and organs. However, currently there is no understanding, of how auxin is moved within the cell until it reaches the nucleus, where auxin-mediated regulation of gene expression takes place. Here we used single plant cells and intracellularly localized AtPIN5 and AtPIN8 to address this question.

Experiment Design:

We compared the effect of auxin concentration on cell elongation over a continuous period (4-6 days) using tobacco leaf protoplasts from wild type tobacco and from the tobacco line overexpressing AtPIN8 translationally fused with Venus fluorescent marker protein (PIN8VenusOx). Two strategies were used:
- effect of PIN5 and PIN8 expression on cell elongation using transient transformation with dried DNA, protoplast immobilization and culture with manual cell imaging and tracking.
- effect of auxin concentration (0, 1 pM, 10 pM, 100 pM, 500 pM, 1 nM, 10 nM, 100 nM, 500 nM, 1 µM, 2.5 µM, 5 µM, 10 µM, 25 µM and 50 µM) and quantitative analysis of cell elongation to compare wild type and PIN8VenusOx protoplasts using automated imaging (every 24 h for 4 days, 5 reference points) and computational image analysis.

Experiment 1. Functional Analysis of AtPIN5, AtPIN8 and AtPIN8Venus Expression in Tobacco Leaf Arotoplast.

Figure 15:
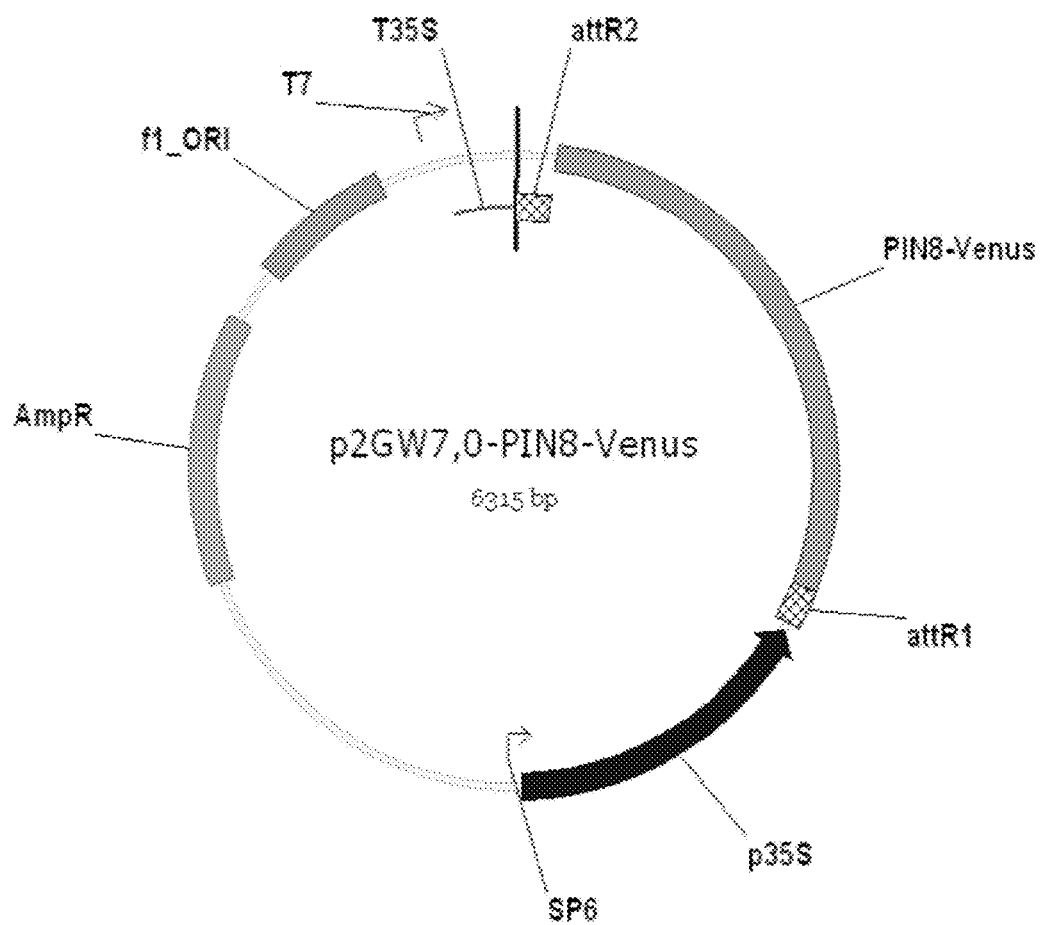
FIG. 15. Map and sequence of the vector p2GW7,0-PIN8-Venus for expression of the PIN8-Venus construct. The nucleotide sequence of p2GW7,0-PIN8-Venus is shown in SEQ ID NO:2.
Figure 16:
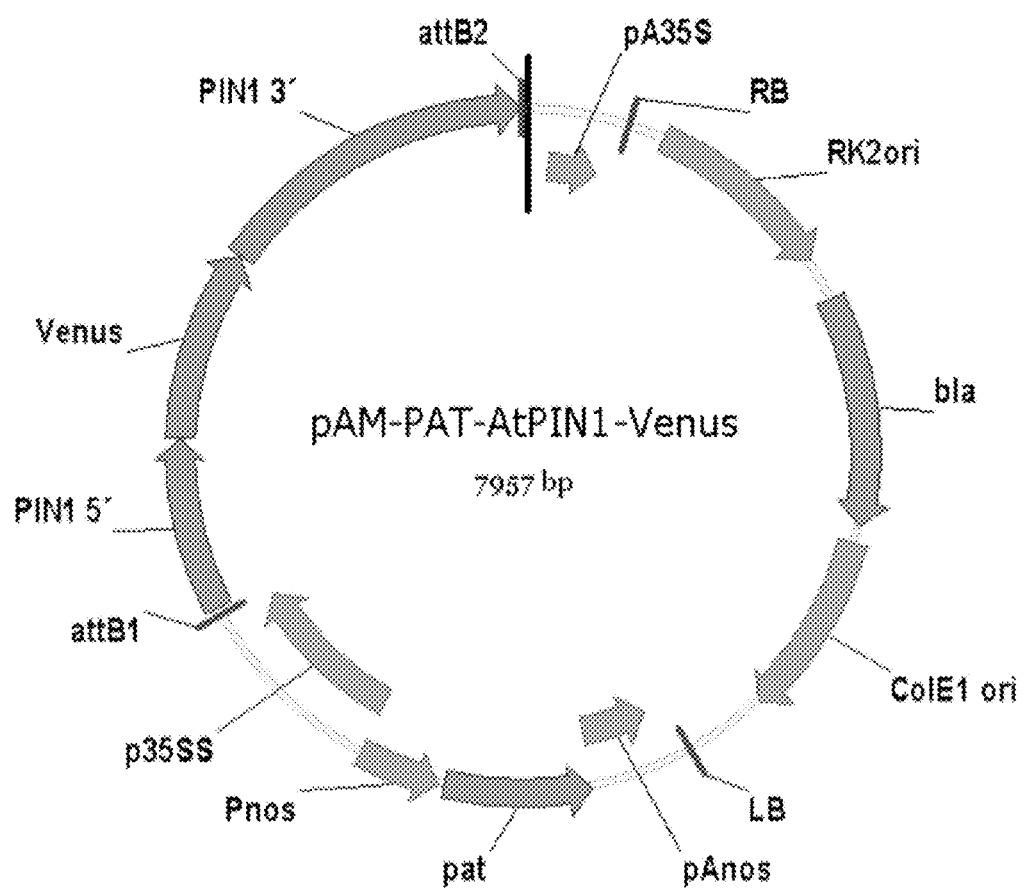
FIG. 16. Map of the vector pAM-PAT-AtPIN1-Venus for expression of the PIN1-Venus construct. The nucleotide sequence of pAM-PAT-AtPIN1-Venus is shown in SEQ ID NO:3.
Figure 21:
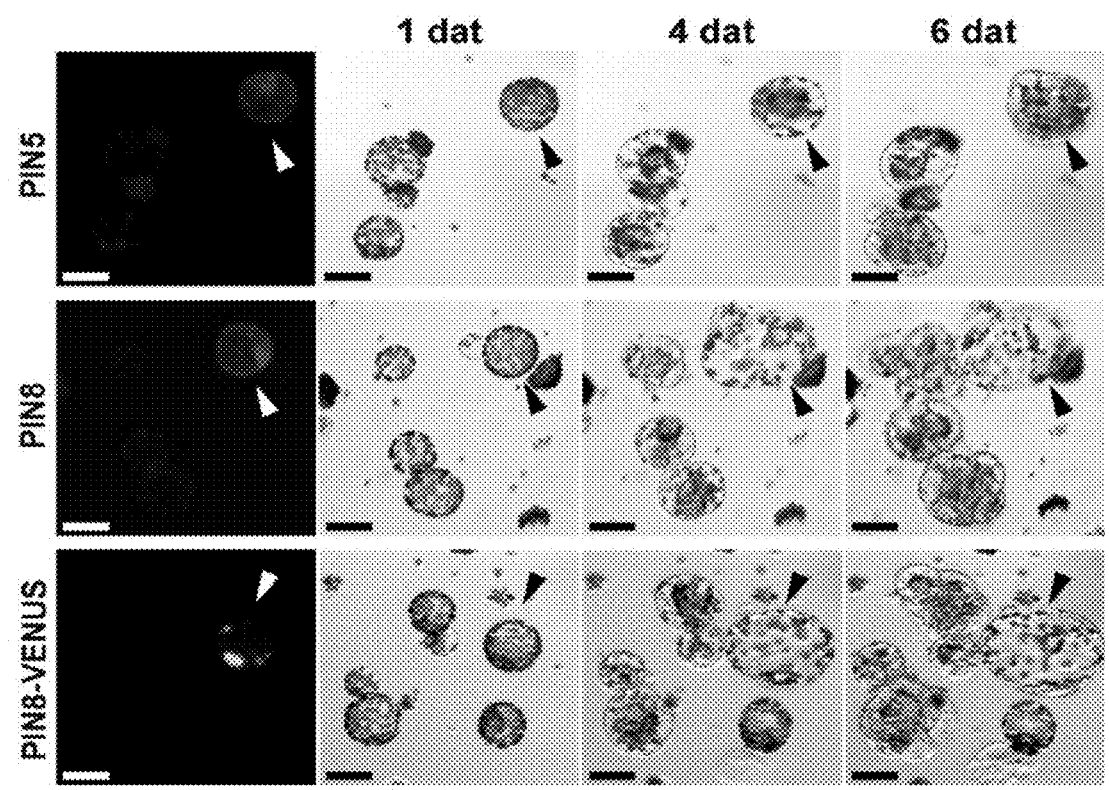
FIG. 21. Effect of PIN5 and PIN8 expression on tobacco leaf protoplast development. Transient PIN5 expression does not affect developmental program of tobacco leaf protoplasts, while expression of PIN8 arrests cell division and enhances elongation. Arrowheads indicate transformed cells. Scale bars are 20 μm.

Three plasmids were generated and used:
pAM-PAT-mCherry-PIN5 (PIN5, FIG. 21)
pAM-PAT-mCherry-PIN8 (PIN8, FIG. 21)
p2GW7,0-PIN8Venus (PIN8-Venus, FIG. 21)

pAM-PAT-mCherry-PIN5 and pAM-PAT-mCherry-PIN8 (both have backbone as in pAM-PAT-AtPIN1, FIG. 16 of the current application) contain mCherry expression cassette to identify transformed cells (transformation marker) and PIN5 or PIN8 expression cassettes without tags respectively. These constructs were used to compare the effect of PIN5 and PIN8 expression during protoplast development using cell tracking. Effect of Venus tag insertion in the coding sequence of AtPIN8 was compared using pAM-PAT-mCherry-PIN8 and p2GW7,0-PIN8Venus (this plasmid was used also in the Example 6, and FIG. 15 of the current application). As illustrated on images below, we observed no effect of PIN5 on cell elongation, while both, AtPIN8 and AtPIN8Ox had a similar effect resulting in enhanced cell elongation.

Transient PIN5 expression does not affect developmental program of tobacco leaf protoplasts, while expression of PIN8 arrests cell division and enhances elongation (FIG. 21).

Experiment 2. Quantitative Analysis of Transient AtPIN8 Expression on Expansion of Tobacco Leaf Protoplasts.

Figure 22:
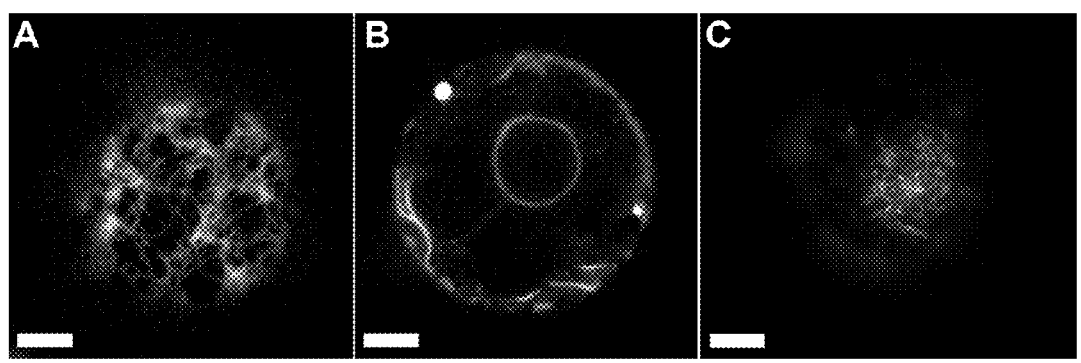
FIG. 22. Intracellular localization of AtPIN8-Venus in tobacco leaf protoplasts. Spinning-disk imaging at the cell periphery (a) and inside the cell (b) as well TIRF imaging near the plasma membrane (c) proves ER localization of AtPIN8-Venus (Andromeda microscope, TILL Photonics GmbH, Germany). Scale bars are 5 μm.

ER-targeting of AtPIN5 has been previously reported (Mravec et al. (2009) Subcellular homeostasis of phytohormone auxin is mediated by the ER-localized PIN5 transporter. Nature 459:1136-1140) we used Spinning-disk and TIRF microscopy method to analyze localization of AtPIN8, which is also targeted to ER (FIG. 22). It is important to stress, that our immobilization method allows using TIRF approach, which allows to study processes near plasma membrane and is possible only if the object (cell) is in a close proximity to a surface of imaging slide/plate.

Figure 23:
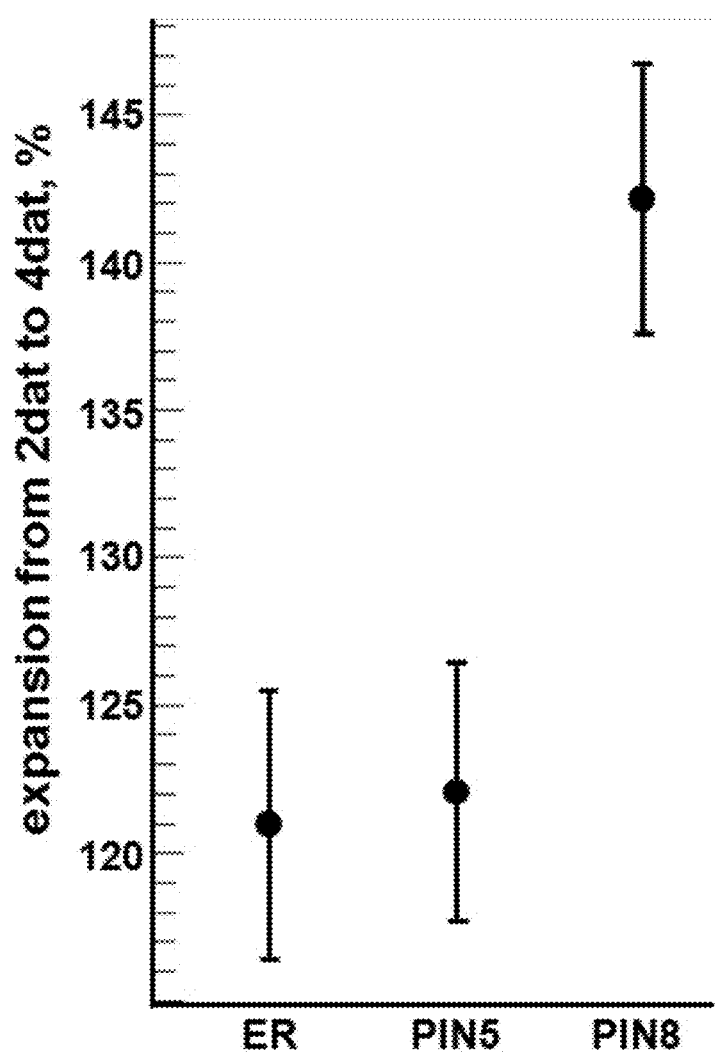
FIG. 23. Quantitative analysis of cell expansion between 2nd and 4th day of culture using tracking of cells expressing ER-mCherry marker, AtPIN5 and AtPIN8. Error bars represent 95% confidence intervals.

Therefore quantitative analysis and comparison of ER-marker, PIN5 and PIN8 was performed. pFGC19-ER-yb (Nelson B K et al. (2007) A multi-color set of in vivo organelle markers for colocalization studies in *Arabidopsis* and other plants Plant Journal 51:1126-1136) and pAM-PAT-mCherry-PIN5 and pAM-PAT-mCherry-PIN8 were used to transiently transform tobacco leaf protoplasts. Cell tracking, cell division analysis and quantitative measurements of cell diameter using ImageJ freeware were performed manually. AtPIN5 did not affect cell division rates in analyzed cells, while PIN8 inhibited cell divisions (Table 1). Only AtPIN8 enhanced cell elongation (FIG. 23).

TABLE 5

Analysis of cell division rates in transiently transformed cells.

| Sample | ER | PIN5 | PIN8 |
|---|---|---|---|
| total number of cells | 26 | 26 | 30 |
| dead cells (6dat) | 3 | 6 | 12 |
| non-dividing cells (6dat) | 10 | 7 | 18 |
| divided cells (6dat) | 13 | 13 | 0 |
| dead cells (6dat), % | 11.5 | 23 | 40 |
| non-divided cells (6dat), % | 38.5 | 27 | 60 |
| divided cells (6dat), % | 50 | 50 | 0 |

Figure 24A:
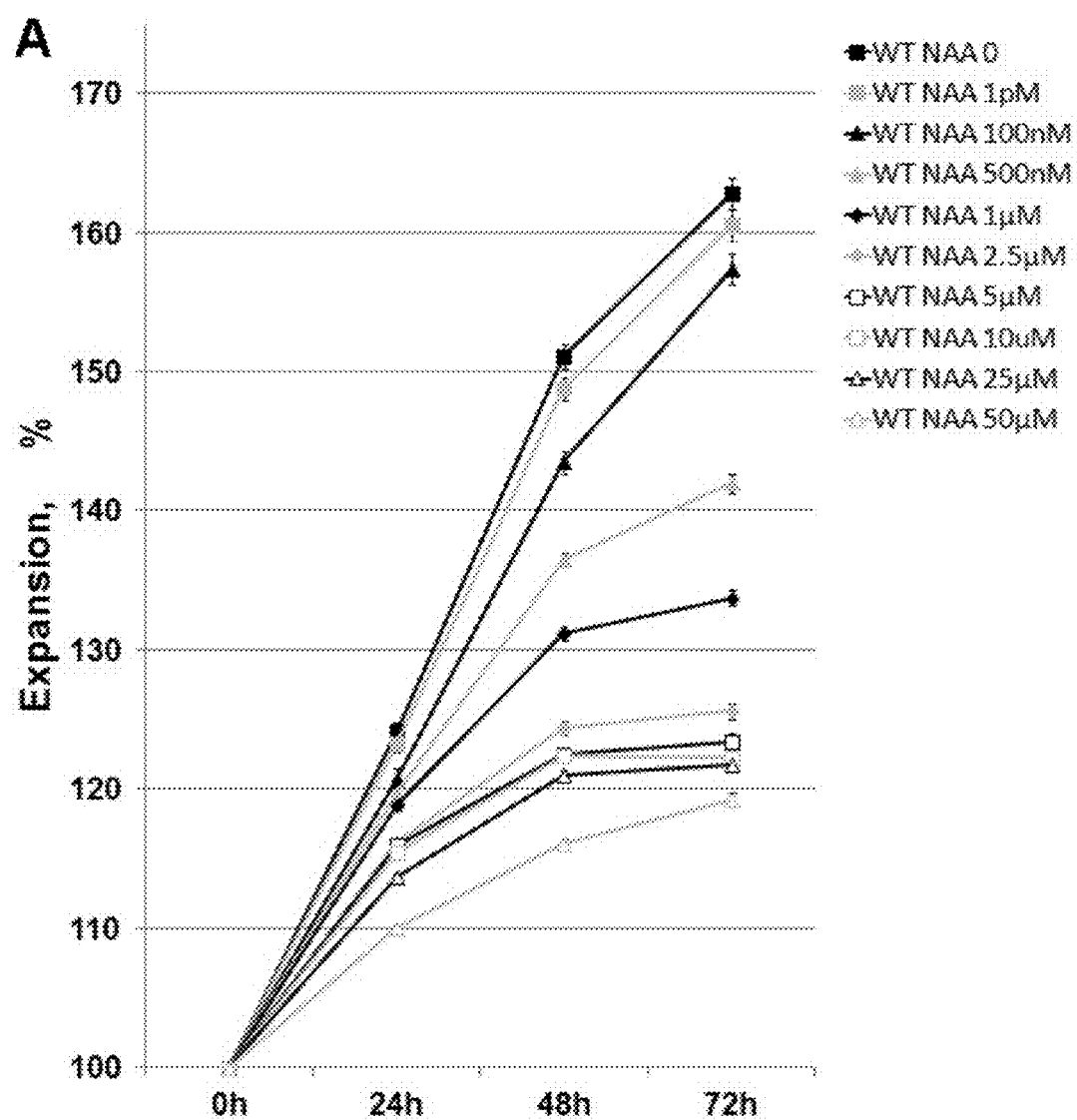
FIG. 24. Quantitative analysis of PIN8 effect on auxin mediated cell expansion. Concentration-depended cell expansion takes place for developing protoplasts from wild type tobacco (a) and significant loss of auxin-mediated response in protoplasts isolated from AtPIN8-Venus overexpressing line (b). At least 200 cells per group were analyzed. Error bars represent standard errors.
Figure 24B:
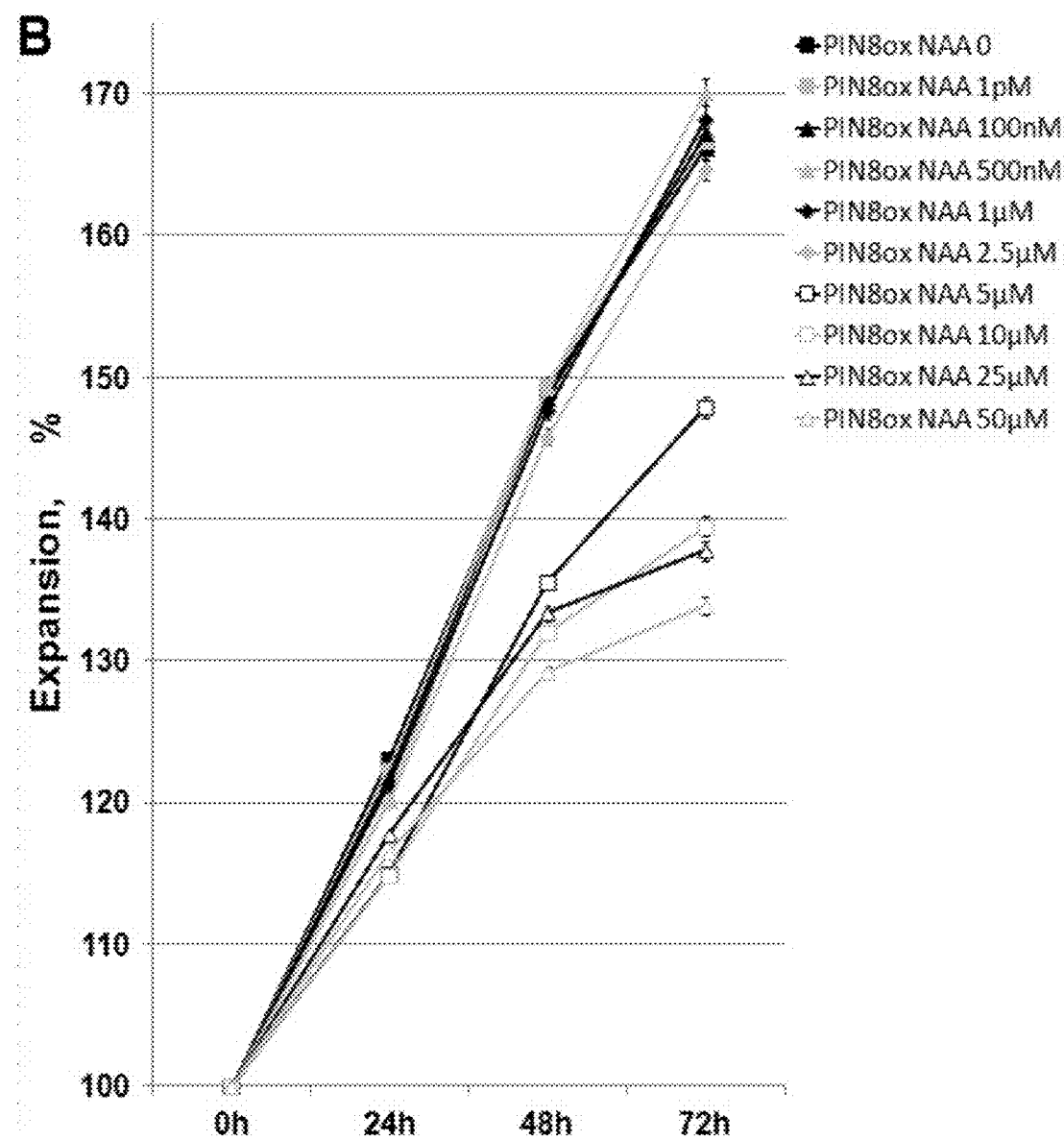

Experiment 3. Modulation of Intracellular Auxin Homeostasis Using AtPIN8 and Quantitative Analysis Protoplasts were isolated and immobilized using our procedure described in the current patent application. Culture medium with final auxin concentration of 0, 1 pM, 10 pM, 100 pM, 500 pM, 1 nM, 10 nM, 100 nM, 500 nM, 1 µM, 2.5 µM, 5 µM, 10 µM, 25 µM and 50 µM was used for washing steps and cell culture afterwards in corresponding wells. Automated image acquisition in a form of volume stacks was performed using iMIC microscope (TILL Photonics GmbH, Germany) in 24 h interval starting from the embedding (0 h, 24 h, 48 h, 72 h, 96 h). Recording coordinates were stored, and the plate was removed from the microscope after each imaging session. This results in non-significant shift in imaging areas, which did not affect further image analysis, and these cannot be achieved using any other existing protoplast culture systems at this or even greater scale. Image analysis (segmentation, cell identification, cell classification and parameter measurements, in this particular case a cell diameter) were performed by a tool which was specifically developed. This experiment allowed to extract quantitative information for hundreds cells per group, the whole experiment was performed in a single 96-well plate. Several training loops using expert knowledge were performed to achieve accuracy of cell identification over every time point (above 90%). This data were used for analysis of PIN8 effect (FIG. 24) and currently provide the basis of the primary mathematical model describing how auxin should move within the cell in order to achieve the nucleus and regulate gene expression.

The invention claimed is:

1. A method for introducing a polynucleotide into non-adhesively growing plant cells, comprising the following steps:
   a. providing a solid support having a polynucleotide in a dry state immobilized thereto;
   b. contacting non-adhesively growing plant cells with the polynucleotide on the solid support of step (a) so as to obtain transformed non-adhesively growing plant cells, wherein step (b) comprises:
      i. adding a suspension comprising the non-adhesively growing plant cells to the solid support of step (a),
      ii. sedimenting the non-adhesively growing plant cells, so as to arrange them in a layer on the solid support of step (a),
      iii. adding a transformation agent to the suspension; and
      iv. optionally removing the transformation agent from the non-adhesively growing plant cells; and
   c. optionally washing the non-adhesively growing plant cells.

2. The method of claim 1, wherein step (a) comprises adding a solution containing the polynucleotide onto the solid support and removing the water from the solution on the solid support.

3. The method of claim 1, wherein after step (iii) the non-adhesively growing plant cells are incubated for 1 to 30 minutes in the presence of the transformation agent so as to obtain the transformed non-adhesively growing plant cells and/or said transformation agent is selected from the group consisting of polyethylene glycol (PEG), poly-L-ornithine, polyvinyl alcohol and divalent ions.

4. The method according to claim 1, wherein, in step (a), at least 3 different polynucleotides are immobilized on the same solid support, each polynucleotide being spatially separated from the other polynucleotides and/or the solid support has a plurality of locations and each polynucleotide is immobilized at a separate location.

5. The method of claim 1, wherein said non-adhesively growing plant cells are plant protoplast cells.

6. The method of claim 1, wherein said polynucleotide comprises (i) a nucleic acid sequence encoding an artificial microRNA, (ii) a nucleic acid sequence representing a target gene of the artificial microRNA, and (iii) optionally a nucleic acid sequence encoding a transformation marker.

7. A method for analyzing non-adhesively growing cells, comprising the following steps:
   a. introducing a polynucleotide comprising at least one coding sequence into non-adhesively growing cells by a method according to claim 1 to obtain transformed non-adhesively growing cells;
   b. culturing the transformed non-adhesively growing cells under conditions that allow expression of the at least one coding sequence comprised in the polynucleotide;
   c. arranging the transformed non-adhesively growing cells in a monolayer and immobilizing them in the monolayer; and d. detecting at least one parameter by microscopic analysis.

8. The method of claim 7, wherein (i) the immobilization of the non-adhesively growing cells in a monolayer is achieved by adding a gelling substance to the non-adhesively growing cells, centrifuging the protoplast cells to obtain a monolayer of non-adhesively growing cells, and solidifying the gelling substance to form a gel in which the non-adhesively growing cells are embedded and/or (ii) said at least one parameter is selected from the group consisting of fluorescence, luminescence, morphology and combinations thereof.

9. A screening method to identify efficient plant microRNA sequences, comprising the following steps:
   a. introducing a polynucleotide into non-adhesively growing plant cells by the method of claim 6 so as to obtain transformed non-adhesively growing plant cells;
   b. culturing the transformed non-adhesively growing plant cells under conditions that allow expression of at least the nucleic acid sequence encoding the artificial microRNA, and the nucleic acid sequence representing the target gene of the artificial microRNA;
   c. designating the artificial microRNA sequence that is capable of inhibiting expression of the target gene as an efficient plant microRNA sequence.

10. The screening method of claim 9, wherein (i) the target gene is labeled with a first fluorescent protein, and the transformation marker is labeled with a second fluorescent protein and/or (ii) at least 24 different artificial microRNAs are examined in one screening cycle using one single solid support wherein the inhibition of expression of the target gene is determined by microscopy and/or (iii) the inhibition of expression of the target gene is determined by microscopy.

11. The method of claim 1, wherein said polynucleotide is a linear double-stranded DNA consisting of a promoter, an open reading frame, and a terminator, and wherein said nucleic acid is directly used for the transformation without inserting it into a plasmid.

12. The method according to claim 1, wherein said solid support has a plurality of separate cavities, each of which has said polynucleotide immobilized at its bottom.

13. The method of claim 1, wherein said non-adhesively growing plant cells are selected from the group consisting of cells from seeds, suspension cultures, embryos, meristematic regions, callus tissue, leaves, roots, shoots, gametophytes, sporophytes, pollen, and microspores.

14. The method of claim 1, wherein said non-adhesively growing plant cells comprise monocotyledonous or dicotyledonous plant cells.

15. The method of claim 1, wherein said non-adhesively growing plant cells comprise algae or mosses such as *Physcomitrella patens*.

16. The method of claim 1, wherein said non-adhesively growing plant cells are microspores.

17. An automated method for analyzing a cell, said method comprising the following steps:
   a. providing a solid support having a polynucleotide in a dry state immobilized thereto;
   b. adding a culture of non-adhesively growing cells to the solid support;
   c. arranging the non-adhesively growing cells in a monolayer on the solid support and immobilizing said cells in said monolayer;
   d. adding a transformation agent to the culture so as to obtain transformed non-adhesively growing cells;
   e. optionally removing the transformation agent from said transformed non-adhesively growing cells;
   f. optionally washing said transformed non-adhesively growing cells; and
   g. detecting at least one parameter of said transformed non-adhesively growing cells by microscopic analysis.

18. The method of claim 17, wherein
   (i) said non-adhesively growing cells are plant protoplast cells, and/or
   (ii) the immobilization of the non-adhesively growing cells in a monolayer is achieved by adding a gelling substance to the non-adhesively growing cells, centrifuging the protoplast cells to obtain a monolayer of non-adhesively growing cells, and solidifying the gelling substance to form a gel in which the non-adhesively growing cells are embedded, and/or
   (iii) said at least one parameter is selected from the group consisting of fluorescence, luminescence, morphology and combinations thereof.

19. The method of claim 17, wherein said polynucleotide comprises a linear double-stranded DNA consisting of a promoter, an open reading frame, and a terminator, and is directly used for the transformation without inserting it into a plasmid.

* * * * *